(12) United States Patent
Hoves et al.

(10) Patent No.: US 9,192,667 B2
(45) Date of Patent: Nov. 24, 2015

(54) METHOD OF TREATING CANCER BY ADMINISTERING CSF-1R ANTIBODIES AND A TLR9 AGONIST

(71) Applicant: Hoffmann-La Roche Inc., Nutley, NJ (US)

(72) Inventors: Sabine Hoves, Habach (DE); Carola Ries, Penzberg (DE); Dominik Ruettinger, Seehausen (DE); Katharina Wartha, Munich (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/257,480

(22) Filed: Apr. 21, 2014

(65) Prior Publication Data

US 2014/0314771 A1  Oct. 23, 2014

(30) Foreign Application Priority Data

Apr. 22, 2013 (EP) ..................................... 13164695

(51) Int. Cl.
| | |
|---|---|
| *A61K 39/395* | (2006.01) |
| *A61K 31/70* | (2006.01) |
| *A61K 45/06* | (2006.01) |
| *C07K 16/28* | (2006.01) |
| *A61K 31/7088* | (2006.01) |
| *A61K 39/00* | (2006.01) |

(52) U.S. Cl.
CPC ....... *A61K 39/39558* (2013.01); *A61K 31/7088* (2013.01); *A61K 45/06* (2013.01); *C07K 16/2866* (2013.01); *A61K 2039/505* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,202,238 A | 4/1993 | Fell, Jr. et al. | |
| 5,204,244 A | 4/1993 | Fell et al. | |
| 5,208,020 A | 5/1993 | Chari et al. | |
| 5,416,064 A | 5/1995 | Chari et al. | |
| 5,635,483 A | 6/1997 | Pettit et al. | |
| 5,712,374 A | 1/1998 | Kuntsmann et al. | |
| 5,714,586 A | 2/1998 | Kunstmann et al. | |
| 5,739,116 A | 4/1998 | Hamann et al. | |
| 5,767,285 A | 6/1998 | Hamann et al. | |
| 5,770,701 A | 6/1998 | McGahren et al. | |
| 5,770,710 A | 6/1998 | McGahren et al. | |
| 5,773,001 A | 6/1998 | Hamann et al. | |
| 5,780,588 A | 7/1998 | Pettit et al. | |
| 5,866,114 A | 2/1999 | Pandit et al. | |
| 5,877,296 A | 3/1999 | Hamann et al. | |
| 6,184,354 B1 | 2/2001 | Koths et al. | |
| 6,630,579 B2 | 10/2003 | Chari et al. | |
| 7,108,852 B2 | 9/2006 | Devalaraja et al. | |
| 7,498,298 B2 | 3/2009 | Doronina et al. | |
| 8,182,813 B2 | 5/2012 | Brasel et al. | |
| 8,470,977 B2 | 6/2013 | Haegel et al. | |
| 8,604,170 B2 | 12/2013 | Haegel et al. | |
| 2002/0141994 A1 | 10/2002 | Devalaraja et al. | |
| 2011/0081353 A1 | 4/2011 | Haegel et al. | |
| 2011/0165156 A1 | 7/2011 | Dimoudis et al. | |
| 2011/0178278 A1 | 7/2011 | Haegel et al. | |
| 2011/0274683 A1 | 11/2011 | Wong et al. | |
| 2012/0329997 A1 | 12/2012 | Fertig et al. | |
| 2013/0005949 A1 | 1/2013 | Fertig et al. | |
| 2013/0289250 A1 | 10/2013 | Haegel et al. | |
| 2013/0302322 A1 | 11/2013 | Wong et al. | |
| 2014/0057972 A1 | 2/2014 | Haegel et al. | |
| 2014/0079699 A1 | 3/2014 | Wong et al. | |
| 2014/0079706 A1 | 3/2014 | Cannarile et al. | |
| 2014/0120088 A1* | 5/2014 | Carpentier | ................. 424/133.1 |
| 2014/0205608 A1 | 7/2014 | Steidl et al. | |
| 2014/0255417 A1 | 9/2014 | Haegel et al. | |
| 2014/0314771 A1 | 10/2014 | Haves et al. | |
| 2014/0336363 A1 | 11/2014 | Fertig et al. | |
| 2015/0073129 A1 | 3/2015 | Herting et al. | |
| 2015/0080556 A1 | 3/2015 | Fertig et al. | |
| 2015/0158950 A1 | 6/2015 | Dimoudis et al. | |

FOREIGN PATENT DOCUMENTS

| | | |
|---|---|---|
| EP | 0425235 A2 | 5/1991 |
| EP | 0307434 B2 | 7/1998 |
| EP | 0 668 914 B1 | 8/2000 |
| EP | 2423288 A2 | 2/2012 |
| WO | WO-93/25687 A1 | 12/1993 |
| WO | WO-94/11026 A2 | 5/1994 |
| WO | WO-98/52976 A1 | 11/1998 |
| WO | WO-99/17798 A1 | 4/1999 |
| WO | WO-01/30381 A2 | 5/2001 |
| WO | WO-2004/045532 A2 | 6/2004 |
| WO | WO-2005/046657 A2 | 5/2005 |
| WO | WO-2006/012451 A2 | 2/2006 |
| WO | WO-2006/012451 A3 | 2/2006 |
| WO | WO-2006/096489 A2 | 9/2006 |
| WO | WO-2007/075326 A2 | 7/2007 |

(Continued)

OTHER PUBLICATIONS

Krieg AM, et al. Oncogene 27:161-167, 2008—available online at—doi:10.1038/sj.onc.1210911.*
U.S. Appl. No. 13/789,373, filed Mar. 20, 2014, Cannarile et al.
Abu-Duhier et al., "Mutational analysis of class III receptor tyrosine kinases (C-KIT, C-FMS, FLT3) in idiopathic myelofibrosis," Br J Haematol. 120(3):464-470 (2003).
Aharinejad et al., "Colony-stimulating factor-1 blockade by antisense oligonucleotides and small interfering RNAs suppresses growth of human mammary tumor xenografts in mice," Cancer Res. 64(15):5378-5384 (2004).
Anonymous, "MCSF Receptor antibody (ab 10676)" pp. 2 pages.
Ashmun et al., "Monoclonal antibodies to the human CSF-1 receptor (c-fms proto-oncogene product) detect epitopes on normal mononuclear phagocytes and on human myeloid leukemic blast cells," Blood. 73(3):827-837 (1989).

(Continued)

*Primary Examiner* — Robert Landsman
(74) *Attorney, Agent, or Firm* — Morrison & Foerster LLP

(57) ABSTRACT

The present invention relates to the combination therapy of antibodies against human CSF-1R with a TLR9 agonist.

13 Claims, 14 Drawing Sheets

(56) References Cited

FOREIGN PATENT DOCUMENTS

| WO | WO-2009/026303 A1 | 2/2009 |
|---|---|---|
| WO | WO-2009/112245 A1 | 9/2009 |
| WO | WO-2009/120903 A2 | 10/2009 |
| WO | WO-2009/120903 A3 | 10/2009 |
| WO | WO-2010/077634 A1 | 7/2010 |
| WO | WO-2011/066389 A1 | 6/2011 |
| WO | WO-2011/070024 A1 | 6/2011 |
| WO | WO-2011/107553 A1 | 9/2011 |
| WO | WO-2011/117329 A1 | 9/2011 |
| WO | WO-2011/123381 A1 | 10/2011 |
| WO | WO-2011/131407 A1 | 10/2011 |
| WO | WO-2011/140249 A2 | 11/2011 |
| WO | WO-2011/140249 A3 | 11/2011 |
| WO | WO-2012/110360 A1 | 8/2012 |
| WO | WO-2013/011021 A1 | 1/2013 |
| WO | WO-2013/057281 A2 | 4/2013 |
| WO | WO-2013/057281 A3 | 4/2013 |
| WO | WO-2013/079174 A1 | 6/2013 |
| WO | WO-2013/087699 A1 | 6/2013 |
| WO | WO-2013/119716 A1 | 8/2013 |
| WO | WO-2013/119716 A8 | 8/2013 |
| WO | WO-2013/132044 A1 | 9/2013 |
| WO | WO-2013/169264 A1 | 11/2013 |
| WO | WO-2014/072441 A1 | 5/2014 |
| WO | WO-2014/173814 A1 | 10/2014 |
| WO | WO-2015/036511 A1 | 3/2015 |

OTHER PUBLICATIONS

Baker et al., "Expression of the colony-stimulating factor 1 receptor in B lymphocytes," Oncogene. 8(2):371-378 (1993).

Balkwill et al., "Smoldering and polarized inflammation in the initiation and promotion of malignant disease," Cancer Cell. 7(3):211-217 (2005).

Balkwill, "TNF-alpha in promotion and progression of cancer," Cancer Metastasis Rev. 25(3):409-416 (2006).

Barnes et al., "Advances in animal cell recombinant protein production: GS-NS0 expression system," Cytotechnology. 32(2):109-123 (2000).

Barnes et al., "Characterization of the stability of recombinant protein production in the GS-NS0 expression system," Biotechnol Bioeng. 73(4):261-270 (2001).

Beiboer et al., "Guided selection of a pan carcinoma specific antibody reveals similar binding characteristics yet structural divergence between the original murine antibody and its human equivalent," J Mol Biol. 296(3):833-849 (2000).

Bingle et al., "The role of tumour-associated macrophages in tumour progression: implications for new anticancer therapies," J Pathol. 196(3):254-265 (2002).

Boackle et al., "An IgG primary sequence exposure theory for complement activation using synthetic peptides," Nature. 282(5740):742-743 (1979).

Boerner et al., "Production of antigen-specific human monoclonal antibodies from in vitro-primed human splenocytes," J Immunol. 147(1):86-95 (1991).

Bonham et al., "Antagonistic antibodies to c-fms block c-fms-mediated activities. reduce tumor-associated macrophages and decrease tumor growth in preclinical models," In Proc Am Assoc Cancer Res 50:503. Abstract #2077 (2009).

Bourette et al., "Early events in M-CSF receptor signaling," Growth Factors. 17(3):155-166 (2000).

Brunhouse et al., "Isotypes of IgG: comparison of the primary structures of three pairs of isotypes which differ in their ability to activate complement," Mol Immunol. 16(11):907-917 (1979).

Brüggemann et al., "Designer mice: the production of human antibody repertoires in transgenic animals," Year Immunol. 7:33-40 (1993).

Burmester et al., "Mavrilimumab, a human monoclonal antibody targeting GM-CSF receptor-[alpha], in subjects with rheumatoid arthritis: a randomised, double-blind, placebo-controlled, phase 1, first-in-human study," Ann Rheum Dis. 70(9):1542-9 (2011).

Burton et al., "The C1q receptor site on immunoglobulin G," Nature. 288:338-344 (1980).

Campbell et al., "The colony-stimulating factors and collagen-induced arthritis: exacerbation of disease by M-CSF and G-CSF and requirement for endogenous M-CSF," J Leukoc Biol. 68(1):144-150 (2000).

Carter et al., "Humanization of an anti-p185HER2 antibody for human cancer therapy," Proc Natl Acad Sci U S A. 89(10):4285-4289 (1992).

Casset et al., "A peptide mimetic of an anti-CD4 monoclonal antibody by rational design," Biochem Biophys Res Commun. 307:198-205 (2003).

Cenci et al., "M-CSF neutralization and Egr-1 deficiency prevent ovariectomy-induced bone loss," J Clin Invest. 105(9):1279-1287 (2000).

Chari et al., "Immunoconjugates containing novel maytansinoids: promising anticancer drugs," Cancer Res. 52(1):127-131 (1992).

Chase et al., "Imatinib sensitivity as a consequence of a CSF1R-Y571D mutation and CSF1/CSF1R signaling abnormalities in the cell line GDM1," Leukemia 23(2):358-64 (2009).

Choueiri et al., "The central role of osteoblasts in the metastasis of prostate cancer," Cancer Metastasis Rev. 25(4):601-609 (2006).

Cole et al., "The EBV-hybridoma technique and its application to human lung cancer," Monoclonal Antibodies and Cancer Therapy. Alan R. Liss, Inc. 77-96 (1985).

Coussens et al., "Structural alteration of viral homologue of receptor proto-oncogene fms at carboxyl terminus," Nature. 320(6059):277-280 (1986).

da Costa et al., "Presence of osteoclast-like multinucleated giant cells in the bone and nonostotic lesions of Langerhans cell histiocytosis," J Exp Med. 201(5):687-693 (2005).

Dai et al., "Targeted disruption of the mouse colony-stimulating factor 1 receptor gene results in osteopetrosis, mononuclear phagocyte deficiency, increased primitive progenitor cell frequencies, and reproductive defects," Blood. 99(1):111-120 (2002).

Daroszewska et al., "Mechanisms of disease: genetics of Paget's disease of bone and related disorders," Nat Clin Pract Rheumatol. 2(5):270-277 (2006).

Davies et al., "Affinity improvement of single antibody VH domains: residues in all three hypervariable regions affect antigen binding," Immunotechnology. 2(3):169-179 (1996).

Drees et al., "Mechanisms of disease: Molecular insights into aseptic loosening of orthopedic implants," Nat Clin Pract Rheumatol. 3(3):165-171 (2007).

Dubowchik et al., "Doxorubicin immunoconjugates containing bivalent, lysosomally-cleavable dipeptide linkages," Bioorg Med Chem Lett. 12(11):1529-1532 (2002).

Durocher et al., "High-level and high-throughput recombinant protein production by transient transfection of suspension-growing human 293-EBNA1 cells," Nucleic Acids Res. 30(2):E9 (2002).

Feldstein et al., "Practice patterns in patients at risk for glucocorticoid-induced osteoporosis," Osteoporos Int. 16(12):2168-2174 (2005).

Flatman et al., "Process analytics for purification of monoclonal antibodies," J Chromatogr B Analyt Technol Biomed Life Sci. 848(1):79-87 (2007).

Geisse et al., "Eukaryotic expression systems: a comparison," Protein Expr Purif. 8(3):271-282 (1996).

Guzman-Clark et al., "Barriers in the management of glucocorticoid-induced osteoporosis," Arthritis Rheum. 57(1):140-146 (2007).

Hamilton, "Colony-stimulating factors in inflammation and autoimmunity," Nat Rev Immunol. 8(7):533-544 (2008).

Hao et al., "Expression of macrophage colony-stimulating factor and its receptor in microglia activation is linked to teratogen-induced neuronal damage," Neuroscience. 112(4):889-900 (2002).

Hezareh et al., "Effector function activities of a panel of mutants of a broadly neutralizing antibody against human immunodeficiency virus type 1," J Virol. 75(24):12161-12168 (2001).

Hinman et al., "Preparation and characterization of monoclonal antibody conjugates of the calicheamicins: a novel and potent family of antitumor antibiotics," Cancer Res. 53(14):3336-3342 (1993).

Holt et al., "Domain antibodies: proteins for therapy," Trends Biotechnol. 21(11):484-490 (2003).

(56) References Cited

OTHER PUBLICATIONS

Hoogenboom et al., "By-passing immunisation. Human antibodies from synthetic repertoires of germline VH gene segments rearranged in vitro," J Mol Biol. 227(2):381-388 (1992).
Huston et al., "Protein engineering of single-chain Fv analogs and fusion proteins," Methods Enzymol. 203:46-88 (1991).
Idusogie et al., "Mapping of the C1q binding site on rituxan, a chimeric antibody with a human IgG1 Fc," J Immunol. 164(8):4178-4184 (2000).
Ikonomidis et al., "Increased circulating C-reactive protein and macrophage-colony stimulating factor are complementary predictors of long-term outcome in patients with chronic coronary artery disease," Eur Heart J. 26(16):1618-1624 (2005).
Inaba et al., "Expression of M-CSF receptor encoded by c-fms on smooth muscle cells derived from arteriosclerotic lesion," J Biol Chem. 267(8):5693-5699 (1992).
Jakobovits et al., "Analysis of homozygous mutant chimeric mice: deletion of the immunoglobulin heavy-chain joining region blocks B-cell development and antibody production," Proc Natl Acad Sci U S A. 90(6):2551-2555 (1993).
Jakobovits et al., "Germ-line transmission and expression of a human-derived yeast artificial chromosome," Nature. 362(6417):255-258 (1993).
Jeffrey et al., "Dipeptide-based highly potent doxorubicin antibody conjugates," Bioorg Med Chem Lett. 16(2):358-362 (2006).
Johnson et al., "Kabat database and its applications: 30 years after the first variability plot," Nucleic Acids Res. 28(1):214-218 (2000).
Kabat et al., "Tabulation and analysis of amino acid and nucleic acid sequences of precursors, v-regions, c-regions, j-chain, beta2-microglobulins, major histocompatibility antigens, thy-1, complement, c-reactive protein, thymopoietin, post-gamma globulin, and alpha2-macroglobulin," Sequences of Proteins of Immunological Interest. U.S. Department of Health and Human Services, 10L (1983).
Kacinski, "CSF-1 and its receptor in breast carcinomas and neoplasms of the female reproductive tract," Mol Reprod Dev. 46(1):71-74 (1997).
Kaku et al., "Amyloid beta protein deposition and neuron loss in osteopetrotic (op/op) mice," Brain Res Protoc. 12(2):104-108 (2003).
Kaufman, "Overview of vector design for mammalian gene expression," Mol Biotechnol. 16(2):151-160 (2000).
King et al., "Monoclonal antibody conjugates of doxorubicin prepared with branched peptide linkers: inhibition of aggregation by methoxytriethyleneglycol chains," J Med Chem. 45(19):4336-4343 (2002).
Kirma et al., "Elevated expression of the oncogene c-fms and its ligand, the macrophage colony-stimulating factor-1, in cervical cancer and the role of transforming growth factor-beta1 in inducing c-fms expression," Cancer Res. 67(5):1918-1926 (2007).
Kitaura et al., "An anti-c-Fms antibody inhibits orthodontic tooth movement," J Dent Res. 87(4):396-400 (2008).
Kitaura et al., "M-CSF mediates TNF-induced inflammatory osteolysis," J Clin Invest. 115(12):3418-3427 (2005).
Kratz et al., "Prodrugs of anthracyclines in cancer chemotherapy," Curr Med Chem. 13(5):477-523 (2006).
Lee et al., "Functional dissection of structural domains in the receptor for colony-stimulating factor-1," J Biol Chem. 267(23):16472-16483 (1992).
Lee et al., "The Cbl protooncoprotein stimulates CSF-1 receptor multiubiquitination and endocytosis, and attenuates macrophage proliferation," EMBO J. 18(13):3616-3628 (1999).
Lenda et al., "Reduced macrophage recruitment, proliferation, and activation in colony-stimulating factor-1-deficient mice results in decreased tubular apoptosis during renal inflammation," J Immunol. 170(6):3254-3262 (2003).
Lester et al., "Current management of treatment-induced bone loss in women with breast cancer treated in the United Kingdom," Br J Cancer. 94(1):30-35 (2006).
Lewis et al., "Distinct apoptotic signaling characteristics of the anti-CD40 monoclonal antibody dacetuzumab and rituximab produce enhanced antitumor activity in non-Hodgkin lymphoma," Clin Cancer Res. 17(14):4672-4681 (2011).
Li et al., "Combination of intratumoral CpG with systemic anti-OX40 and anti-CTLA4 mAbs eradicates established triple negative breast tumors in mice," Cancer Research (retrieved from <http://cancerres.aacrjournals.org/cgi/content/meetings_abstract/72/24_MeetingAbstracts/P4-04-01>). 72(24):1-2 (2012).
Li et al., "Role of dimerization and modification of the CSF-1 receptor in its activation and internalization during the CSF-1 response," EMBO J. 10(2):277-288 (1991).
Lin et al., "Discovery of a cytokine and its receptor by functional screening of the extracellular proteome," Science 320(5877):807-811 (2008).
Lode et al., "Targeted therapy with a novel enediyene antibiotic calicheamicin theta(I)1 effectively suppresses growth and dissemination of liver metastases in a syngeneic model of murine neuroblastoma," Cancer Res. 58(14):2925-2928 (1998).
Lukas et al., "Inhibition of C1-mediated immune hemolysis by monomeric and dimeric peptides from the second constant domain of human immunoglobulin $G^1$," J Immunol. 127(6):2555-2560 (1981).
MacCallum et al., "Antibody-antigen interactions: contact analysis and binding site topography," J Mol Biol. 262:732-745 (1996).
MacDonald et al., "An antibody against the colony-stimulating factor 1 receptor depletes the resident subset of monocytes and tissue- and tumor-associated macrophages but does not inhibit inflammation," Blood. 116(19):3955-63 (2010).
Makrides, "Components of vectors for gene transfer and expression in mammalian cells," Protein Expr Purif. 17(2):183-202 (1999).
Mantovani et al., "The chemokine system in diverse forms of macrophage activation and polarization," Trends Immunol. 25(12):677-686 (2004).
Marks et al., "By-passing immunization. Human antibodies from V-gene libraries displayed on phage," J Mol Biol. 222(3):581-597 (1991).
Martin et al., "Growth and angiogenesis of human breast cancer in a nude mouse tumour model is reduced by NK4, a HGF/SF antagonist," Carcinogenesis. 24(8):1317-1323 (2003).
Morgan et al., "The N-terminal end of the CH2 domain of chimeric human IgG1 anti-HLA-DR is necessary for C1q, Fc gamma RI and Fc gamma RIII binding," Immunology. 86(2):319-324 (1995).
Morrison et al., "Chimeric human antibody molecules: mouse antigen-binding domains with human constant region domains," Proc Natl Acad Sci U S A. 81(21):6851-6855 (1984).
Murad et al., "CpG oligodeoxynucleotides as TLR9 agonists: therapeutic applications in cancer," BioDrugs. 23(6):361-75 (2009).
Murayama et al., "Intraperitoneal administration of anti-c-fms monoclonal antibody prevents initial events of atherogenesis but does not reduce the size of advanced lesions in apolipoprotein E-deficient mice," Circulation. 99(13):1740-1746 (1999).
Murphy et al., "Expression of macrophage colony-stimulating factor receptor is increased in the AbetaPP(V717F) transgenic mouse model of Alzheimer's disease," Am J Pathol. 157(3):895-904 (2000).
Murphy et al., "Macrophage colony-stimulating factor augments beta-amyloid-induced interleukin-1, interleukin-6, and nitric oxide production by microglial cells," J Biol Chem. 273(33):20967-20971 (1998).
Nagy et al., "Stability of cytotoxic luteinizing hormone-releasing hormone conjugate (AN-152) containing doxorubicin 14-O-hemiglutarate in mouse and human serum in vitro: implications for the design of preclinical studies," Proc Natl Acad Sci U S A. 97(2):829-834 (2000).
Neuberger et al., "A hapten-specific chimaeric IgE antibody with human physiological effector function," Nature. 314(6008):268-270 (1985).
Ngan et al., "Proto-oncogenes and p53 protein expression in normal cervical stratified squamous epithelium and cervical intra-epithelial neoplasia," Eur J Cancer. 35(10):1546-1550 (1999).
Nicola et al., "Neutralizing and nonneutralizing monoclonal antibodies to the human granulocyte-macrophage colony-stimulating factor receptor alpha-chain," Blood. 82(6):1724-31 (1993).
Norderhaug et al., "Versatile vectors for transient and stable expression of recombinant antibody molecules in mammalian cells," J Immunol Methods. 204(1):77-87 (1997).

(56) References Cited

OTHER PUBLICATIONS

Orlandi et al., "Cloning immunoglobulin variable domains for expression by the polymerase chain reaction," Proc Natl Acad Sci U S A. 86(10):3833-3837 (1989).
Patel et al., "Colony-stimulating factor-1 receptor inhibitors for the treatment of cancer and inflammatory disease," Curr Top Med Chem. 9(7):599-610 (2009).
Paul, Structure and funtcion of immunoglobulins, *Fundamental Immunology*, 3rd Ed., Raven Press, 292-295 (1993).
Paulus et al., "Colony-stimulating factor-1 antibody reverses chemoresistance in human MCF-7 breast cancer xenografts," Cancer Res. 66(8):4349-4356 (2006).
Pixley et al., "CSF-1 regulation of the wandering macrophage: complexity in action," Trends Cell Biol. 14(11):628-638 (2004).
Pollard, "Role of colony-stimulating factor-1 in reproduction and development," Mol Reprod Dev. 46(1):54-60 (1997).
Pollard, "Tumour-educated macrophages promote tumour progression and metastasis," Nat Rev Cancer. 4(1):71-78 (2004).
Queen et al., "A humanized antibody that binds to the interleukin 2 receptor," Proc Natl Acad Sci U S A. 86(24):10029-10033 (1989).
Rabello et al., "CSF1 gene associated with aggressive periodontitis in the Japanese population," Biochem Biophys Res Commun. 347(3):791-796 (2006).
Ridge et al., "FMS mutations in myelodysplastic, leukemic, and normal subjects," Proc Natl Acad Sci U S A. 87(4):1377-1380 (1990).
Riechmann et al., "Reshaping human antibodies for therapy," Nature. 332(6162): 323-327 (1988).
Ritchlin et al., "Mechanisms of TNF-alpha- and RANKL-mediated osteoclastogenesis and bone resorption in psoriatic arthritis," J Clin Invest. 111(6):821-831 (2003).
Roggia et al., "Role of TNF-alpha producing T-cells in bone loss induced by estrogen deficiency," Minerva Med. 95(2):125-132 (2004).
Roth et al., "The biology of CSF-1 and its receptor," Curr Top Microbiol Immunol. 181:141-167 (1992).
Roussel et al., "Mouse NIH 3T3 cells expressing human colony-stimulating factor 1 (CSF-1) receptors overgrow in serum-free medium containing human CSF-1 as their only growth factor," Proc Natl Acad Sci U S A. 86(20):7924-7927 (1989).
Roussel et al., "Transforming potential of the c-fms proto-oncogene (CSF-1 receptor)," Nature. 325(6104):549-552 (1987).
Saitoh et al., "Clinical significance of increased plasma concentration of macrophage colony-stimulating factor in patients with angina pectoris," J Am Coll Cardiol. 35(3):655-665 (2000).
Sawada et al., "Activation and proliferation of the isolated microglia by colony stimulating factor-1 and possible involvement of protein kinase C," Brain Res. 509(1):119-124 (1990).
Schlaeger et al., "Transient gene expression in mammalian cells grown in serum-free suspension culture," Cytotechnology. 30(1-3):71-83 (1999).
Schlaeger, "The protein hydrolysate, Primatone RL, is a cost-effective multiple growth promoter of mammalian cell culture in serum-containing and serum-free media and displays anti-apoptosis properties," J Immunol Methods. 194(2):191-199 (1996).
Scholl et al., "Anti-colony-stimulating factor-1 antibody staining in primary breast adenocarcinomas correlates with marked inflammatory cell infiltrates and prognosis," J Natl Cancer Inst. 86(2):120-126 (1994).
Sherr et al., "Inhibition of colony-stimulating factor-1 activity by monoclonal antibodies to the human CSF-1 receptor," Blood. 73(7):1786-83 (1989).
Sherr et al., "The c-fms proto-oncogene product is related to the receptor for the mononuclear phagocyte growth factor, CSF-1," Cell. 41(3):665-676 (1985).
Stanley et al., "The biology and action of colony stimulating factor-1," Stem Cells. 12(Suppl 1):15-25 (1994).
Stoch et al., "Bone loss in men with prostate cancer treated with gonadotropin-releasing hormone agonists," J Clin Endocrinol Metab. 86(6):2787-2791 (2001).
Sudo et al., "Functional hierarchy of c-kit and c-fms in intramarrow production of CFU-M," Oncogene. 11(12):2469-2476 (1995). Abstract Only.
Tanaka et al., "Macrophage colony-stimulating factor is indispensable for both proliferation and differentiation of osteoclast progenitors," J Clin Invest. 91(1):257-263 (1993).
Thommesen et al., "Lysine 322 in the human IgG3 C(H)2 domain is crucial for antibody dependent complement activation," Mol Immunol. 37(16):995-1004 (2000).
Torgov et al., "Generation of an intensely potent anthracycline by a monoclonal antibody-beta-galactosidase conjugate," Bioconjugate Chem. 16(3):717-721 (2005).
Tortora et al., "Novel toll-like Receptor 9 (TLR9) agonists IMO inhibits tumor growth and cooperates with cetuximab in K-Ras mutant colon pancreatic cancers," Proceedings of the American Association for Cancer Research. 51:146 (2010).
van Dijk et al., "Human antibodies as next generation therapeutics," Curr Opin Chem Biol. 5(4):368-374 (2001).
Vessella et al., "Targeting factors involved in bone remodeling as treatment strategies in prostate cancer bone metastasis," Clin Cancer Res. 12(20 Pt 2):6285s-6290s (2006).
Vitetta et al., "Redesigning nature's poisons to create anti-tumor reagents," Science. 238(4830):1098-1104 (1987).
Wang et al., "Identification of the ligand-binding regions in the macrophage colony-stimulating factor receptor extracellular domain," Mol Cell Biol. 13(9):5348-59 (1993).
Werner et al., "Appropriate mammalian expression systems for biopharmaceuticals," Arzneimittelforschung. 48(8):870-880 (1998).
West et al., "A landscape effect in tenosynovial giant-cell tumor from activation of CSF1 expression by a translocation in a minority of tumor cells," Proc Natl Aced Sci U S A. 103(3):690-695 (2006).
Yang et al., "The relationship between point mutation and abnormal expression of c-fms oncogene in hepatocellular carcinoma," Hepatobiliary Pancreat Dis Int. 3(1):86-89 (2004).
Yeung et al., "Proteomic approaches to the analysis of early events in colony-stimulating factor-1 signal transduction," Mol Cell Proteomics. 2(11):1143-1155 (2003).
Zheng et al., "Membrane-bound macrophage colony-stimulating factor and its receptor play adhesion molecule-like roles in leukemic cells," Leuk Res. 24(5):375-383 (2000).
Zins et al., "Colon cancer cell-derived tumor necrosis factor-alpha mediates the tumor growth-promoting response in macrophages by up-regulating the colony-stimulating factor-1 pathway," Cancer Res. 67(3):1038-1045 (2007).
English Translation of Notification of Reasons for Rejection for Japanese Patent Application No. 2012-542522, dated Feb. 25, 2014 (3 pages).
Extended Search Report for European Patent Application No. 09007224.0, dated Nov. 24, 2009 (9 pages).
Extended Search Report for European Patent Application No. 09015310.7, dated Sep. 20, 2010 (8 pages).
Extended Search Report for European Patent Application No. 12158519.4, dated Aug. 2, 2012 (8 pages).
International Search Report for International Patent Application No. PCT/EP2012/075241, mailed Feb. 22, 2013 (5 pages).
International Search Report for International Patent Application No. PCT/EP2011/053214, mailed Apr. 28, 2011 (4 pages).
International Search Report for International Patent Application No. PCT/EP2013/054676, mailed May 7, 2013 (7 pages).
International Search Report for International Patent Application No. PCT/EP2012/075241, mailed Feb. 22, 2013 (7 pages).
Affymetrix Ebioscience. (2000-2014). "Anti-Mouse CD115 (c-fms) Purified," located at <http://www.ebioscience.com/mouse-cd115-antibody-purified-afs98.htm>, last visited on Nov. 19, 2014, one page.
Denardo, D.G. et al. (Jun. 2011). "Leukocyte complexity predicts breast cancer survival and functionally regulates response to chemotherapy," *Cancer Discov.* 1(1):52-65.
Flick, M.B. et al. (1997). "Recognition of activated CSF-1 receptor in breast carcinomas by a tyrosine 723 phosphospecific antibody," *Oncogene* 14(21):2553-2561.
Haran-Ghera, N. et al. (1997). "Increased circulating colony-stimulating factor-1 (CSF-1) in SJL/J mice with radiation-induced acute

(56) References Cited

OTHER PUBLICATIONS myeloid leukemia (AML) is associated with autocrine regulation of AML cells by CSF-1," *Blood* 89(7):2537-2545.

Hayashi, S. et al. (1997). "Osteoclast precursors in bone marrow and peritoneal cavity," *J. Cell Physiol.* 170(3):241-247 (Abstract Only).

Ide, H. et al. (2002). "Expression of colony-stimulating factor 1 receptor during prostate development and prostate cancer progression," *PNAS* 99(22):14404-14409.

International Search Report mailed on Nov. 18, 2014, for PCT Patent Application No. PCT/EP2014/069451, filed on Sep. 11, 2014, seven pages.

International Search Report mailed on Sep. 1, 2011, for PCT Patent Application No. PCT/EP2011/053213, filed on Mar. 3, 2011, six pages.

International Search Report mailed on Sep. 1, 2014, for PCT Patent Application No. PCT/EP2014/057909, filed on Apr. 17, 2014, six pages.

Jose, M.D. et al. (2003). "Blockade of macrophage colony-stimulating factor reduces macrophage proliferation and accumulation in renal allograft rejection," *American Journal of Transplantation* 3(3):294-300.

Kacinski, B.M. et al. (1990). "Ovarian adenocarcinomas express fms-complementary transcripts and fms antigen, often with coexpression of CSF-1," *Am. J. Pathol.* 137(1):135-147.

Kawakami, Y. et al. (2000). "Macrophage-colony stimulating factor inhibits the growth of human ovarian cancer cells in vitro," *Eur. J. Cancer* 36(15):1991-1997.

Kommoss, F. et al. (1994). "Co-expression of M-CSF transcripts and protein, FMS (M-CSF receptor) transcripts and protein, and steroid receptor content in adenocarcinomas of the ovary," Journal of Pathology 174(2):111-119.

Mancino, A.T. et al. (2001). "Breast cancer increases osteoclastogenesis by secreting M-CSF and upregulating RANKL in stromal cells," *Journal of Surgical Research* 100(1):18-24.

Shadduck, R.K. et al. (1996). "Paradoxical stimulation of normal and leukemic rat hematopoiesis by monoclonal antibody to CSF-1 receptor," *Experimental Hematology* 24(2):314-317.

Stanley et al., "CSF-1—a mononuclear phagocyte lineage-specific hemopoietic growth factor" J Cell Biochem. 21(2):151-9 (1983).

Taylor, J.R. et al. (2005). "FMS receptor for M-CSF (CSF-1) is sensitive to the kinase inhibitor imatinib and mutation of Asp-802 to Val confers resistance," *Oncogene*, pp. 1-5.

Weir, E.C. et al. (1996). "Colony stimulating factor-1 plays a role in osteoclast formation and function in bone resorption induced by parathyroid hormone and parathyroid hormone-related protein," *Journal of Bone and Mineral Research* 11(10):1474-1481.

Written Opinion of the International Searching Authority mailed on Nov. 18, 2014, for PCT Patent Application No. PCT/EP2014/069451, filed on Sep. 11, 2014, seven pages.

Written Opinion of the International Searching Authority mailed on Sep. 1, 2011, for PCT Patent Application No. PCT/EP2011/053213, filed on Mar. 3, 2011, seven pages.

PCT Patent Application No. PCT/EP2014/069451, filed Sep. 11, 2014.

U.S. Appl. No. 14/485,140, filed Sep. 12, 2014.

Dewar et al., "Macrophage colony-stimulating factor receptor c-fms is a novel target of imatinib," Blood, 105(8):3127-32, (2005).

Stanley et al., "Biology and action of colony-stimulating factor-1 ,"Mol Reprod Dev. 46(1):4-10 (1997).

\* cited by examiner

SEQUENCE LISTING

```
<160> NUMBER OF SEQ ID NOS: 95

<210> SEQ ID NO 1
<211> LENGTH: 8
<212> TYPE: PRT
<213> ORGANISM: Mus musculus

<400> SEQUENCE: 1

Asp Gln Arg Leu Tyr Phe Asp Val
1               5

<210> SEQ ID NO 2
<211> LENGTH: 16
<212> TYPE: PRT
<213> ORGANISM: Mus musculus

<400> SEQUENCE: 2

Val Ile Trp Thr Asp Gly Gly Thr Asn Tyr Asn Ser Pro Phe Met Ser
1               5                   10                  15

<210> SEQ ID NO 3
<211> LENGTH: 5
<212> TYPE: PRT
<213> ORGANISM: Mus musculus

<400> SEQUENCE: 3

Thr Tyr Asp Ile Ser
1               5

<210> SEQ ID NO 4
<211> LENGTH: 8
<212> TYPE: PRT
<213> ORGANISM: Mus musculus

<400> SEQUENCE: 4

Gly Gln Ser Phe Ser Tyr Pro Thr
1               5

<210> SEQ ID NO 5
<211> LENGTH: 7
<212> TYPE: PRT
<213> ORGANISM: Mus musculus

<400> SEQUENCE: 5

Gly Ala Ser Asn Arg Tyr Thr
1               5
```

```
<210> SEQ ID NO 6
<211> LENGTH: 11
<212> TYPE: PRT
<213> ORGANISM: Mus musculus

<400> SEQUENCE: 6

Lys Ala Ser Glu Asp Val Asn Thr Tyr Val Ser
1               5                   10

<210> SEQ ID NO 7
<211> LENGTH: 116
<212> TYPE: PRT
<213> ORGANISM: Mus musculus

<400> SEQUENCE: 7

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Tyr
            20                  25                  30

Asp Ile Ser Trp Ile Arg Gln Ser Pro Gly Lys Gly Leu Glu Trp Leu
        35                  40                  45

Gly Val Ile Trp Thr Asp Gly Gly Thr Asn Tyr Asn Ser Pro Phe Met
    50                  55                  60

Ser Arg Leu Ser Ile Arg Lys Asp Asn Ser Lys Ser Gln Val Phe Leu
65                  70                  75                  80

Lys Met Asn Arg Leu Gln Thr Asp Asp Thr Ala Ile Tyr Tyr Cys Val
                85                  90                  95

Arg Asp Gln Arg Leu Tyr Phe Asp Val Trp Gly Ala Gly Thr Thr Val
            100                 105                 110

Thr Val Ser Ser
        115

<210> SEQ ID NO 8
<211> LENGTH: 106
<212> TYPE: PRT
<213> ORGANISM: Mus musculus

<400> SEQUENCE: 8

Asn Ile Val Met Thr Gln Ser Pro Lys Ser Met Ser Met Ser Val Gly
1               5                   10                  15

Glu Arg Val Thr Leu Asn Cys Lys Ala Ser Glu Asp Val Asn Thr Tyr
            20                  25                  30

Val Ser Trp Tyr Gln Gln Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Gly Gly Ser Thr Thr Asp Phe Thr Leu Thr Ile Ser Ser Val Gln Ala
65                  70                  75                  80

Glu Asp Leu Ala Asp Tyr Phe Cys Gly Gln Ser Phe Ser Tyr Pro Thr
                85                  90                  95

Phe Gly Thr Gly Thr Lys Leu Glu Ile Lys
            100                 105

<210> SEQ ID NO 9
<211> LENGTH: 7
<212> TYPE: PRT
<213> ORGANISM: Mus musculus

<400> SEQUENCE: 9
```

```
Asp Pro Arg Leu Tyr Phe Asp
1               5

<210> SEQ ID NO 10
<211> LENGTH: 16
<212> TYPE: PRT
<213> ORGANISM: Mus musculus

<400> SEQUENCE: 10

Val Ile Trp Thr Gly Gly Gly Thr Asn Tyr Asn Ser Gly Phe Met Ser
1               5                   10                  15

<210> SEQ ID NO 11
<211> LENGTH: 5
<212> TYPE: PRT
<213> ORGANISM: Mus musculus

<400> SEQUENCE: 11

Ser Phe Asp Ile Ser
1               5

<210> SEQ ID NO 12
<211> LENGTH: 8
<212> TYPE: PRT
<213> ORGANISM: Mus musculus

<400> SEQUENCE: 12

Gly Gln Thr Phe Ser Tyr Pro Thr
1               5

<210> SEQ ID NO 13
<211> LENGTH: 7
<212> TYPE: PRT
<213> ORGANISM: Mus musculus

<400> SEQUENCE: 13

Gly Ala Ser Asn Arg Tyr Thr
1               5

<210> SEQ ID NO 14
<211> LENGTH: 11
<212> TYPE: PRT
<213> ORGANISM: Mus musculus

<400> SEQUENCE: 14

Lys Ala Ser Glu Asp Val Val Thr Tyr Val Ser
1               5                   10

<210> SEQ ID NO 15
<211> LENGTH: 116
<212> TYPE: PRT
<213> ORGANISM: Mus musculus

<400> SEQUENCE: 15

Gln Val Gln Leu Lys Glu Ser Gly Pro Gly Leu Val Ala Pro Ser Lys
1               5                   10                  15

Ser Leu Ser Ile Thr Cys Thr Val Ser Gly Ser Ser Leu Asp Ser Phe
                20                  25                  30

Asp Ile Ser Trp Ile Arg Gln Ser Pro Gly Lys Gly Leu Glu Trp Leu
            35                  40                  45

Gly Val Ile Trp Thr Gly Gly Gly Thr Asn Tyr Asn Ser Gly Phe Met
        50                  55                  60

Ser Arg Leu Arg Ile Thr Lys Asp Asn Ser Lys Ser Gln Val Leu Leu
```

```
                65                  70                  75                  80
Lys Met Asn Ser Leu Gln Ser Asp Asp Thr Ala Ile Tyr Tyr Cys Val
                        85                  90                  95

Arg Asp Pro Arg Leu Tyr Phe Asp Val Trp Gly Ala Gly Thr Thr Val
                100                 105                 110

Thr Val Ser Ser
            115

<210> SEQ ID NO 16
<211> LENGTH: 106
<212> TYPE: PRT
<213> ORGANISM: Mus musculus

<400> SEQUENCE: 16

Asn Ile Val Met Thr Gln Ser Pro Lys Ser Met Ser Met Ser Val Gly
1               5                   10                  15

Glu Arg Val Thr Leu Ser Cys Lys Ala Ser Glu Asp Val Val Thr Tyr
                20                  25                  30

Val Ser Trp Tyr Gln Gln Lys Pro Asp Gln Ser Pro Lys Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Val Gln Ala
65                  70                  75                  80

Glu Asp Leu Ala Asp Tyr Tyr Cys Gly Gln Thr Phe Ser Tyr Pro Thr
                85                  90                  95

Phe Gly Thr Gly Thr Lys Leu Glu Ile Lys
            100                 105

<210> SEQ ID NO 17
<211> LENGTH: 8
<212> TYPE: PRT
<213> ORGANISM: Artificial
<220> FEATURE:
<223> OTHER INFORMATION: heavy chain CDR3, hMab 2F11-c11

<400> SEQUENCE: 17

Asp Gln Arg Leu Tyr Phe Asp Val
1               5

<210> SEQ ID NO 18
<211> LENGTH: 16
<212> TYPE: PRT
<213> ORGANISM: Artificial
<220> FEATURE:
<223> OTHER INFORMATION: heavy chain CDR2, hMab 2F11-c11

<400> SEQUENCE: 18

Val Ile Trp Thr Asp Gly Gly Thr Asn Tyr Asn Ser Pro Phe Met Ser
1               5                   10                  15

<210> SEQ ID NO 19
<211> LENGTH: 5
<212> TYPE: PRT
<213> ORGANISM: Artificial
<220> FEATURE:
<223> OTHER INFORMATION: heavy chain CDR1, hMab 2F11-c11

<400> SEQUENCE: 19

Thr Tyr Asp Ile Ser
1               5
```

```
<210> SEQ ID NO 20
<211> LENGTH: 8
<212> TYPE: PRT
<213> ORGANISM: Artificial
<220> FEATURE:
<223> OTHER INFORMATION: light chain CDR3, hMab 2F11-c11

<400> SEQUENCE: 20

Gly Gln Ser Phe Ser Tyr Pro Thr
1               5

<210> SEQ ID NO 21
<211> LENGTH: 7
<212> TYPE: PRT
<213> ORGANISM: Artificial
<220> FEATURE:
<223> OTHER INFORMATION: light chain CDR2, hMab 2F11-c11

<400> SEQUENCE: 21

Gly Ala Ser Asn Arg Tyr Thr
1               5

<210> SEQ ID NO 22
<211> LENGTH: 11
<212> TYPE: PRT
<213> ORGANISM: Artificial
<220> FEATURE:
<223> OTHER INFORMATION: light chain CDR1, hMab 2F11-c11

<400> SEQUENCE: 22

Arg Ala Ser Glu Asp Val Asn Thr Tyr Val Ser
1               5                   10

<210> SEQ ID NO 23
<211> LENGTH: 116
<212> TYPE: PRT
<213> ORGANISM: Artificial
<220> FEATURE:
<223> OTHER INFORMATION: heavy chain variable domain, hMab 2F11-c11

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Thr Tyr
            20                  25                  30

Asp Ile Ser Trp Ile Arg Gln Ala Pro Gly Gln Gly Leu Glu Trp Met
        35                  40                  45

Gly Val Ile Trp Thr Asp Gly Gly Thr Asn Tyr Asn Ser Pro Phe Met
    50                  55                  60

Ser Arg Val Thr Ile Thr Lys Asp Glu Ser Thr Ser Thr Ala Tyr Met
65                  70                  75                  80

Glu Leu Ser Ser Leu Arg Ser Glu Asp Thr Ala Val Tyr Tyr Cys Val
                85                  90                  95

Arg Asp Gln Arg Leu Tyr Phe Asp Val Trp Gly Gln Gly Thr Thr Val
            100                 105                 110

Thr Val Ser Ser
        115

<210> SEQ ID NO 24
<211> LENGTH: 106
<212> TYPE: PRT
<213> ORGANISM: Artificial
<220> FEATURE:
```

<223> OTHER INFORMATION: light chain variable domain, hMab 2F11-c11

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Phe Ser Tyr Pro Thr
                85                  90                  95

Phe Gly Gln Gly Thr Lys Leu Glu Ile Lys
            100                 105

<210> SEQ ID NO 25
<211> LENGTH: 8
<212> TYPE: PRT
<213> ORGANISM: Artificial
<220> FEATURE:
<223> OTHER INFORMATION: heavy chain CDR3, hMab 2F11-d8

<400> SEQUENCE: 25

Asp Gln Arg Leu Tyr Phe Asp Val
1               5

<210> SEQ ID NO 26
<211> LENGTH: 16
<212> TYPE: PRT
<213> ORGANISM: Artificial
<220> FEATURE:
<223> OTHER INFORMATION: heavy chain CDR2, hMab 2F11-d8

<400> SEQUENCE: 26

Val Ile Trp Thr Asp Gly Gly Ala Asn Tyr Ala Gln Lys Phe Gln Gly
1               5                   10                  15

<210> SEQ ID NO 27
<211> LENGTH: 5
<212> TYPE: PRT
<213> ORGANISM: Artificial
<220> FEATURE:
<223> OTHER INFORMATION: heavy chain CDR1, hMab 2F11-d8

<400> SEQUENCE: 27

Thr Tyr Asp Ile Ser
1               5

<210> SEQ ID NO 28
<211> LENGTH: 8
<212> TYPE: PRT
<213> ORGANISM: Artificial
<220> FEATURE:
<223> OTHER INFORMATION: light chain CDR3, hMab 2F11-d8

<400> SEQUENCE: 28

Gly Gln Ser Phe Ser Tyr Pro Thr
1               5

<210> SEQ ID NO 29

```
<211> LENGTH: 7
<212> TYPE: PRT
<213> ORGANISM: Artificial
<220> FEATURE:
<223> OTHER INFORMATION: light chain CDR2, hMab 2F11-d8

<400> SEQUENCE: 29

Gly Ala Ser Asn Arg Tyr Thr
1               5

<210> SEQ ID NO 30
<211> LENGTH: 11
<212> TYPE: PRT
<213> ORGANISM: Artificial
<220> FEATURE:
<223> OTHER INFORMATION: light chain CDR1, hMab 2F11-d8

<400> SEQUENCE: 30

Lys Ala Ser Glu Asp Val Asn Thr Tyr Val Ser
1               5                   10

<210> SEQ ID NO 31
<211> LENGTH: 116
<212> TYPE: PRT
<213> ORGANISM: Artificial
<220> FEATURE:
<223> OTHER INFORMATION: heavy chain variable domain, hMab 2F11-d8

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Thr Tyr
                20                  25                  30

Asp Ile Ser Trp Val Arg Gln Ala Pro Gly Gln Gly Leu Glu Trp Met
            35                  40                  45

Gly Val Ile Trp Thr Asp Gly Gly Ala Asn Tyr Ala Gln Lys Phe Gln
        50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Asp Gln Arg Leu Tyr Phe Asp Val Trp Gly Gln Gly Thr Thr Val
            100                 105                 110

Thr Val Ser Ser
        115

<210> SEQ ID NO 32
<211> LENGTH: 106
<212> TYPE: PRT
<213> ORGANISM: Artificial
<220> FEATURE:
<223> OTHER INFORMATION: light chain variable domain, hMab 2F11-d8

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asp Val Asn Thr Tyr
                20                  25                  30

Val Ser Trp Tyr Gln Gln Lys Pro Gly Lys Ala Pro Lys Leu Leu Ile
            35                  40                  45

Tyr Gly Ala Ser Asn Arg Tyr Thr Gly Val Pro Ser Arg Phe Ser Gly
        50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gly Gln Ser Phe Ser Tyr Pro Thr
                 85                  90                  95

Phe Gly Gln Gly Thr Lys Leu Glu Ile Lys
            100                 105

<210> SEQ ID NO 33
<211> LENGTH: 8
<212> TYPE: PRT
<213> ORGANISM: Artificial
<220> FEATURE:
<223> OTHER INFORMATION: heavy chain CDR3, hMab 2F11-e7

<400> SEQUENCE: 33

Asp Gln Arg Leu Tyr Phe Asp Val
1               5

<210> SEQ ID NO 34
<211> LENGTH: 16
<212> TYPE: PRT
<213> ORGANISM: Artificial
<220> FEATURE:
<223> OTHER INFORMATION: heavy chain CDR2, hMab 2F11-e7

<400> SEQUENCE: 34

Val Ile Trp Thr Asp Gly Gly Thr Asn Tyr Ala Gln Lys Leu Gln Gly
1               5                   10                  15

<210> SEQ ID NO 35
<211> LENGTH: 5
<212> TYPE: PRT
<213> ORGANISM: Artificial
<220> FEATURE:
<223> OTHER INFORMATION: heavy chain CDR1, hMab 2F11-e7

<400> SEQUENCE: 35

Ser Tyr Asp Ile Ser
1               5

<210> SEQ ID NO 36
<211> LENGTH: 8
<212> TYPE: PRT
<213> ORGANISM: Artificial
<220> FEATURE:
<223> OTHER INFORMATION: light chain CDR3, hMab 2F11-e7

<400> SEQUENCE: 36

Gln Gln Ser Phe Ser Tyr Pro Thr
1               5

<210> SEQ ID NO 37
<211> LENGTH: 7
<212> TYPE: PRT
<213> ORGANISM: Artificial
<220> FEATURE:
<223> OTHER INFORMATION: light chain CDR2, hMab 2F11-e7

<400> SEQUENCE: 37

Ala Ala Ser Asn Arg Tyr Thr
1               5

<210> SEQ ID NO 38
<211> LENGTH: 11
<212> TYPE: PRT
```

<213> ORGANISM: Artificial
<220> FEATURE:
<223> OTHER INFORMATION: light chain CDR1, hMab 2F11-e7

<400> SEQUENCE: 38

Arg Ala Ser Glu Asp Val Asn Thr Tyr Val Ser
1               5                   10

<210> SEQ ID NO 39
<211> LENGTH: 116
<212> TYPE: PRT
<213> ORGANISM: Artificial
<220> FEATURE:
<223> OTHER INFORMATION: heavy chain variable domain, hMab 2F11-e7

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Ser Trp Val Arg Gln Ala Pro Gly Gln Gly Leu Glu Trp Met
        35                  40                  45

Gly Val Ile Trp Thr Asp Gly Gly Thr Asn Tyr Ala Gln Lys Leu Gln
    50                  55                  60

Gly Arg Val Thr Met Thr Thr Asp Thr Ser Thr Ser Thr Ala Tyr Met
65                  70                  75                  80

Glu Leu Arg Ser Leu Arg Ser Asp Asp Thr Ala Val Tyr Tyr Cys Ala
                85                  90                  95

Arg Asp Gln Arg Leu Tyr Phe Asp Val Trp Gly Gln Gly Thr Thr Val
            100                 105                 110

Thr Val Ser Ser
        115

<210> SEQ ID NO 40
<211> LENGTH: 106
<212> TYPE: PRT
<213> ORGANISM: Artificial
<220> FEATURE:
<223> OTHER INFORMATION: light chain variable domain, hMab 2F11-e7

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
            20                  25                  30

Val Ser Trp Tyr Gln Gln Lys Pro Gly Lys Ala Pro Lys Leu Leu Ile
        35                  40                  45

Tyr Ala Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Tyr Pro Thr
                85                  90                  95

Phe Gly Gln Gly Thr Lys Leu Glu Ile Lys
            100                 105

<210> SEQ ID NO 41
<211> LENGTH: 8
<212> TYPE: PRT
<213> ORGANISM: Artificial

```
<220> FEATURE:
<223> OTHER INFORMATION: heavy chain CDR3, hMab 2F11-f12

<400> SEQUENCE: 41

Asp Gln Arg Leu Tyr Phe Asp Val
1               5

<210> SEQ ID NO 42
<211> LENGTH: 16
<212> TYPE: PRT
<213> ORGANISM: Artificial
<220> FEATURE:
<223> OTHER INFORMATION: heavy chain CDR2, hMab 2F11-f12

<400> SEQUENCE: 42

Val Ile Trp Thr Asp Gly Gly Thr Asn Tyr Asn Ser Pro Phe Met Ser
1               5                   10                  15

<210> SEQ ID NO 43
<211> LENGTH: 5
<212> TYPE: PRT
<213> ORGANISM: Artificial
<220> FEATURE:
<223> OTHER INFORMATION: heavy chain CDR1, hMab 2F11-f12

<400> SEQUENCE: 43

Thr Tyr Asp Ile Ser
1               5

<210> SEQ ID NO 44
<211> LENGTH: 8
<212> TYPE: PRT
<213> ORGANISM: Artificial
<220> FEATURE:
<223> OTHER INFORMATION: light chain CDR3, hMab 2F11-f12

<400> SEQUENCE: 44

Gly Gln Ser Phe Ser Tyr Pro Thr
1               5

<210> SEQ ID NO 45
<211> LENGTH: 7
<212> TYPE: PRT
<213> ORGANISM: Artificial
<220> FEATURE:
<223> OTHER INFORMATION: light chain CDR2, hMab 2F11-f12

<400> SEQUENCE: 45

Gly Ala Ser Ser Leu Gln Ser
1               5

<210> SEQ ID NO 46
<211> LENGTH: 11
<212> TYPE: PRT
<213> ORGANISM: Artificial
<220> FEATURE:
<223> OTHER INFORMATION: light chain CDR1, hMab 2F11-f12

<400> SEQUENCE: 46

Arg Ala Ser Glu Asp Val Asn Thr Tyr Val Ser
1               5                   10

<210> SEQ ID NO 47
<211> LENGTH: 116
<212> TYPE: PRT
<213> ORGANISM: Artificial
<220> FEATURE:
```

<223> OTHER INFORMATION: heavy chain variable domain, hMab 2F11-f12

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Thr Tyr
            20                  25                  30

Asp Ile Ser Trp Val Arg Gln Ala Pro Gly Gln Gly Leu Glu Trp Met
        35                  40                  45

Gly Val Ile Trp Thr Asp Gly Thr Asn Tyr Asn Ser Pro Phe Met
    50                  55                  60

Ser Arg Val Thr Ile Thr Lys Asp Glu Ser Thr Ser Thr Ala Tyr Met
65                  70                  75                  80

Glu Leu Ser Ser Leu Arg Ser Glu Asp Thr Ala Val Tyr Tyr Cys Val
                85                  90                  95

Arg Asp Gln Arg Leu Tyr Phe Asp Val Trp Gly Gln Gly Thr Thr Val
            100                 105                 110

Thr Val Ser Ser
        115

<210> SEQ ID NO 48
<211> LENGTH: 106
<212> TYPE: PRT
<213> ORGANISM: Artificial
<220> FEATURE:
<223> OTHER INFORMATION: light chain variable domain, hMab 2F11-f12

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
            20                  25                  30

Val Ser Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Phe Ser Tyr Pro Thr
                85                  90                  95

Phe Gly Gln Gly Thr Lys Leu Glu Ile Lys
            100                 105

<210> SEQ ID NO 49
<211> LENGTH: 8
<212> TYPE: PRT
<213> ORGANISM: Artificial
<220> FEATURE:
<223> OTHER INFORMATION: heavy chain CDR3, hMab 2F11-g1

<400> SEQUENCE: 49

Asp Gln Arg Leu Tyr Phe Asp Val
1               5

<210> SEQ ID NO 50
<211> LENGTH: 16
<212> TYPE: PRT
<213> ORGANISM: Artificial
<220> FEATURE:
<223> OTHER INFORMATION: heavy chain CDR2, hMab 2F11-g1

```
<400> SEQUENCE: 50

Val Ile Trp Thr Asp Gly Gly Thr Asn Tyr Asn Ser Pro Leu Lys Ser
1               5                   10                  15

<210> SEQ ID NO 51
<211> LENGTH: 5
<212> TYPE: PRT
<213> ORGANISM: Artificial
<220> FEATURE:
<223> OTHER INFORMATION: heavy chain CDR1, hMab 2F11-g1

<400> SEQUENCE: 51

Thr Tyr Asp Ile Ser
1               5

<210> SEQ ID NO 52
<211> LENGTH: 8
<212> TYPE: PRT
<213> ORGANISM: Artificial
<220> FEATURE:
<223> OTHER INFORMATION: light chain CDR3, hMab 2F11-g1

<400> SEQUENCE: 52

Gly Gln Ser Phe Ser Tyr Pro Thr
1               5

<210> SEQ ID NO 53
<211> LENGTH: 7
<212> TYPE: PRT
<213> ORGANISM: Artificial
<220> FEATURE:
<223> OTHER INFORMATION: light chain CDR2, hMab 2F11-g1

<400> SEQUENCE: 53

Gly Ala Ser Ser Arg Ala Thr
1               5

<210> SEQ ID NO 54
<211> LENGTH: 11
<212> TYPE: PRT
<213> ORGANISM: Artificial
<220> FEATURE:
<223> OTHER INFORMATION: light chain CDR1, hMab 2F11-g1

<400> SEQUENCE: 54

Arg Ala Ser Glu Asp Val Asn Thr Tyr Leu Ala
1               5                   10

<210> SEQ ID NO 55
<211> LENGTH: 116
<212> TYPE: PRT
<213> ORGANISM: Artificial
<220> FEATURE:
<223> OTHER INFORMATION: heavy chain variable domain, hMab 2F11-g1

<400> SEQUENCE: 55

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Asp Ile Ser Trp Ile Arg Gln Pro Pro Gly Lys Gly Leu Glu Trp Ile
        35                  40                  45

Gly Val Ile Trp Thr Asp Gly Gly Thr Asn Tyr Asn Ser Pro Leu Lys
    50                  55                  60
```

```
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Gln Arg Leu Tyr Phe Asp Val Trp Gly Gln Gly Thr Thr Val
            100                 105                 110

Thr Val Ser Ser
        115

<210> SEQ ID NO 56
<211> LENGTH: 106
<212> TYPE: PRT
<213> ORGANISM: Artificial
<220> FEATURE:
<223> OTHER INFORMATION: light chain variable domain, hMab 2F11-g1

<400> SEQUENCE: 56

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Glu Asp Val Asn Thr Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gly Gln Ser Phe Ser Tyr Pro Thr
                 85                  90                  95

Phe Gly Gln Gly Thr Lys Leu Glu Ile Lys
            100                 105

<210> SEQ ID NO 57
<211> LENGTH: 107
<212> TYPE: PRT
<213> ORGANISM: Homo sapiens

<400> SEQUENCE: 57

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 58
<211> LENGTH: 330
<212> TYPE: PRT
<213> ORGANISM: Homo sapiens
```

```
<400> SEQUENCE: 58

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 59
<211> LENGTH: 330
<212> TYPE: PRT
<213> ORGANISM: Artificial
<220> FEATURE:
<223> OTHER INFORMATION: human heavy chain constant region derived
      from IgG1 mutated on L234A and L235A

<400> SEQUENCE: 59

Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 60
<211> LENGTH: 327
<212> TYPE: PRT
<213> ORGANISM: Homo sapiens

<400> SEQUENCE: 60

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

```
<210> SEQ ID NO 61
<211> LENGTH: 327
<212> TYPE: PRT
<213> ORGANISM: Artificial
<220> FEATURE:
<223> OTHER INFORMATION: human heavy chain constant region derived
      from IgG4 mutated onS228P

<400> SEQUENCE: 61
```

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys

```
                    85                  90                  95
Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 62
<211> LENGTH: 972
<212> TYPE: PRT
<213> ORGANISM: Homo sapiens

<400> SEQUENCE: 62

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125
```

```
Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Ala Leu Thr Leu Val
        195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
        515                 520                 525

Leu Leu Leu Leu Leu Leu Leu Leu Tyr Lys Tyr Lys Gln Lys Pro
530                 535                 540

Lys Tyr Gln Val Arg Trp Lys Ile Ile Glu Ser Tyr Glu Gly Asn Ser
```

-continued

```
        545                 550                 555                 560
Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
                580                 585                 590

Phe Gly Lys Val Val Glu Ala Thr Ala Phe Gly Leu Gly Lys Glu Asp
                595                 600                 605

Ala Val Leu Lys Val Ala Val Lys Met Leu Lys Ser Thr Ala His Ala
610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
                660                 665                 670

Asn Phe Leu Arg Arg Lys Ala Glu Ala Met Leu Gly Pro Ser Leu Ser
                675                 680                 685

Pro Gly Gln Asp Pro Glu Gly Gly Val Asp Tyr Lys Asn Ile His Leu
                690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
                740                 745                 750

Arg Asp Leu Leu His Phe Ser Ser Gln Val Ala Gln Gly Met Ala Phe
                755                 760                 765

Leu Ala Ser Lys Asn Cys Ile His Arg Asp Val Ala Ala Arg Asn Val
                770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
                820                 825                 830

Thr Val Gln Ser Asp Val Trp Ser Tyr Gly Ile Leu Leu Trp Glu Ile
                835                 840                 845

Phe Ser Leu Gly Leu Asn Pro Tyr Pro Gly Ile Leu Val Asn Ser Lys
850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
                900                 905                 910

Gln Ala Gln Glu Asp Arg Arg Glu Arg Asp Tyr Thr Asn Leu Pro Ser
                915                 920                 925

Ser Ser Arg Ser Gly Gly Ser Gly Ser Ser Ser Glu Leu Glu Glu
                930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970
```

<210> SEQ ID NO 63
<211> LENGTH: 972
<212> TYPE: PRT
<213> ORGANISM: Artificial
<220> FEATURE:
<223> OTHER INFORMATION: mutant CSF-1R L301S Y969F

<400> SEQUENCE: 63

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Ser Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

-continued

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
    515                 520                 525

Leu Leu Leu Leu Leu Leu Leu Leu Tyr Lys Tyr Lys Gln Lys Pro
530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
    610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
        675                 680                 685

Pro Gly Gln Asp Pro Glu Gly Gly Val Asp Tyr Lys Asn Ile His Leu
    690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
        755                 760                 765

Leu Ala Ser Lys Asn Cys Ile His Arg Asp Val Ala Ala Arg Asn Val
    770                 775                 780

```
Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
        915                 920                 925

Ser Ser Arg Ser Gly Gly Ser Gly Ser Ser Ser Glu Leu Glu Glu
930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Phe Gln Phe Cys
                965                 970

<210> SEQ ID NO 64
<211> LENGTH: 493
<212> TYPE: PRT
<213> ORGANISM: Artificial
<220> FEATURE:
<223> OTHER INFORMATION: human CSF-1R Extracellular Domain

<400> SEQUENCE: 64

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175
```

-continued

```
Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
            245                 250                 255

Tyr Ser Cys Val Ala Ser Asn Val Gln Gly Lys His Ser Thr Ser Met
        260                 265                 270

Phe Phe Arg Val Val Glu Ser Ala Tyr Leu Asn Leu Ser Ser Glu Gln
    275                 280                 285

Asn Leu Ile Gln Glu Val Thr Val Gly Glu Gly Leu Asn Leu Lys Val
290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
            325                 330                 335

Thr Lys Asp Thr Tyr Arg His Thr Phe Thr Leu Ser Leu Pro Arg Leu
        340                 345                 350

Lys Pro Ser Glu Ala Gly Arg Tyr Ser Phe Leu Ala Arg Asn Pro Gly
    355                 360                 365

Gly Trp Arg Ala Leu Thr Phe Glu Leu Thr Leu Arg Tyr Pro Pro Glu
370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
            405                 410                 415

Gly His Thr Asp Arg Cys Asp Glu Ala Gln Val Leu Gln Val Trp Asp
        420                 425                 430

Asp Pro Tyr Pro Glu Val Leu Ser Gln Glu Pro Phe His Lys Val Thr
    435                 440                 445

Val Gln Ser Leu Leu Thr Val Glu Thr Leu Glu His Asn Gln Thr Tyr
450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu
            485                 490
```

<210> SEQ ID NO 65
<211> LENGTH: 388
<212> TYPE: PRT
<213> ORGANISM: Artificial
<220> FEATURE:
<223> OTHER INFORMATION: human CSF-1R fragment delD4

<400> SEQUENCE: 65

```
Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45
```

-continued

```
Ile Leu Ser Thr Asn Asn Ala Thr Phe Gln Asn Thr Gly Thr Tyr Arg
 50                  55                  60

Cys Thr Glu Pro Gly Asp Pro Leu Gly Gly Ser Ala Ala Ile His Leu
 65                  70                  75                  80

Tyr Val Lys Asp Pro Ala Arg Pro Trp Asn Val Leu Ala Gln Glu Val
                 85                  90                  95

Val Val Phe Glu Asp Gln Asp Ala Leu Leu Pro Cys Leu Leu Thr Asp
                100                 105                 110

Pro Val Leu Glu Ala Gly Val Ser Leu Val Arg Val Arg Gly Arg Pro
                115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
                180                 185                 190

Leu Val Arg Ile Arg Gly Glu Ala Ala Gln Ile Val Cys Ser Ala Ser
                195                 200                 205

Ser Val Asp Val Asn Phe Asp Val Phe Leu Gln His Asn Asn Thr Lys
                210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
                260                 265                 270

Phe Phe Arg Tyr Pro Pro Glu Val Ser Val Ile Trp Thr Phe Ile Asn
                275                 280                 285

Gly Ser Gly Thr Leu Leu Cys Ala Ala Ser Gly Tyr Pro Gln Pro Asn
                290                 295                 300

Val Thr Trp Leu Gln Cys Ser Gly His Thr Asp Arg Cys Asp Glu Ala
305                 310                 315                 320

Gln Val Leu Gln Val Trp Asp Asp Pro Tyr Pro Glu Val Leu Ser Gln
                325                 330                 335

Glu Pro Phe His Lys Val Thr Val Gln Ser Leu Leu Thr Val Glu Thr
                340                 345                 350

Leu Glu His Asn Gln Thr Tyr Glu Cys Arg Ala His Asn Ser Val Gly
                355                 360                 365

Ser Gly Ser Trp Ala Phe Ile Pro Ile Ser Ala Gly Ala His Thr His
370                 375                 380

Pro Pro Asp Glu
385

<210> SEQ ID NO 66
<211> LENGTH: 292
<212> TYPE: PRT
<213> ORGANISM: Artificial
<220> FEATURE:
<223> OTHER INFORMATION: human CSF-1R fragment D1-D3

<400> SEQUENCE: 66

Ile Pro Val Ile Glu Pro Ser Val Pro Glu Leu Val Val Lys Pro Gly
 1               5                  10                  15
```

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln
    290

<210> SEQ ID NO 67
<211> LENGTH: 21
<212> TYPE: PRT
<213> ORGANISM: Artificial
<220> FEATURE:
<223> OTHER INFORMATION: signal peptide

<400> SEQUENCE: 67

Met Gly Ser Gly Pro Gly Val Leu Leu Leu Leu Val Ala Thr Ala
1               5                   10                  15

Trp His Gly Gln Gly
            20

<210> SEQ ID NO 68
<211> LENGTH: 36
<212> TYPE: DNA
<213> ORGANISM: Artificial
<220> FEATURE:
<223> OTHER INFORMATION: Primer

<400> SEQUENCE: 68

```
cacctccatg ttcttccggt accccccaga ggtaag                                      36
```

\<210\> SEQ ID NO 69
\<211\> LENGTH: 8
\<212\> TYPE: PRT
\<213\> ORGANISM: Mus musculus

\<400\> SEQUENCE: 69

```
Asp Leu Arg Leu Tyr Phe Asp Val
1               5
```

\<210\> SEQ ID NO 70
\<211\> LENGTH: 16
\<212\> TYPE: PRT
\<213\> ORGANISM: Mus musculus

\<400\> SEQUENCE: 70

```
Val Ile Trp Ser Gly Gly Thr Asn Tyr Asn Ser Pro Phe Met Ser
1               5                   10                  15
```

\<210\> SEQ ID NO 71
\<211\> LENGTH: 10
\<212\> TYPE: PRT
\<213\> ORGANISM: Mus musculus

\<400\> SEQUENCE: 71

```
Gly Phe Ser Leu Thr Ser Tyr Asp Ile Ser
1               5                   10
```

\<210\> SEQ ID NO 72
\<211\> LENGTH: 8
\<212\> TYPE: PRT
\<213\> ORGANISM: Mus musculus

\<400\> SEQUENCE: 72

```
Gly Gln Ser Phe Thr Tyr Pro Thr
1               5
```

\<210\> SEQ ID NO 73
\<211\> LENGTH: 7
\<212\> TYPE: PRT
\<213\> ORGANISM: Mus musculus

\<400\> SEQUENCE: 73

```
Gly Ser Ser Asn Arg Tyr Thr
1               5
```

\<210\> SEQ ID NO 74
\<211\> LENGTH: 11
\<212\> TYPE: PRT
\<213\> ORGANISM: Mus musculus

\<400\> SEQUENCE: 74

```
Lys Ala Ser Glu Asp Val Gly Thr Tyr Val Ser
1               5                   10
```

\<210\> SEQ ID NO 75
\<211\> LENGTH: 116
\<212\> TYPE: PRT
\<213\> ORGANISM: Mus musculus

\<400\> SEQUENCE: 75

```
Arg Val Gln Leu Lys Glu Ser Gly Pro Gly Leu Val Ala Pro Ser Gln
1               5                   10                  15
```

```
Ser Leu Ser Ile Thr Cys Thr Val Ser Gly Phe Ser Leu Thr Ser Tyr
             20                  25                  30

Asp Ile Ser Trp Ile Arg Gln Ser Pro Gly Lys Gly Leu Glu Trp Leu
         35                  40                  45

Gly Val Ile Trp Ser Gly Gly Gly Thr Asn Tyr Asn Ser Pro Phe Met
     50                  55                  60

Ser Arg Leu Arg Ile Ser Lys Asp Asp Ser Arg Ser Gln Val Phe Leu
65                  70                  75                  80

Lys Val Asn Arg Leu Gln Thr Asp Asp Thr Ala Ile Tyr Tyr Cys Val
                 85                  90                  95

Arg Asp Leu Arg Leu Tyr Phe Asp Val Trp Gly Ala Gly Thr Thr Val
            100                 105                 110

Thr Val Ser Ser
        115
```

<210> SEQ ID NO 76
<211> LENGTH: 106
<212> TYPE: PRT
<213> ORGANISM: Mus musculus

<400> SEQUENCE: 76

```
Lys Ile Val Met Thr Gln Ser Pro Lys Ser Met Ser Val Ser Val Gly
1               5                   10                  15

Glu Arg Val Ser Leu Ser Cys Lys Ala Ser Glu Asp Val Gly Thr Tyr
             20                  25                  30

Val Ser Trp Tyr Gln Gln Lys Pro Glu Gln Ser Pro Lys Leu Leu Ile
         35                  40                  45

Tyr Gly Ser Ser Asn Arg Tyr Thr Gly Val Pro Asp Arg Phe Thr Gly
     50                  55                  60

Ser Gly Ser Ala Thr Asp Phe Thr Leu Thr Ile Ser Ser Val Gln Ala
65                  70                  75                  80

Glu Asp Leu Ala Asp Tyr Ser Cys Gly Gln Ser Phe Thr Tyr Pro Thr
                 85                  90                  95

Phe Gly Thr Gly Thr Lys Leu Glu Ile Lys
            100                 105
```

<210> SEQ ID NO 77
<211> LENGTH: 8
<212> TYPE: PRT
<213> ORGANISM: Mus musculus

<400> SEQUENCE: 77

```
Asp Pro Arg Leu Tyr Phe Asp Val
1               5
```

<210> SEQ ID NO 78
<211> LENGTH: 16
<212> TYPE: PRT
<213> ORGANISM: Mus musculus

<400> SEQUENCE: 78

```
Val Ile Trp Thr Gly Gly Gly Thr Asn Tyr Asn Ser Gly Phe Met Ser
1               5                   10                  15
```

<210> SEQ ID NO 79
<211> LENGTH: 10
<212> TYPE: PRT
<213> ORGANISM: Mus musculus

```
<400> SEQUENCE: 79

Gly Ser Ser Leu Asp Ser Phe Asp Ile Ser
1               5                   10

<210> SEQ ID NO 80
<211> LENGTH: 8
<212> TYPE: PRT
<213> ORGANISM: Mus musculus

<400> SEQUENCE: 80

Gly Gln Thr Phe Ser Tyr Pro Thr
1               5

<210> SEQ ID NO 81
<211> LENGTH: 7
<212> TYPE: PRT
<213> ORGANISM: Mus musculus

<400> SEQUENCE: 81

Gly Ala Ser Asn Arg Tyr Thr
1               5

<210> SEQ ID NO 82
<211> LENGTH: 11
<212> TYPE: PRT
<213> ORGANISM: Mus musculus

<400> SEQUENCE: 82

Lys Ala Ser Glu Asp Val Val Thr Tyr Val Ser
1               5                   10

<210> SEQ ID NO 83
<211> LENGTH: 116
<212> TYPE: PRT
<213> ORGANISM: Mus musculus

<400> SEQUENCE: 83

Gln Val Gln Leu Lys Glu Ser Gly Pro Gly Leu Val Ala Pro Ser Lys
1               5                   10                  15

Ser Leu Ser Ile Thr Cys Thr Val Ser Gly Ser Ser Leu Asp Ser Phe
            20                  25                  30

Asp Ile Ser Trp Ile Arg Gln Pro Pro Gly Lys Gly Leu Glu Trp Leu
        35                  40                  45

Gly Val Ile Trp Thr Gly Gly Thr Asn Tyr Asn Ser Gly Phe Met
    50                  55                  60

Ser Arg Leu Arg Ile Ser Lys Asp Asn Ser Lys Ser Gln Val Phe Leu
65                  70                  75                  80

Lys Met Ser Ser Leu Gln Ser Asp Asp Thr Ala Ile Tyr Tyr Cys Val
                85                  90                  95

Arg Asp Pro Arg Leu Tyr Phe Asp Val Trp Gly Ala Gly Thr Thr Val
            100                 105                 110

Thr Val Ser Ser
        115

<210> SEQ ID NO 84
<211> LENGTH: 106
<212> TYPE: PRT
<213> ORGANISM: Mus musculus

<400> SEQUENCE: 84

Asn Ile Val Met Thr Gln Ser Pro Lys Ser Met Ser Met Ser Val Gly
```

```
                1               5                  10                    15
            Glu Arg Val Thr Leu Ser Cys Lys Ala Ser Glu Asp Val Val Thr Tyr
                            20                  25                  30

Val Ser Trp Tyr Gln Gln Lys Pro Glu Gln Ser Pro Lys Leu Leu Ile
                        35                  40                  45

Tyr Gly Ala Ser Asn Arg Tyr Thr Gly Val Pro Asp Arg Phe Thr Gly
                        50                  55                  60

Ser Gly Ser Ala Thr Asp Phe Thr Leu Thr Ile Ser Ser Ile Gln Ala
            65                  70                  75                  80

Glu Asp Leu Ala Asp Tyr Tyr Cys Gly Gln Thr Phe Ser Tyr Pro Thr
                            85                  90                  95

Phe Gly Thr Gly Thr Lys Leu Glu Ile Lys
                        100                 105

<210> SEQ ID NO 85
<211> LENGTH: 218
<212> TYPE: PRT
<213> ORGANISM: Artificial
<220> FEATURE:
<223> OTHER INFORMATION: human CSF-1R fragment domains D4-D5

<400> SEQUENCE: 85

Val Val Glu Ser Ala Tyr Leu Asn Leu Ser Ser Glu Gln Asn Leu Ile
            1               5                  10                  15

Gln Glu Val Thr Val Gly Glu Gly Leu Asn Leu Lys Val Met Val Glu
                            20                  25                  30

Ala Tyr Pro Gly Leu Gln Gly Phe Asn Trp Thr Tyr Leu Gly Pro Phe
                        35                  40                  45

Ser Asp His Gln Pro Glu Pro Lys Leu Ala Asn Ala Thr Thr Lys Asp
                        50                  55                  60

Thr Tyr Arg His Thr Phe Thr Leu Ser Leu Pro Arg Leu Lys Pro Ser
            65                  70                  75                  80

Glu Ala Gly Arg Tyr Ser Phe Leu Ala Arg Asn Pro Gly Gly Trp Arg
                            85                  90                  95

Ala Leu Thr Phe Glu Leu Thr Leu Arg Tyr Pro Pro Glu Val Ser Val
                        100                 105                 110

Ile Trp Thr Phe Ile Asn Gly Ser Gly Thr Leu Leu Cys Ala Ala Ser
                        115                 120                 125

Gly Tyr Pro Gln Pro Asn Val Thr Trp Leu Gln Cys Ser Gly His Thr
                        130                 135                 140

Asp Arg Cys Asp Glu Ala Gln Val Leu Gln Val Trp Asp Asp Pro Tyr
            145                 150                 155                 160

Pro Glu Val Leu Ser Gln Glu Pro Phe His Lys Val Thr Val Gln Ser
                            165                 170                 175

Leu Leu Thr Val Glu Thr Leu Glu His Asn Gln Thr Tyr Glu Cys Arg
                        180                 185                 190

Ala His Asn Ser Val Gly Ser Gly Ser Trp Ala Phe Ile Pro Ile Ser
                        195                 200                 205

Ala Gly Ala His Thr His Pro Pro Asp Glu
                210                 215

<210> SEQ ID NO 86
<211> LENGTH: 554
<212> TYPE: PRT
<213> ORGANISM: homo sapiens

<400> SEQUENCE: 86
```

```
Met Thr Ala Pro Gly Ala Ala Arg Cys Pro Thr Thr Trp Leu
1               5                   10                  15

Gly Ser Leu Leu Leu Leu Val Cys Leu Ala Ser Arg Ser Ile Thr
            20                  25                  30

Glu Glu Val Ser Glu Tyr Cys Ser His Met Ile Gly Ser Gly His Leu
            35                  40                  45

Gln Ser Leu Gln Arg Leu Ile Asp Ser Gln Met Glu Thr Ser Cys Gln
50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
                100                 105                 110

Gln Glu Leu Ser Leu Arg Leu Lys Ser Cys Phe Thr Lys Asp Tyr Glu
            115                 120                 125

Glu His Asp Lys Ala Cys Val Arg Thr Phe Tyr Glu Thr Pro Leu Gln
            130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
            195                 200                 205

Gln Pro Leu Ala Pro Ser Met Ala Pro Val Ala Gly Leu Thr Trp Glu
210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
            275                 280                 285

Pro Gly Met Glu Asp Ile Leu Asp Ser Ala Met Gly Thr Asn Trp Val
            290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
                340                 345                 350

Ser Ala Lys Gly Gln Gln Pro Ala Asp Val Thr Gly Thr Ala Leu Pro
            355                 360                 365

Arg Val Gly Pro Val Arg Pro Thr Gly Gln Asp Trp Asn His Thr Pro
            370                 375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
                405                 410                 415
```

```
Ser Thr Leu Ser Ala Gln Pro Gln Leu Ser Arg Ser His Ser Ser Gly
                420                 425                 430

Ser Val Leu Pro Leu Gly Glu Leu Glu Gly Arg Arg Ser Thr Arg Asp
            435                 440                 445

Arg Arg Ser Pro Ala Glu Pro Glu Gly Gly Pro Ala Ser Glu Gly Ala
450                 455                 460

Ala Arg Pro Leu Pro Arg Phe Asn Ser Val Pro Leu Thr Asp Thr Gly
465                 470                 475                 480

His Glu Arg Gln Ser Glu Gly Ser Phe Ser Pro Gln Leu Gln Glu Ser
                485                 490                 495

Val Phe His Leu Leu Val Pro Ser Val Ile Leu Val Leu Leu Ala Val
            500                 505                 510

Gly Gly Leu Leu Phe Tyr Arg Trp Arg Arg Ser His Gln Glu Pro
            515                 520                 525

Gln Arg Ala Asp Ser Pro Leu Glu Gln Pro Glu Gly Ser Pro Leu Thr
        530                 535                 540

Gln Asp Asp Arg Gln Val Glu Leu Pro Val
545                 550

<210> SEQ ID NO 87
<211> LENGTH: 242
<212> TYPE: PRT
<213> ORGANISM: homo sapiens

<400> SEQUENCE: 87

Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
        35                  40                  45

Ser Arg Leu Gln Tyr Met Lys His Tyr Phe Pro Ile Asn Tyr Lys Ile
    50                  55                  60

Ser Val Pro Tyr Glu Gly Val Phe Arg Ile Ala Asn Val Thr Arg Leu
65                  70                  75                  80

Gln Arg Ala Gln Val Ser Glu Arg Glu Leu Arg Tyr Leu Trp Val Leu
                85                  90                  95

Val Ser Leu Ser Ala Thr Glu Ser Val Gln Asp Val Leu Leu Glu Gly
            100                 105                 110

His Pro Ser Trp Lys Tyr Leu Gln Glu Val Glu Thr Leu Leu Leu Asn
        115                 120                 125

Val Gln Gln Gly Leu Thr Asp Val Glu Val Ser Pro Lys Val Glu Ser
    130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
            180                 185                 190

Val Pro Ser Pro Gln Ser Cys Ser Pro Glu Pro Ser Leu Gln Tyr Ala
        195                 200                 205

Ala Thr Gln Leu Tyr Pro Pro Pro Trp Ser Pro Ser Ser Pro Pro
    210                 215                 220

His Ser Thr Gly Ser Val Arg Pro Val Arg Ala Gln Gly Glu Gly Leu
225                 230                 235                 240
```

Leu Pro

<210> SEQ ID NO 88
<211> LENGTH: 1032
<212> TYPE: PRT
<213> ORGANISM: homo sapiens

<400> SEQUENCE: 88

```
Met Gly Phe Cys Arg Ser Ala Leu His Pro Leu Ser Leu Leu Val Gln
1               5                   10                  15

Ala Ile Met Leu Ala Met Thr Leu Ala Leu Gly Thr Leu Pro Ala Phe
            20                  25                  30

Leu Pro Cys Glu Leu Gln Pro His Gly Leu Val Asn Cys Asn Trp Leu
        35                  40                  45

Phe Leu Lys Ser Val Pro His Phe Ser Met Ala Ala Pro Arg Gly Asn
    50                  55                  60

Val Thr Ser Leu Ser Leu Ser Ser Asn Arg Ile His His Leu His Asp
65                  70                  75                  80

Ser Asp Phe Ala His Leu Pro Ser Leu Arg His Leu Asn Leu Lys Trp
                85                  90                  95

Asn Cys Pro Pro Val Gly Leu Ser Pro Met His Phe Pro Cys His Met
            100                 105                 110

Thr Ile Glu Pro Ser Thr Phe Leu Ala Val Pro Thr Leu Glu Glu Leu
        115                 120                 125

Asn Leu Ser Tyr Asn Asn Ile Met Thr Val Pro Ala Leu Pro Lys Ser
    130                 135                 140

Leu Ile Ser Leu Ser Leu Ser His Thr Asn Ile Leu Met Leu Asp Ser
145                 150                 155                 160

Ala Ser Leu Ala Gly Leu His Ala Leu Arg Phe Leu Phe Met Asp Gly
                165                 170                 175

Asn Cys Tyr Tyr Lys Asn Pro Cys Arg Gln Ala Leu Glu Val Ala Pro
            180                 185                 190

Gly Ala Leu Leu Gly Leu Gly Asn Leu Thr His Leu Ser Leu Lys Tyr
        195                 200                 205

Asn Asn Leu Thr Val Val Pro Arg Asn Leu Pro Ser Ser Leu Glu Tyr
    210                 215                 220

Leu Leu Leu Ser Tyr Asn Arg Ile Val Lys Leu Ala Pro Glu Asp Leu
225                 230                 235                 240

Ala Asn Leu Thr Ala Leu Arg Val Leu Asp Val Gly Gly Asn Cys Arg
                245                 250                 255

Arg Cys Asp His Ala Pro Asn Pro Cys Met Glu Cys Pro Arg His Phe
            260                 265                 270

Pro Gln Leu His Pro Asp Thr Phe Ser His Leu Ser Arg Leu Glu Gly
        275                 280                 285

Leu Val Leu Lys Asp Ser Ser Leu Ser Trp Leu Asn Ala Ser Trp Phe
    290                 295                 300

Arg Gly Leu Gly Asn Leu Arg Val Leu Asp Leu Ser Glu Asn Phe Leu
305                 310                 315                 320

Tyr Lys Cys Ile Thr Lys Thr Lys Ala Phe Gln Gly Leu Thr Gln Leu
                325                 330                 335

Arg Lys Leu Asn Leu Ser Phe Asn Tyr Gln Lys Arg Val Ser Phe Ala
            340                 345                 350

His Leu Ser Leu Ala Pro Ser Phe Gly Ser Leu Val Ala Leu Lys Glu
        355                 360                 365
```

```
Leu Asp Met His Gly Ile Phe Phe Arg Ser Leu Asp Glu Thr Thr Leu
    370                 375                 380

Arg Pro Leu Ala Arg Leu Pro Met Leu Gln Thr Leu Arg Leu Gln Met
385                 390                 395                 400

Asn Phe Ile Asn Gln Ala Gln Leu Gly Ile Phe Arg Ala Phe Pro Gly
                405                 410                 415

Leu Arg Tyr Val Asp Leu Ser Asp Asn Arg Ile Ser Gly Ala Ser Glu
            420                 425                 430

Leu Thr Ala Thr Met Gly Glu Ala Asp Gly Gly Glu Lys Val Trp Leu
            435                 440                 445

Gln Pro Gly Asp Leu Ala Pro Ala Pro Val Asp Thr Pro Ser Ser Glu
    450                 455                 460

Asp Phe Arg Pro Asn Cys Ser Thr Leu Asn Phe Thr Leu Asp Leu Ser
465                 470                 475                 480

Arg Asn Asn Leu Val Thr Val Gln Pro Glu Met Phe Ala Gln Leu Ser
                485                 490                 495

His Leu Gln Cys Leu Arg Leu Ser His Asn Cys Ile Ser Gln Ala Val
            500                 505                 510

Asn Gly Ser Gln Phe Leu Pro Leu Thr Gly Leu Gln Val Leu Asp Leu
            515                 520                 525

Ser His Asn Lys Leu Asp Leu Tyr His Glu His Ser Phe Thr Glu Leu
    530                 535                 540

Pro Arg Leu Glu Ala Leu Asp Leu Ser Tyr Asn Ser Gln Pro Phe Gly
545                 550                 555                 560

Met Gln Gly Val Gly His Asn Phe Ser Phe Val Ala His Leu Arg Thr
                565                 570                 575

Leu Arg His Leu Ser Leu Ala His Asn Asn Ile His Ser Gln Val Ser
            580                 585                 590

Gln Gln Leu Cys Ser Thr Ser Leu Arg Ala Leu Asp Phe Ser Gly Asn
            595                 600                 605

Ala Leu Gly His Met Trp Ala Glu Gly Asp Leu Tyr Leu His Phe Phe
    610                 615                 620

Gln Gly Leu Ser Gly Leu Ile Trp Leu Asp Leu Ser Gln Asn Arg Leu
625                 630                 635                 640

His Thr Leu Leu Pro Gln Thr Leu Arg Asn Leu Pro Lys Ser Leu Gln
                645                 650                 655

Val Leu Arg Leu Arg Asp Asn Tyr Leu Ala Phe Phe Lys Trp Trp Ser
            660                 665                 670

Leu His Phe Leu Pro Lys Leu Glu Val Leu Asp Leu Ala Gly Asn Gln
    675                 680                 685

Leu Lys Ala Leu Thr Asn Gly Ser Leu Pro Ala Gly Thr Arg Leu Arg
    690                 695                 700

Arg Leu Asp Val Ser Cys Asn Ser Ile Ser Phe Val Ala Pro Gly Phe
705                 710                 715                 720

Phe Ser Lys Ala Lys Glu Leu Arg Glu Leu Asn Leu Ser Ala Asn Ala
                725                 730                 735

Leu Lys Thr Val Asp His Ser Trp Phe Gly Pro Leu Ala Ser Ala Leu
            740                 745                 750

Gln Ile Leu Asp Val Ser Ala Asn Pro Leu His Cys Ala Cys Gly Ala
            755                 760                 765

Ala Phe Met Asp Phe Leu Leu Glu Val Gln Ala Ala Val Pro Gly Leu
    770                 775                 780
```

```
Pro Ser Arg Val Lys Cys Gly Ser Pro Gly Gln Leu Gln Gly Leu Ser
785                 790                 795                 800

Ile Phe Ala Gln Asp Leu Arg Leu Cys Leu Asp Glu Ala Leu Ser Trp
            805                 810                 815

Asp Cys Phe Ala Leu Ser Leu Leu Ala Val Ala Leu Gly Leu Gly Val
        820                 825                 830

Pro Met Leu His His Leu Cys Gly Trp Asp Leu Trp Tyr Cys Phe His
    835                 840                 845

Leu Cys Leu Ala Trp Leu Pro Trp Arg Gly Arg Gln Ser Gly Arg Asp
850                 855                 860

Glu Asp Ala Leu Pro Tyr Asp Ala Phe Val Val Phe Asp Lys Thr Gln
865                 870                 875                 880

Ser Ala Val Ala Asp Trp Val Tyr Asn Glu Leu Arg Gly Gln Leu Glu
                885                 890                 895

Glu Cys Arg Gly Arg Trp Ala Leu Arg Leu Cys Leu Glu Glu Arg Asp
            900                 905                 910

Trp Leu Pro Gly Lys Thr Leu Phe Glu Asn Leu Trp Ala Ser Val Tyr
        915                 920                 925

Gly Ser Arg Lys Thr Leu Phe Val Leu Ala His Thr Asp Arg Val Ser
    930                 935                 940

Gly Leu Leu Arg Ala Ser Phe Leu Leu Ala Gln Gln Arg Leu Leu Glu
945                 950                 955                 960

Asp Arg Lys Asp Val Val Val Leu Val Ile Leu Ser Pro Asp Gly Arg
                965                 970                 975

Arg Ser Arg Tyr Val Arg Leu Arg Gln Arg Leu Cys Arg Gln Ser Val
            980                 985                 990

Leu Leu Trp Pro His Gln Pro Ser  Gly Gln Arg Ser Phe Trp Ala Gln
        995                 1000                1005

Leu Gly Met Ala Leu Thr Arg  Asp Asn His His Phe  Tyr Asn Arg
    1010                1015                 1020

Asn Phe Cys Gln Gly Pro Thr  Ala Glu
    1025                1030

<210> SEQ ID NO 89
<211> LENGTH: 20
<212> TYPE: DNA
<213> ORGANISM: Artificial
<220> FEATURE:
<223> OTHER INFORMATION: unmethylated cytosine-phosphate-guanosine
      (CpG) motif containing oligodeoxynucleotide CpG ODN 2216

<400> SEQUENCE: 89 ggggacgat cgtcggggggg                                           20

<210> SEQ ID NO 90
<211> LENGTH: 19
<212> TYPE: DNA
<213> ORGANISM: Artificial
<220> FEATURE:
<223> OTHER INFORMATION: unmethylated cytosine-phosphate-guanosine
      (CpG) motif containing oligodeoxynucleotide CpG ODN PB4

<400> SEQUENCE: 90
tcggacgatc gtcggggggg                                           19

<210> SEQ ID NO 91
<211> LENGTH: 22
<212> TYPE: DNA
<213> ORGANISM: Artificial
```

```
<220> FEATURE:
<223> OTHER INFORMATION: unmethylated cytosine-phosphate-guanosine
      (CpG) motif containing oligodeoxynucleotide CpG ODN 1002

<400> SEQUENCE: 91
ggggtcgttc gtcgttgggg gg                                            22

<210> SEQ ID NO 92
<211> LENGTH: 24
<212> TYPE: DNA
<213> ORGANISM: Artificial
<220> FEATURE:
<223> OTHER INFORMATION: unmethylated cytosine-phosphate-guanosine
      (CpG) motif containing oligodeoxynucleotide CpG-7909 (Agatolimod)

<400> SEQUENCE: 92
tcgtcgtttt gtcgttttgt cgtt                                          24

<210> SEQ ID NO 93
<211> LENGTH: 21
<212> TYPE: DNA
<213> ORGANISM: Artificial
<220> FEATURE:
<223> OTHER INFORMATION: unmethylated cytosine-phosphate-guanosine
      (CpG) motif containing oligodeoxynucleotide CpG-685 (GNKG168)

<400> SEQUENCE: 93
tcgtcgacgt cgttcgttct c                                             21

<210> SEQ ID NO 94
<211> LENGTH: 23
<212> TYPE: DNA
<213> ORGANISM: Artificial
<220> FEATURE:
<223> OTHER INFORMATION: unmethylated cytosine-phosphate-guanosine
      (CpG) motif containing oligodeoxynucleotide CpG-684

<400> SEQUENCE: 94
tcgacgttcg tcgttcgtcg ttc                                           23

<210> SEQ ID NO 95
<211> LENGTH: 26
<212> TYPE: DNA
<213> ORGANISM: Artificial
<220> FEATURE:
<223> OTHER INFORMATION: unmethylated cytosine-phosphate-guanosine
      (CpG) motif containing oligodeoxynucleotide CpG-28

<400> SEQUENCE: 95
taaacgttat aacgttatga cgtcat                                        26
```

METHOD OF TREATING CANCER BY ADMINISTERING CSF-1R ANTIBODIES AND A TLR9 AGONIST

RELATED APPLICATIONS

This application claims the benefit of European Patent Application No. 13164695.2 filed Apr. 22, 2013, the disclosure of which is hereby incorporated by reference in its entirety for all purposes.

SEQUENCE LISTING

This application contains a sequence listing submitted via EFS-Web and hereby incorporated by reference in its entirety. Said ASCII copy, created on Apr. 19, 2014 is named P5802SequenceListing.txt, and is 88,565 bytes in size.

FIELD OF THE INVENTION

The present invention relates to the combination therapy comprising antibodies against human CSF-1R and a TLR9 agonist.

BACKGROUND OF THE INVENTION

CSF-1R and CSF-1R Antibodies

The human CSF-1 receptor (CSF-1R; colony stimulating factor 1 receptor; synonyms: M-CSF receptor; Macrophage colony-stimulating factor 1 receptor, Fms proto-oncogene, c-fms, SEQ ID NO: 62) is known since 1986 (Coussens, L., et al., Nature 320 (1986) 277-280). CSF-1R is a growth factor and encoded by the c-fms proto-oncogene (reviewed e.g. in Roth, P., and Stanley, E. R., Curr. Top. Microbiol. Immunol 181 (1992) 141-167).

CSF-1R is the receptor for CSF-1 (colony stimulating factor 1, also called M-CSF, macrophage colony-stimulating factor) and mediates the biological effects of this cytokine (Sherr, C. J., et al., Cell 41 (1985) 665-676). The cloning of the colony stimulating factor-1 receptor (CSF-1R) (also called c-fms) was described for the first time in Roussel, M. F., et al., Nature 325 (1987) 549-552. In that publication, it was shown that CSF-1R had transforming potential dependent on changes in the C-terminal tail of the protein including the loss of the inhibitory tyrosine 969 phosphorylation which binds Cbl and thereby regulates receptor down regulation (Lee, P. S., et al., Embo J. 18 (1999) 3616-3628). Recently a second ligand for CSF-1R termed interleukin-34 (IL-34) was identified (Lin, H., et al, Science 320 (2008) 807-811).

Currently two CSF-1R ligands that bind to the extracellular domain of CSF-1R are known. The first one is CSF-1 (colony stimulating factor 1, also called M-CSF, macrophage; SEQ ID NO: 86) and is found extracellularly as a disulfide-linked homodimer (Stanley, E. R. et al., Journal of Cellular Biochemistry 21 (1983) 151-159; Stanley, E. R. et al., Stem Cells 12 Suppl. 1 (1995) 15-24). The second one is IL-34 (Human IL-34; SEQ ID NO: 87) (Hume, D. A., et al, Blood 119 (2012) 1810-1820). The main biological effects of CSF-1R signaling are the differentiation, proliferation, migration, and survival of hematopoietic precursor cells to the macrophage lineage (including osteoclast). Activation of CSF-1R is mediated by its CSF-1R ligands, CSF-1 (M-CSF) and IL-34. Binding of CSF-1 (M-CSF) to CSF-1R induces the formation of homodimers and activation of the kinase by tyrosine phosphorylation (Li, W. et al, EMBO Journal. 10 (1991) 277-288; Stanley, E. R., et al., Mol. Reprod. Dev. 46 (1997) 4-10).

The biologically active homodimer CSF-1 binds to the CSF-1R within the subdomains D1 to D3 of the extracellular domain of the CSF-1 receptor (CSF-1R-ECD). The CSF-1R-ECD comprises five immunoglobulin-like subdomains (designated D1 to D5). The subdomains D4 to D5 of the extracellular domain (CSF-1R-ECD) are not involved in the CSF-1 binding (Wang, Z., et al Molecular and Cellular Biology 13 (1993) 5348-5359). The subdomain D4 is involved in dimerization (Yeung, Y-G., et al Molecular & Cellular Proteomics 2 (2003) 1143-1155; Pixley, F. J., et al., Trends Cell Biol 14 (2004) 628-638).

Further signaling is mediated by the p85 subunit of PI3K and Grb2 connecting to the PI3K/AKT and Ras/MAPK pathways, respectively. These two important signaling pathways can regulate proliferation, survival and apoptosis. Other signaling molecules that bind the phosphorylated intracellular domain of CSF-1R include STAT1, STAT3, PLCy, and Cbl (Bourette, R. P. and Rohrschneider, L. R., Growth Factors 17 (2000) 155-166).

CSF-1R signaling has a physiological role in immune responses, in bone remodeling and in the reproductive system. The knockout animals for either CSF-1 (Pollard, J. W., Mol. Reprod. Dev. 46 (1997) 54-61) or CSF-1R (Dai, X. M., et al., Blood 99 (2002) 111-120) have been shown to have osteopetrotic, hematopoietic, tissue macrophage, and reproductive phenotypes consistent with a role for CSF-1R in the respective cell types.

Sherr, C. J., et al., Blood 73 (1989) 1786-1793 relates to some antibodies against CSF-1R that inhibit the CSF-1 activity. Ashmun, R. A., et al., Blood 73 (1989) 827-837 relates to CSF-1R antibodies. Lenda, D., et al., Journal of Immunology 170 (2003) 3254-3262 relates to reduced macrophage recruitment, proliferation, and activation in CSF-1-deficient mice results in decreased tubular apoptosis during renal inflammation. Kitaura, H., et al., Journal of Dental Research 87 (2008) 396-400 refers to an anti-CSF-1 antibody which inhibits orthodontic tooth movement. WO 2001/030381 mentions CSF-1 activity inhibitors including antisense nucleotides and antibodies while disclosing only CSF-1 antisense nucleotides. WO 2004/045532 relates to metastases and bone loss prevention and treatment of metastatic cancer by a CSF-1 antagonist disclosing as antagonist anti-CSF-1-antibodies only. WO 2005/046657 relates to the treatment of inflammatory bowel disease by anti-CSF-1-antibodies. US 2002/0141994 relates to inhibitors of colony stimulating factors. WO 2006/096489 relates to the treatment of rheumatoid arthritis by anti-CSF-1-antibodies. WO 2009/026303 and WO 2009/112245 relate to certain anti-CSF-1R antibodies binding to CSF-1R within the first three subdomains (D1 to D3) of the Extracellular Domain (CSF-1R-ECD). WO2011/123381(A1) relates to antibodies against CSF-1R. WO2011/070024 relate to certain anti-CSF-1R antibodies binding to CSF-1R within the dimerization domain (D4 to D5).

TLRs, TLR9 and TLR9 Agonists

Different experimental Toll-like receptor agonists for cancer therapy are described (Galluzzi et al., OncoImmunology, 1:5, (2012) 699-716) Toll-like receptors (TLRs) in general are prototypic pattern recognition receptors (PRRs) best known for their ability to activate the innate immune system in response to conserved microbial components such as lipopolysaccharide and double-stranded RNA. Accumulating evidence indicates that the function of TLRs is not restricted to the elicitation of innate immune responses against invading pathogens. TLRs have indeed been shown to participate in tissue repair and injury-induced regeneration as well as in adaptive immune responses against cancer. In particular, TLR4 signaling appears to be required for the efficient processing and cross-presentation of cell-associated tumor antigens by dendritic cells, which de facto underlie optimal therapeutic responses to some anticancer drugs. Thus, TLRs constitute prominent therapeutic targets for the activation/intensification of anticancer immune responses. In line with this notion, long-used preparations such as the Coley toxin (a mixture of killed *Streptococcus pyogenes* and *Serratia marcescens* bacteria) and the *bacillus* Calmette-Guérin (BCG, an attenuated strain of *Mycobacterium bovis* originally developed as a vaccine against tuberculosis), both of which have been associated with consistent anticancer responses, potently activate TLR2 and TLR4 signaling.

According to currently accepted models, TLRs operate as homo- or hetero-dimers and are expressed either at the plasma membrane (TLRs that mainly bind proteo-lipidic MAMPs, i.e., TLR1, TLR2, TLR4, TLR5, TLR6 and TLR10) or in endosomes (TLRs that detect microbial nucleic acids, i.e., TLR3, TLR7, TLR8, TLR9). TLR10, which is the only orphan receptor among human TLRs, has also been shown to co-localize with TLR2 at phagosomes, suggesting that it may share with TLR2 the ability to bind acylated lipopeptides. Conclusive data on this issue, however, have not yet been reported. TLR11-13 are not encoded in the human genome. In mice, TLR11-13 are constitutively expressed in the central nervous system and undergo several-fold induction in response to cysticercosis. 21 TLR11 reportedly recognizes a profilin-like protein expressed by *Toxoplasma gondii* and has been localized at the endoplasmic reticulum. TLR13 also appears to be localized intracellularly, where it would specifically detect the vesicular stomatitis virus. So far, the ligand specificity and intracellular localization of TLR12 remain unexplored.

So in summary the different Toll-like receptors have different functions, structure and expression patterns. Consequently also their ligands and agonist have different functions and mode of action. E.g. LPS, the natural ligand of TLR2 and TLR4 also known as endotoxin, has anticancer properties which have been discovered as early as in the 1960s, when the existence of TLRs was not even suspected.

TLR9 is mainly found in the endosomal compartment of B cells, monocytes, macrophages and plasmacytoid Dendritic Cells DCs (Galluzzi et al., OncoImmunology, 1:5, (2012) 699-716). The main ligand of TLR9 is bacterial/viral DNA, differing from its mammalian counterpart for the elevated frequency of unmethylated CpG oligodeoxynucleotides. Indeed, whereas mammalian DNA has no immunostimulatory activity, the administration of bacterial/viral DNA induces a potent Th1 immune response in vivo, which is entirely abrogated in TLR9$^{-/-}$ mice. CpG oligodeoxynucleotides (or CpG ODN) are short single-stranded synthetic DNA molecules that contain a cytidine triphosphate deoxynucleotide ("C") followed by a guanidine triphosphate deoxynucleotide ("G"). The "p" refers to the phosphodiester link between consecutive nucleotides, although some ODN have a modified phosphorothioate (PS) backbone instead. When these CpG motifs are unmethylated, they act as immunostimulants (Weiner, G J; et al, PNAS 94 (1997) 10833-7).

CpG motifs are considered pathogen-associated molecular patterns (PAMPs) due to their abundance in microbial genomes but their rarity in vertebrate genomes (Bauer, S; Current Topics in Microbiology and Immunology 270 (2002) 145-54). The CpG PAMP is recognized by the pattern recognition receptor (PRR) Toll-Like Receptor 9 (TLR9), which is constitutively expressed only in B cells and plasmacytoid dendritic cells (pDCs) in humans and other higher primates (Rothenfusser, S; et al, Human immunology 63 (2002) 1111-9)

Synthetic CpG ODN differ from microbial DNA in that they have a partially or completely phosphorothioated (PS) backbone instead of the typical phosphodiester backbone and a poly G tail at the 3' end, 5' end, or both. PS modification protects the ODN from being degraded by nucleases such as DNase in the body and poly G tail enhances cellular uptake (Dalpke, A H et al, Immunology 106 (2002) 102-12). The poly G tails form intermolecular tetrads that result in high molecular weight aggregates. These aggregates are responsible for the increased activity the poly G sequence impart; not the sequence itself.

These synthetic oligodeoxynucleotides containing unmethylated CpG motifs (CpG ODNs), such as ODN 1826, have been extensively studied as adjuvants (Steinhagen F. et al., 2011; Vaccine 29(17):3341-55). These CpG motifs are present at a 20-fold greater frequency in bacterial DNA compared to mammalian DNA (Hemmi H. et al., 2000. Nature 408: 740-5). CpG ODNs agonize TLR9, which is expressed on human B cells and plasmacytoid dendritic cells (pDCs), thereby inducing Th1-dominated immune responses (Coffman et al., 2010. Immunity 33(4):492-503). Pre-clinical studies, conducted in rodents and non-human primates, and human clinical trials have demonstrated that CpG ODNs can significantly improve vaccine-specific antibody responses (Steinhagen F. et al., 2011; Vaccine 29(17):3341-55).

Numerous sequences have been shown to stimulate TLR9 with variations in the number and location of CpG dimers, as well as the precise base sequences flanking the CpG dimers. This led to the creation of classes or categories of CpG ODN, which are all TLR9 agonist based on their sequence, secondary structures, and effect on human peripheral blood mononuclear cells (PBMCs). The three main classes of CpG ODNs are class A, B and C, which differ in their immune-stimulatory activities (Krug A. et al., 2001, Eur J Immunol, 31(7): 2154-63). Furthermore, CpG ODNs activate TLR9 in a species-specific manner (Bauer, S. et al., 2001, PNAS, 98(16): 9237-42). One of the first Class A ODN, ODN 2216, was described in 2001 by Krug et al (see above) This class of ODN was distinctly different from the previously described Class B ODN (i.e., ODN 2006) in that it stimulated the production of large amounts of Type I interferons, the most important one being IFNα, and induced the maturation of pDCs.

Class A ODN are also strong activators of NK cells through indirect cytokine signaling. Class A ODN typically contain 7 to 10 PS-modified bases at one or both ends that resist degradation by nucleases and increase the longevity of the ODN. The above rules strictly define the class, but variability of the sequence within these "rules" is possible. It should also be noted that changes to the sequence will affect the magnitude of the response. For example, the internal palindrome sequence can be 4 to 8 base pairs in length and vary in the order of bases, however the pattern, 5'-Pu Pu CG Pu Py CG Py Py-3', was found to be the most active when compared to several other sequences. The poly G tail found at either end of the DNA strand can vary in length and even number, but its presence is critical to the activity of the molecule.

Class B ODN (i.e. ODN 2007) are strong stimulators of human B cell and monocyte maturation. They also stimulate the maturation of pDC but to a lesser extent than Class A ODN and very small amounts of IFNα. The strongest ODN in this class have three 6mer sequences. Class B ODNs have been studied extensively as therapeutic agents because of their ability to induce a strong humoral immune response, making them ideal as a vaccine adjuvant.

ODN 1826 is a type B CpG ODN specific for mouse TLR9. Type B CpG ODNs contain a full phosphorothioate backbone with one or more CpG dinucleotides and can strongly activate B cells (Krug A. et al., 2001, Eur J Immunol, 31(7): 2154-63). ODN 1826, a mouse-reactive surrogate TLR9-agonist has been tested as an adjuvant in numerous animal models (Bauer, S. et al., 2001, PNAS, 98(16):9237-42). Research in mice demonstrated that ODN 1826 administration can induce the activation of antigen presenting cells and type I IFN anti-viral activity 8-9, indicative of a Th1 immune response (Longhi Mp. et al., 2009, J Exp Med 206: 1589-602).

Moreover, the administration of type B CpG oligonucleotides (alone or combined with chemotherapeutics or peptide vaccines) to tumor-bearing rodents reportedly exerts potent anticancer effects. Initial Phase I/II clinical trials to test the safety and efficacy of CpG-7909 for oncological indications were launched in April 2000. Approximately in the same period, CpG-7909 begun to be extensively investigated as an adjuvant for cancer-unrelated indications (mainly antiviral vaccines), showing no severe side effects and encouraging efficacy.

During the last decade, the safety and anticancer potential of CpG-7909 (as a standalone agent or in combination with chemotherapy and/or vaccination approaches) have been investigated in a large number of Phase I/II clinical trials, including studies with leukemia, lymphoma, basal cell carcinoma, 1melanoma, esophageal squamous cell carcinoma, NSCLC, renal cell carcinoma, and prostate cancer patients. Several TLR9 agonist are known and currently developed in clinical testing Agatolimod (tricosasodium salt of a synthetic 24-mer oligonucleotide containing 3 CpG motifs; Pfizer) GNKG168 (CpG ODN; SBI Biotech), IMO-2055 (synthetic oligonucleotide containing unmethylated CpG dinucleotides; Idera Pharmaceuticals), MGN-1703 (Mologen). Typically these TLR9 agonist are used in the treatment of different cancers:

Schroder K et al, (J Leukoc Biol. 81(6) (2007) 1577-90 relates to TLR agonist (unmethylated CpG-containing DNA (CpG DNA)) the regulation of mouse Tlr9 expression and defines a molecular mechanism by which IFN-gamma amplifies mouse macrophage responses to CpG DNA.

SUMMARY OF THE INVENTION

The invention comprises the combination therapy of an antibody binding to human CSF-1R (including antibodies binding to domains D1-D3 and antibodies binding to domains D4-D5, preferably antibodies binding to domains D4-D5 as described herein) with a Toll-like receptor 9 (TLR9) agonist for use in the treatment of cancer.

One embodiment is an antibody which binds to human CSF-1R characterized in binding to the (dimerization) domains D4 to D5 (SEQ ID No: 85) of the extracellular domain of human CSF-1R for use in
  a) the inhibition of cell proliferation in CSF-1R ligand-dependent and/or CSF-1 ligand-independent CSF-1R expressing tumor cells;
  b) the inhibition of cell proliferation of tumors with CSF-1R ligand-dependent and/or CSF-1R ligand-independent CSF-1R expressing macrophage infiltrate;
  c) the inhibition of cell survival (in CSF-1R ligand-dependant and/or CSF-1R ligand-independent) CSF-1R expressing monocytes and macrophages; and/or
  d) the inhibition of cell differentiation (in CSF-1R ligand-dependent and/or CSF-1R ligand-independent) CSF-1R expressing monocytes into macrophages,
wherein the anti-CSF-1R antibody is administered in combination with TLR9 agonist.

In one embodiment the TLR9 agonist is characterized by induction of IFN-alpha, IL-6, and/or IL-12 (elevating the levels of IFN-alpha, IL-6, and/or IL-12) in plasmacytoid dendritic cells (pDCs). In one embodiment the TLR9 agonist is characterized by elevating the level of IFN-alpha in human plasmacytoid dendritic cells (pDCs) (as measured by sandwich ELISA).

In one embodiment of the invention the TLR9 agonist of the invention is a oligodeoxynucleotides containing a) cytosine-phosphate-guanosine (CpG) motifs (CpG ODNs) b) pyrimidine-phosphate-guanosine (YpG) motifs (YpG ODNs) or c) cytosine-phosphate-purine (CpR) motifs (CpR ODNs).

In one embodiment of the invention the TLR9 agonist of the invention is a oligodeoxynucleotides containing cytosine-phosphate-guanosine (CpG) motifs (CpG ODNs).

CSF-1R antibodies binding to domains D1-D3 of human CSF-1R are described e.g. in WO 2009/026303 and WO 2009/112245 relate to certain anti-CSF-1R antibodies binding to CSF-1R within the first three subdomains (D1 to D3) of the Extracellular Domain (CSF-1R-ECD). WO2011/123381 (A1) relates to antibodies against CSF-1R, and Sherr, C. J., et al., Blood 73 (1989) 1786-1793 (typically these antibodies are characterized by inhibiting CSF-1R ligand-dependent but not CSF-1R ligand-independent CSF-1R proliferation and/or signaling).

CSF-1R antibodies binding to domains D4-D5 of human CSF-1R are described e.g. within the present invention, in WO2011/070024, in PCT/EP2012/075241 and Sherr, C. J., et al., Blood 73 (1989) 1786-1793 (typically these antibodies are characterized by inhibiting CSF-1R ligand-dependent and CSF-1R ligand-independent CSF-1R proliferation and/or signaling).

In one embodiment is an antibody which binds to human CSF-1R is characterized in binding to the (dimerization) domains D4 to D5 (SEQ ID No: 85) of the extracellular domain of human CSF-1R.

In one embodiment of the invention the anti-CSF-1R antibody is characterized in that the antibody binds to human CSF-1R fragment delD4 (SEQ ID NO: 65) and to human CSF-1R Extracellular Domain (SEQ ID NO: 64) with a ratio of 1:50 or lower.

In one embodiment of the invention the antibody is characterized in that the antibody does not bind to human CSF-1R fragment delD4 (SEQ ID NO: 65).

In one embodiment of the invention the antibody is characterized in that
  a) the heavy chain variable domain is SEQ ID NO:7 and the light chain variable domain is SEQ ID NO:8,
  b) the heavy chain variable domain is SEQ ID NO:15 and the light chain variable domain is SEQ ID NO:16;
  c) the heavy chain variable domain is SEQ ID NO:75 and the light chain variable domain is SEQ ID NO:76;
  d) the heavy chain variable domain is SEQ ID NO:83 and the light chain variable domain is SEQ ID NO:84;
or a humanized version thereof.

In one embodiment of the invention the antibody is characterized in that
  a) the heavy chain variable domain is SEQ ID NO:7 and the light chain variable domain is SEQ ID NO:8,
  b) the heavy chain variable domain is SEQ ID NO:15 and the light chain variable domain is SEQ ID NO:16;
or a humanized version thereof.

In one embodiment of the invention the antibody is characterized in that
  a) the heavy chain variable domain is SEQ ID NO:23 and the light chain variable domain is SEQ ID NO:24, or
  b) the heavy chain variable domain is SEQ ID NO:31 and the light chain variable domain is SEQ ID NO:32, or c) the heavy chain variable domain is SEQ ID NO:39 and the light chain variable domain is SEQ ID NO:40, or d) the heavy chain variable domain is SEQ ID NO:47 and the light chain variable domain is SEQ ID NO:48, or e) the heavy chain variable domain is SEQ ID NO:55 and the light chain variable domain is SEQ ID NO:56.

In one embodiment of the invention the antibody is characterized in that a) the heavy chain variable domain comprises a CDR3 region of SEQ ID NO: 1, a CDR2 region of SEQ ID NO: 2, and a CDR1 region of SEQ ID NO:3, and the light chain variable domain comprises a CDR3 region of SEQ ID NO: 4, a CDR2 region of SEQ ID NO:5, and a CDR1 region of SEQ ID NO:6, or b) the heavy chain variable domain comprises a CDR3 region of SEQ ID NO: 9, a CDR2 region of SEQ ID NO: 10, and a CDR1 region of SEQ ID NO: 11, and the light chain variable domain comprises a CDR3 region of SEQ ID NO:12, a CDR2 region of SEQ ID NO: 13, and a CDR1 region of SEQ ID NO: 14, or c) the heavy chain variable domain comprises a CDR3 region of SEQ ID NO: 17, a CDR2 region of SEQ ID NO: 18, and a CDR1 region of SEQ ID NO:19, and the light chain variable domain comprises a CDR3 region of SEQ ID NO: 20, a CDR2 region of SEQ ID NO:21, and a CDR1 region of SEQ ID NO:22, or d) the heavy chain variable domain comprises a CDR3 region of SEQ ID NO: 25, a CDR2 region of SEQ ID NO: 26, and a CDR1 region of SEQ ID NO: 27, and the light chain variable domain comprises a CDR3 region of SEQ ID NO:28, a CDR2 region of SEQ ID NO: 29, and a CDR1 region of SEQ ID NO: 30, or e) the heavy chain variable domain comprises a CDR3 region of SEQ ID NO: 33, a CDR2 region of SEQ ID NO: 34, and a CDR1 region of SEQ ID NO: 35, and the light chain variable domain comprises a CDR3 region of SEQ ID NO:36, a CDR2 region of SEQ ID NO: 37, and a CDR1 region of SEQ ID NO: 38, or f) the heavy chain variable domain comprises a CDR3 region of SEQ ID NO:41, a CDR2 region of SEQ ID NO: 42, and a CDR1 region of SEQ ID NO:43, and the light chain variable domain comprises a CDR3 region of SEQ ID NO: 44, a CDR2 region of SEQ ID NO:45, and a CDR1 region of SEQ ID NO:46, or g) the heavy chain variable domain comprises a CDR3 region of SEQ ID NO: 49, a CDR2 region of SEQ ID NO: 50, and a CDR1 region of SEQ ID NO: 51, and the light chain variable domain comprises a CDR3 region of SEQ ID NO:52, a CDR2 region of SEQ ID NO: 53, and a CDR1 region of SEQ ID NO: 54; or h) the heavy chain variable domain comprises a CDR3 region of SEQ ID NO:69, a CDR2 region of SEQ ID NO: 70, and a CDR1 region of SEQ ID NO:71, and the light chain variable domain comprises a CDR3 region of SEQ ID NO: 72, a CDR2 region of SEQ ID NO:73, and a CDR1 region of SEQ ID NO:74, or i) the heavy chain variable domain comprises a CDR3 region of SEQ ID NO: 77, a CDR2 region of SEQ ID NO: 78, and a CDR1 region of SEQ ID NO: 79, and the light chain variable domain comprises a CDR3 region of SEQ ID NO:80, a CDR2 region of SEQ ID NO: 81, and a CDR1 region of SEQ ID NO: 82.

One embodiment of the invention is an antibody binding to human CSF-1R, for use in the treatment of a patient having a CSF-1R expressing tumor or having a tumor with CSF-1R expressing macrophage infiltrate, wherein the tumor is characterized by an increase of CSF-1R ligand and wherein the anti-CSF-1R antibody is administered in combination with a TLR9 agonist.

In one embodiment of the invention the antibody is of human IgG1 subclass or of human IgG4 subclass.

The invention further comprises the use an of an CSF-1R antibody according to the invention for the manufacture of a medicament for treatment of a CSF-1R mediated disease in combination with a TLR9 agonist.

The invention further comprises the use an of an CSF-1R antibody according to the invention for the manufacture of a medicament for treatment of cancer in combination with a TLR9 agonist.

The invention further comprises the use an of an CSF-1R antibody according to the invention for the manufacture of a medicament for treatment of bone loss in combination with a TLR9 agonist.

The invention further comprises the use an of an CSF-1R antibody according to the invention for the manufacture of a medicament for treatment of metastasis in combination with a TLR9 agonist.

The invention further comprises the use an of an CSF-1R antibody according to the invention for the manufacture of a medicament for treatment of inflammatory diseases in combination with a TLR9 agonist.

The invention further comprises an CSF-1R antibody according to the invention for treatment of a CSF-1R mediated disease in combination with a TLR9 agonist.

The invention further comprises an CSF-1R antibody according to the invention for treatment of cancer in combination with a TLR9 agonist.

The invention further comprises an CSF-1R antibody according to the invention for treatment of bone loss in combination with a TLR9 agonist.

The invention further comprises an CSF-1R antibody according to the invention for treatment of metastasis in combination with a TLR9 agonist.

The invention further comprises an CSF-1R antibody according to the invention for treatment of inflammatory diseases in combination with a TLR9 agonist.

The combination therapies of the antibodies described herein show benefits for patients in need of a CSF-1R targeting therapy.

The antibodies according to the invention show efficient antiproliferative activity against ligand-independent and ligand-dependent proliferation and are therefore especially useful in the treatment of cancer and metastasis in combination with a TLR9 agonist.

The invention further provides a method for treating a patient suffering from cancer, comprising administering to a patient diagnosed as having such a disease (and therefore being in need of such a therapy) an effective amount of an CSF-1R antibody according to the invention in combination with a TLR-9 agonist.

The invention also provides compositions comprising an antibody which binds to human CSF-1R and a Toll-like receptor 9 (TLR9) agonist. In some embodiments, the antibody does not bind to human CSF-1R fragment delD4 (SEQ ID NO: 65). In some embodiments, the antibody comprises a) a heavy chain variable domain comprising SEQ ID NO:7 and a light chain variable domain comprising SEQ ID NO:8, b) a heavy chain variable domain comprising SEQ ID NO:15 and a light chain variable domain comprises SEQ ID NO:16; c) a heavy chain variable domain comprising SEQ ID NO:75 and a light chain variable domain comprising SEQ ID NO:76; d) a heavy chain variable domain comprising SEQ ID NO:83 and a light chain variable domain comprising SEQ ID NO:84;

e) a heavy chain variable domain comprising SEQ ID NO:23 and a light chain variable domain comprising SEQ ID NO:24, or f) a heavy chain variable domain comprising SEQ ID NO:31 and the light chain variable domain comprising SEQ ID NO:32, or g) a heavy chain variable domain comprising SEQ ID NO:39 and the light chain variable domain comprising SEQ ID NO:40, or h) a heavy chain variable domain comprising SEQ ID NO:47 and the light chain variable domain comprising SEQ ID NO:48, or i) a heavy chain variable domain comprising SEQ ID NO:55 and a light chain variable domain comprising SEQ ID NO:56. In some embodiments, the antibody comprises a) a heavy chain variable domain comprising a CDR3 region of SEQ ID NO: 1, a CDR2 region of SEQ ID NO: 2, and a CDR1 region of SEQ ID NO:3, and a light chain variable domain comprising a CDR3 region of SEQ ID NO: 4, a CDR2 region of SEQ ID NO:5, and a CDR1 region of SEQ ID NO:6, or b) a heavy chain variable domain comprising a CDR3 region of SEQ ID NO: 9, a CDR2 region of SEQ ID NO: 10, and a CDR1 region of SEQ ID NO: 11, and a light chain variable domain comprising a CDR3 region of SEQ ID NO:12, a CDR2 region of SEQ ID NO: 13, and a CDR1 region of SEQ ID NO: 14, or c) a heavy chain variable domain comprising a CDR3 region of SEQ ID NO: 17, a CDR2 region of SEQ ID NO: 18, and a CDR1 region of SEQ ID NO:19, and light chain variable domain comprising a CDR3 region of SEQ ID NO: 20, a CDR2 region of SEQ ID NO:21, and a CDR1 region of SEQ ID NO:22, or d) a heavy chain variable domain comprising a CDR3 region of SEQ ID NO: 25, a CDR2 region of SEQ ID NO: 26, and a CDR1 region of SEQ ID NO: 27, and a light chain variable domain comprising a CDR3 region of SEQ ID NO:28, a CDR2 region of SEQ ID NO: 29, and a CDR1 region of SEQ ID NO: 30, or e) a heavy chain variable domain comprising a CDR3 region of SEQ ID NO: 33, a CDR2 region of SEQ ID NO: 34, and a CDR1 region of SEQ ID NO: 35, and a light chain variable domain comprising a CDR3 region of SEQ ID NO:36, a CDR2 region of SEQ ID NO: 37, and a CDR1 region of SEQ ID NO: 38, or f) a heavy chain variable domain comprising a CDR3 region of SEQ ID NO:41, a CDR2 region of SEQ ID NO: 42, and a CDR1 region of SEQ ID NO:43, and a light chain variable domain comprising a CDR3 region of SEQ ID NO: 44, a CDR2 region of SEQ ID NO:45, and a CDR1 region of SEQ ID NO:46, or g) a heavy chain variable domain comprising a CDR3 region of SEQ ID NO: 49, a CDR2 region of SEQ ID NO: 50, and a CDR1 region of SEQ ID NO: 51, and a light chain variable domain comprising a CDR3 region of SEQ ID NO:52, a CDR2 region of SEQ ID NO: 53, and a CDR1 region of SEQ ID NO: 54; or h) a heavy chain variable domain comprising a CDR3 region of SEQ ID NO:69, a CDR2 region of SEQ ID NO: 70, and a CDR1 region of SEQ ID NO:71, and a light chain variable domain comprising a CDR3 region of SEQ ID NO: 72, a CDR2 region of SEQ ID NO:73, and a CDR1 region of SEQ ID NO:74, or i) a heavy chain variable domain comprising a CDR3 region of SEQ ID NO: 77, a CDR2 region of SEQ ID NO: 78, and a CDR1 region of SEQ ID NO: 79, and a light chain variable domain comprising a CDR3 region of SEQ ID NO:80, a CDR2 region of SEQ ID NO: 81, and a CDR1 region of SEQ ID NO: 82.

Even another embodiment of the invention provides methods of treating cancer. The methods comprise administering an effective amount of i) an antibody which binds to human CSF-1R, and ii) TLR9 agonist. In some embodiments, the cancer expresses or overexpresses CSF-1R. In some embodiments, the cancer is breast cancer, colorectal cancer, melanoma, head and neck cancer, lung cancer or prostate cancer.

Yet another embodiment of the invention provides methods of treating cancer. The methods comprise administering an effective amount of an antibody which specifically binds to the dimerization domains D4 to D5 (SEQ ID No: 85) of the extracellular domain of human CSF-1R and a TLR9 agonist, wherein a) cell proliferation in CSF-1R ligand-dependent and/or CSF-1 ligand-independent CSF-1R expressing tumor cells is inhibited; b) cell proliferation of tumors with CSF-1R ligand-dependent and/or CSF-1R ligand-independent CSF-1R expressing macrophage infiltrate is inhibited; c) cell survival (in CSF-1R ligand-dependant and/or CSF-1R ligand-independent) CSF-1R expressing monocytes and macrophages is inhibited; or d) cell differentiation (in CSF-1R ligand-dependent and/or CSF-1R ligand-independent) CSF-1R expressing monocytes into macrophages is inhibited.

Another embodiment of the invention provides methods of treating a patient having a CSF-1R expressing tumor or having a tumor with CSF-1R expressing macrophage infiltrate, wherein the tumor expresses increased levels of CSF-1R ligand. The method comprising administering an effective amount of an antibody which specifically binds to human CSF-1R and w a TLR9 agonist. In some embodiments, the TLR9 agonist induces IFN-alpha, IL-6, and/or IL-12 in plasmacytoid dendritic cells (pDCs). In some embodiments, the TLR9 agonist is an oligodeoxynucleotide containing cytosine-phosphate-guanosine (CpG) motifs (CpG ODNs). In some embodiments, the antibody specifically binds to the domains D4 to D5 (SEQ ID No: 85) of the extracellular domain of human CSF-1R. In some embodiments, the antibody does not bind to human CSF-1R fragment delD4 (SEQ ID NO: 65). In some embodiments, the antibody comprises a) a heavy chain variable domain comprising SEQ ID NO:7 and a light chain variable domain comprising SEQ ID NO:8, b) a heavy chain variable domain comprising SEQ ID NO:15 and a light chain variable domain comprising SEQ ID NO:16; c) a heavy chain variable domain comprising SEQ ID NO:75 and a light chain variable domain comprising SEQ ID NO:76; d) a heavy chain variable domain comprising SEQ ID NO:83 and a light chain variable domain comprising SEQ ID NO:84; e) a heavy chain variable domain comprising SEQ ID NO:23 and a light chain variable domain comprising SEQ ID NO:24, or f) a heavy chain variable domain comprising SEQ ID NO:31 and a light chain variable domain comprising SEQ ID NO:32, or g) a heavy chain variable domain comprising SEQ ID NO:39 and a light chain variable domain comprising SEQ ID NO:40, or h) a heavy chain variable domain comprising SEQ ID NO:47 and a light chain variable domain comprising SEQ ID NO:48, or i) a heavy chain variable domain comprising SEQ ID NO:55 and a light chain variable domain comprising SEQ ID NO:56. In some embodiments, the antibody comprises a) a heavy chain variable domain comprising a CDR3 region of SEQ ID NO: 1, a CDR2 region of SEQ ID NO: 2, and a CDR1 region of SEQ ID NO:3, and a light chain variable domain comprising a CDR3 region of SEQ ID NO: 4, a CDR2 region of SEQ ID NO:5, and a CDR1 region of SEQ ID NO:6, or b) a heavy chain variable domain comprising a CDR3 region of SEQ ID NO: 9, a CDR2 region of SEQ ID NO: 10, and a CDR1 region of SEQ ID NO: 11, and a light chain variable domain comprising a CDR3 region of SEQ ID NO:12, a CDR2 region of SEQ ID NO: 13, and a CDR1 region of SEQ ID NO: 14, or c) a heavy chain variable domain comprising a CDR3 region of SEQ ID NO: 17, a CDR2 region of SEQ ID NO: 18, and a CDR1 region of SEQ ID NO:19, and a light chain variable domain comprising a CDR3 region of SEQ ID NO: 20, a CDR2 region of SEQ ID NO:21, and a CDR1 region of SEQ ID NO:22, or d) a heavy chain variable domain comprising a CDR3 region of SEQ ID NO: 25, a CDR2 region of SEQ ID NO: 26, and a CDR1 region of SEQ ID NO: 27, and a light chain variable domain comprising a CDR3 region of SEQ ID NO:28, a CDR2 region of SEQ ID NO: 29, and a CDR1 region of SEQ ID NO: 30, or e) a heavy chain variable domain comprising a CDR3 region of SEQ ID NO: 33, a CDR2 region of SEQ ID NO: 34, and a CDR1 region of SEQ ID NO: 35, and a light chain variable domain comprising a CDR3 region of SEQ ID NO:36, a CDR2 region of SEQ ID NO: 37, and a CDR1 region of SEQ ID NO: 38, or f) a heavy chain variable domain comprising a CDR3 region of SEQ ID NO:41, a CDR2 region of SEQ ID NO: 42, and a CDR1 region of SEQ ID NO:43, and a light chain variable domain comprising a CDR3 region of SEQ ID NO: 44, a CDR2 region of SEQ ID NO:45, and a CDR1 region of SEQ ID NO:46, or g) a heavy chain variable domain comprising a CDR3 region of SEQ ID NO: 49, a CDR2 region of SEQ ID NO: 50, and a CDR1 region of SEQ ID NO: 51, and a light chain variable domain comprising a CDR3 region of SEQ ID NO:52, a CDR2 region of SEQ ID NO: 53, and a CDR1 region of SEQ ID NO: 54; or h) a heavy chain variable domain comprising a CDR3 region of SEQ ID NO:69, a CDR2 region of SEQ ID NO: 70, and a CDR1 region of SEQ ID NO:71, and a light chain variable domain comprising a CDR3 region of SEQ ID NO: 72, a CDR2 region of SEQ ID NO:73, and a CDR1 region of SEQ ID NO:74, or i) a heavy chain variable domain comprising a CDR3 region of SEQ ID NO: 77, a CDR2 region of SEQ ID NO: 78, and a CDR1 region of SEQ ID NO: 79, and a light chain variable domain comprising a CDR3 region of SEQ ID NO:80, a CDR2 region of SEQ ID NO: 81, and a CDR1 region of SEQ ID NO: 82. In some embodiment, the antibody is human IgG1 subclass or human IgG4 subclass.

Another embodiment of the invention provides methods of treating a patient having a CSF-1R expressing tumor or having a tumor with CSF-1R expressing macrophage infiltrate, wherein the tumor is characterized by an increase of CSF-1R ligand. The methods comprise administering an effective amount of an antibody which binds to human CSF-1R and a TLR9 agonist.

These and other embodiment of the invention will be described in greater detail in the detailed description that follows.

DESCRIPTION OF THE DRAWINGS

FIG. 3A: Biacore sensogram of binding of different anti-CSF-1R antibodies to immobilized human CSF-1R fragment delD4 (comprising the extracellular subdomains D1-D3 and D5) (SEQ ID NO: 65) (y-axis: binding signal in Response Units (RU), baseline=0 RU, x-axis: time in seconds (s)): While the antibodies Mab 3291 and sc 2-4A5 clearly show binding to this delD4 fragment, the antibodies according to the invention e.g. Mab 2F11, and Mab 2E10, did not bind to the CSF-1R fragment delD4. The control anti-CCR5 antibody m<CCR5>Pz03.1C5 did also not bind to the CSF-1R fragment delD4.
FIG. 3B: Biacore sensogram of binding of different anti-CSF-1R antibodies to immobilized human CSF-1R Extracellular Domain (CSF-1R-ECD) (comprising the extracellular subdomains D1-D5) (SEQ ID NO: 64) (y-axis: binding signal in Response Units (RU), baseline=0 RU, x-axis: time in seconds (s)): All antiCSF-1R antibodies show binding to CSF-1R-ECD. The control anti-CCR5 antibody m<CCR5>Pz03.1C5 did not bind to the CSF-1R-ECD.
FIG. 3C: Biacore sensogram of binding of different anti-CSF-1R antibodies to immobilized human CSF-1R fragment delD4 (comprising the extracellular subdomains D1-D3 and D5) (SEQ ID NO: 65) (y-axis: binding signal in Response Units (RU), baseline=0 RU, x-axis: time in seconds (s)): Mab 1G10, Mab 2H7 and humanized hMab 2F11-e7 did not bind to the CSF-1R fragment delD4. The control anti-CCR5 antibody m<CCR5>Pz03.1C5 did also not bind to the CSF-1R fragment delD4.
FIG. 3D: Biacore sensogram of binding of different anti-CSF-1R antibodies to immobilized human CSF-1R Extracellular Domain (CSF-1R-ECD) (comprising the extracellular subdomains D1-D5) (SEQ ID NO: 64) (y-axis: binding signal in Response Units (RU), baseline=0 RU, x-axis: time in seconds (s)): All anti-CSF-1R antibodies Mab 1G10, Mab 2H7 and humanized hMab 2F11-e7 showed binding to CSF-1RECD. The control anti-CCR5 antibody m<CCR5>Pz03.1C5 did not bind to the CSF-1RECD.
FIG. 3E: Biacore sensogram of binding of different anti-CSF-1R antibodies to immobilized human CSF-1R fragment delD4 (comprising the extracellular subdomains D1-D3 and D5) (SEQ ID NO: 65) (y-axis: binding signal in Response Units (RU), baseline=0 RU, x-axis: time in seconds (s)): All anti-CSF-1R antibodies 1.2.SM, CXIIG6, ab10676 and MAB3291 show binding to the CSF-1R fragment delD4. The control anti-CCR5 antibody m<CCR5>Pz03.1C5 did also not bind to the CSF-1R fragment delD4.
FIG. 3F: Biacore sensogram of binding of different anti-CSF-1R antibodies to immobilized human CSF-1R Extracellular Domain (CSF-1R-ECD) (comprising the extracellular subdomains D1-D5) (SEQ ID NO: 64) (y-axis: binding signal in Response Units (RU), baseline=0 RU, x-axis: time in seconds (s)):
All anti-CSF-1R antibodies 1.2.SM, CXIIG6, ab10676 and MAB3291 show binding to CSF-1R-ECD. The control anti-CCR5 antibody m<CCR5>Pz03.1C5 did not bind to the CSF-1R-ECD.

FIG. 4A: CSF-1 levels in Cynomolgous monkey after administration of 0.1 mg/kg anti-CSF-1R antibody. FIG. 4B: CSF-1 levels in Cynomolgous monkey after administration of 1 mg/kg anti-CSF-1R antibody. FIG. 4C: CSF-1 levels in Cynomolgous monkey after administration of 10 mg/kg anti-CSF-1R antibody. FIG. 4D: CSF-1 levels in Cynomolgous monkey after administration of 100 mg/kg anti-CSF-1R antibody.

FIG. 5A: Human Monocytes differentiated into macrophages with coculture of GM-CSF or CSF-1 (100 ng/ml ligand). After 6 days differentiation addition of RO7155. Cell viability was measured at day 7 of antibody treatment in a CTG Viability Assay (Cell-TiterGlo® Promega). Calculation of % cell viability: RLU signals from treated cells divided by RLU signal from untreated control without antibody, (n=4). FIG. 5B: Human Monocytes differentiated into macrophages with GM-CSF (M1) or M-CSF (M2) for 7 days. Phenotype analyzed by indirect fluorescence analysis-staining with anti CD163-PE, anti CD80-PE or anti HLA-DR/DQ/DP-Zenon-Alexa647 labeled. The number in each histogram corresponds to mean ratio fluorescence intensity (MRFI); calculated ratio between mean fluorescence intensity (MFI) of cells stained with the selected antibody (empty histogram) and of corresponding isotype control (negative control; gray filled histogram) (mean±SD; n 2≥5).

DETAILED DESCRIPTION OF THE INVENTION

Figure 1:
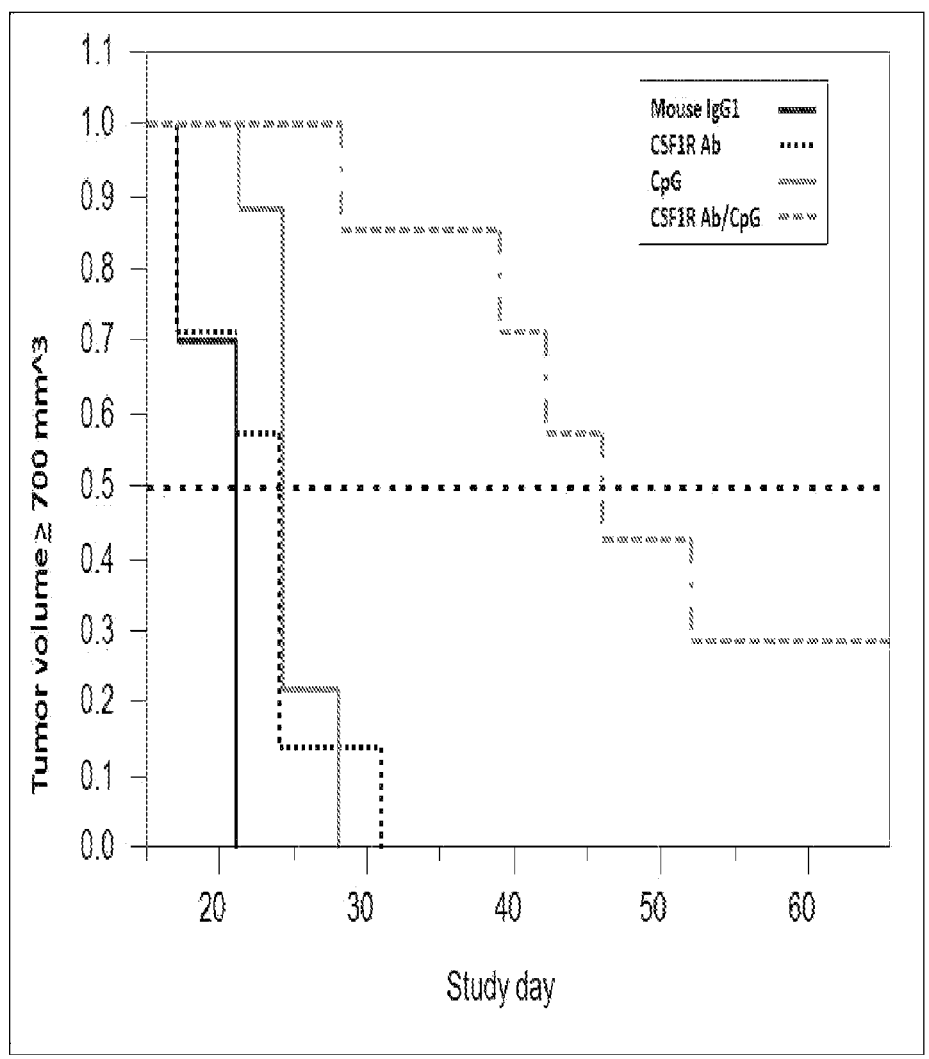
FIG. 1 illustrates data demonstrating the in vivo efficacy of a combination of a <CSF1R> antibody with a TLR9 agonist in the MC38 mouse CRC in vivo model—Median time to progression. Addition of TLR9 agonist to anti-CSF-1R antibody therapy resulted in a statistically significant more than additive improvement of median time to progression (46 days) compared to anti-CSF-1R antibody monotherapy or TLR9 agonist monotherapy.

Surprisingly it has been found that addition of TLR9 agonist to anti-CSF-1R antibody therapy resulted in a statistically significant more than additive improvement of median time to progression compared to anti-CSF-1R antibody monotherapy or TLR9 agonist monotherapy (see Example 13 and FIG. 1).

Many tumors are characterized by a prominent immune cell infiltrate, including macrophages. Initially, the immune cells were thought to be part of a defense mechanism against the tumor, but recent data support the notion that several immune cell populations including macrophages may, in fact, promote tumor progression. Macrophages are characterized by their plasticity. Depending on the cytokine microenvironment, macrophages can exhibit so-called M1 or M2-subtypes. M2 macrophages are engaged in the suppression of tumor immunity. They also play an important role in tissue repair functions such as angiogenesis and tissue remodeling which are coopted by the tumor to support growth. In contrast to tumor promoting M2 macrophages, M1 macrophages exhibit antitumor activity via the secretion of inflammatory cytokines and their engagement in antigen presentation and phagocytosis (Mantovani, A. et al., Curr. Opin. Immunol. 2 (2010) 231-237).

By secreting various cytokines such as colony stimulating factor 1 (CSF-1) and IL-10, tumor cells are able to recruit and shape macrophages into the M2-subtype, whereas cytokines such as granulocyte macrophage colony stimulating factor (GM-CSF), IFN-gamma program macrophages towards the M1 subtype. Using immunohistochemistry, it is possible to distinguish between a macrophage subpopulation co-expressing CD68 and CD163, which is likely to be enriched for M2 Macrophages, and a subset showing the CD68+/MHC II+, or CD68+/CD80+ immunophenotype, likely to include M1 macrophages. Cell shape, size, and spatial distribution of CD68 and CD163 positive macrophages is consistent with published hypotheses on a tumor-promoting role of M2 macrophages, for example by their preferential location in tumor intersecting stroma, and vital tumor areas. In contrast, CD68+/MHC class II+ macrophages are ubiquitously found. Their hypothetical role in phagocytosis is reflected by clusters of the CD68+/MHC class II+, but CD163-immunophenotype near apoptotic cells and necrotic tumor areas.

The subtype and marker expression of different macrophage subpopulations is linked with their functional state. M2 macrophages can support tumorigenesis by:

a) enhancing angiogenesis via the secretion of angiogenic factors such as VEGF or bFGF, b) supporting metastasis formation via secretion of matrix metalloproteinases (MMPs), growth factors and migratory factors guiding the tumor cells to the blood stream and setting up the metastatic niche (Wyckoff, J. et al., Cancer Res. 67 (2007) 2649-2656), c) playing a role in building an immunosuppressive milieu by secreting immunosuppressive cytokines such as IL-4, Il-13, IL-1ra and IL-10, which in turn regulate T regulatory cell function. Conversely CD4 positive T cells have been shown to enhance the activity of tumor promoting macrophages in preclinical models (Mantovani, A. et al., Eur. J. Cancer 40 (2004) 1660-1667; DeNardo, D. et al., Cancer Cell 16 (2009) 91-102).

Accordingly, in several types of cancer (e.g. breast, ovarian, Hodgkin's lymphoma) the prevalence of M2 subtype tumor associated macrophages (TAMs) has been associated with poor prognosis (Bingle, L. et al., J. Pathol. 3 (2002) 254-265; Orre, M., and Rogers, P. A., Gynecol. Oncol. 1 (1999) 47-50; Steidl, C. et al., N. Engl. J. Med. 10 (2010) 875-885). Recent data show a correlation of CD163 positive macrophage infiltrate in tumors and tumor grade (Kawamura, K. et al., Pathol. Int. 59 (2009) 300-305). TAMs isolated from patient tumors had a tolerant phenotype and were not cytotoxic to tumor cells (Mantovani, A. et al., Eur. J. Cancer 40 (2004) 1660-1667). However, infiltration of TAMs in the presence of cytotoxic T cells correlates with improved survival in non small cell lung cancer and hence reflects a more prominent M1 macrophage infiltrate in this tumor type (Kawai, O. et al., Cancer 6 (2008) 1387-1395).

Recently, a so-called immune signature comprising high numbers of macrophages and CD4 positive T cells, but low numbers of cytotoxic CD8 positive T cells was shown to correlate with reduced overall survival (OS) in breast cancer patients and to represent an independent prognostic factor (DeNardo, D. et al., Cancer Discovery 1 (2011) 54-67).

Consistent with a role for CSF-1 in driving the pro-tumorigenic function of M2 macrophages, high CSF-1 expression in rare sarcomas or locally aggressive connective tissue tumors, such as pigmented villonodular synovitis (PVNS) and tenosynovial giant cell tumor (TGCT) due in part to a translocation of the CSF-1 gene, leads to the accumulation of monocytes and macrophages expressing the receptor for CSF-1, the colony-stimulating factor 1 receptor (CSF-1R) forming the majority of the tumor mass (West, R. B. et al., Proc. Natl. Acad. Sci. USA 3 (2006) 690-695). These tumors were subsequently used to define a CSF-1 dependent macrophage signature by gene expression profiling. In breast cancer and leiomyosarcoma patient tumors this CSF-1 response gene signature predicts poor prognosis (Espinosa, I. et al., Am. J. Pathol. 6 (2009) 2347-2356; Beck, A. et al., Clin. Cancer Res. 3 (2009) 778-787).

CSF-1R belongs to the class III subfamily of receptor tyrosine kinases and is encoded by the c-fms proto-oncogene. Binding of CSF-1 or IL-34 induces receptor dimerization, followed by autophosphorylation and activation of downstream signaling cascades. Activation of CSF-1R regulates the survival, proliferation and differentiation of monocytes and macrophages (Xiong, Y. et al., J. Biol. Chem. 286 (2011) 952-960).

In addition to cells of the monocytic lineage and osteoclasts, which derive from the same hematopoetic precursor as the macrophage, CSF-1R/c-fms has also been found to be expressed by several human epithelial cancers such as ovarian and breast cancer and in leiomyosarcoma and TGCT/PVNS, albeit at lower expression levels compared to macrophages. As with TGCT/PVNS, elevated levels of CSF-1, the ligand for CSF-1R, in serum as well as ascites of ovarian cancer patients have been correlated with poor prognosis (Scholl, S. et al., Br. J. Cancer 62 (1994) 342-346; Price, F. et al., Am. J. Obstet. Gynecol. 168 (1993) 520-527). Furthermore, a constitutively active mutant form of CSF 1R is able to transform NIH3T3 cells, one of the properties of an oncogene (Chambers, S., Future Oncol 5 (2009) 1429-1440).

Preclinical models provide validation of CSF-1R as an oncology target. Blockade of CSF-1 as well as CSF-1R activity results in reduced recruitment of TAMs. Chemotherapy resulted in elevated CSF-1 expression in tumor cells leading to enhanced TAM recruitment. Blockade of CSF-1R in combination with paclitaxel resulted in activation of CD8 positive cytotoxic T cells leading to reduced tumor growth and metastatic burden in a spontaneous transgenic breast cancer model (DeNardo, D. et al., Cancer Discovery 1 (2011) 54-67).

In one embodiment the invention comprises the combination therapy of an antibody binding to human CSF-1R, characterized in that the antibody binds to human CSF-1R Extracellular Domain (SEQ ID NO: 64) in combination with a TLR9 agonist for use in the treatment of cancer.

In one embodiment the invention comprises the combination therapy of an antibody binding to human CSF-1R, characterized in that the antibody binds to human CSF-1R Extracellular Domain (SEQ ID NO: 64) (comprising domains D1 to D5) and does not bind to domains D1 to D3 (SEQ ID NO: 66) of the extracellular domain of human CSF-1R in combination with a TLR9 agonist for use in the treatment of cancer.

In one embodiment the antibody binding to human CSF-1R used in the combination therapy is characterized in that
a) the heavy chain variable domain is SEQ ID NO:7 and the light chain variable domain is SEQ ID NO:8,
b) the heavy chain variable domain is SEQ ID NO:15 and the light chain variable domain is SEQ ID NO:16;
c) the heavy chain variable domain is SEQ ID NO:75 and the light chain variable domain is SEQ ID NO:76;
d) the heavy chain variable domain is SEQ ID NO:83 and the light chain variable domain is SEQ ID NO:84;
or a humanized version thereof.

In one embodiment the antibody binding to human CSF-1R used in the combination therapy is characterized in that
a) the heavy chain variable domain is SEQ ID NO:23 and the light chain variable domain is SEQ ID NO:24, or
b) the heavy chain variable domain is SEQ ID NO:31 and the light chain variable domain is SEQ ID NO:32, or
c) the heavy chain variable domain is SEQ ID NO:39 and the light chain variable domain is SEQ ID NO:40, or
d) the heavy chain variable domain is SEQ ID NO:47 and the light chain variable domain is SEQ ID NO:48, or
e) the heavy chain variable domain is SEQ ID NO:55 and the light chain variable domain is SEQ ID NO:56.

In one embodiment the antibody binding to human CSF-1R used in the combination therapy is characterized in that
a) the heavy chain variable domain is SEQ ID NO:23 and the light chain variable domain is SEQ ID NO:24, or
b) the heavy chain variable domain is SEQ ID NO:31 and the light chain variable domain is SEQ ID NO:32, or
c) the heavy chain variable domain is SEQ ID NO:39 and the light chain variable domain is SEQ ID NO:40, or
d) the heavy chain variable domain is SEQ ID NO:47 and the light chain variable domain is SEQ ID NO:48.

In one embodiment the antibody binding to human CSF-1R used in the combination therapy is characterized in that the heavy chain variable domain is SEQ ID NO:23 and the light chain variable domain is SEQ ID NO:24.

In one embodiment the antibody binding to human CSF-1R used in the combination therapy is characterized in that the heavy chain variable domain is SEQ ID NO:31 and the light chain variable domain is SEQ ID NO:32.

In one embodiment the antibody binding to human CSF-1R used in the combination therapy is characterized in that the heavy chain variable domain is SEQ ID NO:39 and the light chain variable domain is SEQ ID NO:40.

In one embodiment the antibody binding to human CSF-1R used in the combination therapy is characterized in that the heavy chain variable domain is SEQ ID NO:47 and the light chain variable domain is SEQ ID NO:48.

In one embodiment the antibody binding to human CSF-1R used in the combination therapy is characterized in that the heavy chain variable domain is SEQ ID NO:15 and the light chain variable domain is SEQ ID NO:16, or a humanized version thereof.

In one embodiment the antibody binding to human CSF-1R used in the combination therapy is characterized in that the heavy chain variable domain is SEQ ID NO:75 and the light chain variable domain is SEQ ID NO:76; or a humanized version thereof.

In one embodiment the antibody binding to human CSF-1R used in the combination therapy is characterized in that the heavy chain variable domain is SEQ ID NO:83 and the light chain variable domain is SEQ ID NO:84; or a humanized version thereof.

In one embodiment the antibody binding to human CSF-1R used in the combination therapy is characterized in that
a) the heavy chain variable domain comprises a CDR3 region of SEQ ID NO:1, a CDR2 region of SEQ ID NO: 2, and a CDR1 region of SEQ ID NO:3, and the light chain variable domain comprises a CDR3 region of SEQ ID NO: 4, a CDR2 region of SEQ ID NO:5, and a CDR1 region of SEQ ID NO:6, or,
b) the heavy chain variable domain comprises a CDR3 region of SEQ ID NO: 9, a CDR2 region of SEQ ID NO: 10, and a CDR1 region of SEQ ID NO: 11, and the light chain variable domain comprises a CDR3 region of SEQ ID NO:12, a CDR2 region of SEQ ID NO: 13, and a CDR1 region of SEQ ID NO: 14, or
c) the heavy chain variable domain comprises a CDR3 region of SEQ ID NO: 17, a CDR2 region of SEQ ID NO: 18, and a CDR1 region of SEQ ID NO:19, and the light chain variable domain comprises a CDR3 region of SEQ ID NO: 20, a CDR2 region of SEQ ID NO:21, and a CDR1 region of SEQ ID NO:22, or
d) the heavy chain variable domain comprises a CDR3 region of SEQ ID NO: 25, a CDR2 region of SEQ ID NO: 26, and a CDR1 region of SEQ ID NO: 27, and the light chain variable domain comprises a CDR3 region of SEQ ID NO:28, a CDR2 region of SEQ ID NO: 29, and a CDR1 region of SEQ ID NO: 30, or
e) the heavy chain variable domain comprises a CDR3 region of SEQ ID NO: 33, a CDR2 region of SEQ ID NO: 34, and a CDR1 region of SEQ ID NO: 35, and the light chain variable domain comprises a CDR3 region of SEQ ID NO:36, a CDR2 region of SEQ ID NO: 37, and a CDR1 region of SEQ ID NO: 38, or
f) the heavy chain variable domain comprises a CDR3 region of SEQ ID NO:41, a CDR2 region of SEQ ID NO: 42, and a CDR1 region of SEQ ID NO:43, and the light chain variable domain comprises a CDR3 region of SEQ ID NO: 44, a CDR2 region of SEQ ID NO:45, and a CDR1 region of SEQ ID NO:46, or
g) the heavy chain variable domain comprises a CDR3 region of SEQ ID NO: 49, a CDR2 region of SEQ ID NO: 50, and a CDR1 region of SEQ ID NO: 51, and the light chain variable domain comprises a CDR3 region of SEQ ID NO:52, a CDR2 region of SEQ ID NO: 53, and a CDR1 region of SEQ ID NO: 54.

In one embodiment the antibody binding to human CSF-1R used in the combination therapy is characterized in that
- a) the heavy chain variable domain comprises a CDR3 region of SEQ ID NO:1, a CDR2 region of SEQ ID NO: 2, and a CDR1 region of SEQ ID NO:3, and the light chain variable domain comprises a CDR3 region of SEQ ID NO: 4, a CDR2 region of SEQ ID NO:5, and a CDR1 region of SEQ ID NO:6, or
- b) the heavy chain variable domain comprises a CDR3 region of SEQ ID NO: 9, a CDR2 region of SEQ ID NO: 10, and a CDR1 region of SEQ ID NO: 11, and the light chain variable domain comprises a CDR3 region of SEQ ID NO:12, a CDR2 region of SEQ ID NO: 13, and a CDR1 region of SEQ ID NO: 14, or
- c) the heavy chain variable domain comprises a CDR3 region of SEQ ID NO: 17, a CDR2 region of SEQ ID NO: 18, and a CDR1 region of SEQ ID NO:19, and the light chain variable domain comprises a CDR3 region of SEQ ID NO: 20, a CDR2 region of SEQ ID NO:21, and a CDR1 region of SEQ ID NO:22, or
- d) the heavy chain variable domain comprises a CDR3 region of SEQ ID NO: 25, a CDR2 region of SEQ ID NO: 26, and a CDR1 region of SEQ ID NO: 27, and the light chain variable domain comprises a CDR3 region of SEQ ID NO:28, a CDR2 region of SEQ ID NO: 29, and a CDR1 region of SEQ ID NO: 30, or
- e) the heavy chain variable domain comprises a CDR3 region of SEQ ID NO: 33, a CDR2 region of SEQ ID NO: 34, and a CDR1 region of SEQ ID NO: 35, and the light chain variable domain comprises a CDR3 region of SEQ ID NO:36, a CDR2 region of SEQ ID NO: 37, and a CDR1 region of SEQ ID NO: 38, or
- f) the heavy chain variable domain comprises a CDR3 region of SEQ ID NO:41, a CDR2 region of SEQ ID NO: 42, and a CDR1 region of SEQ ID NO:43, and the light chain variable domain comprises a CDR3 region of SEQ ID NO: 44, a CDR2 region of SEQ ID NO:45, and a CDR1 region of SEQ ID NO:46, or
- g) the heavy chain variable domain comprises a CDR3 region of SEQ ID NO: 49, a CDR2 region of SEQ ID NO: 50, and a CDR1 region of SEQ ID NO: 51, and the light chain variable domain comprises a CDR3 region of SEQ ID NO:52, a CDR2 region of SEQ ID NO: 53, and a CDR1 region of SEQ ID NO: 54; or
- h) the heavy chain variable domain comprises a CDR3 region of SEQ ID NO:69, a CDR2 region of SEQ ID NO: 70, and a CDR1 region of SEQ ID NO:71, and the light chain variable domain comprises a CDR3 region of SEQ ID NO: 72, a CDR2 region of SEQ ID NO:73, and a CDR1 region of SEQ ID NO:74, or
- i) the heavy chain variable domain comprises a CDR3 region of SEQ ID NO: 77, a CDR2 region of SEQ ID NO: 78, and a CDR1 region of SEQ ID NO: 79, and the light chain variable domain comprises a CDR3 region of SEQ ID NO:80, a CDR2 region of SEQ ID NO: 81, and a CDR1 region of SEQ ID NO: 82.

In one embodiment the antibody binding to human CSF-1R used in the combination therapy is characterized in that
- a) the heavy chain variable domain comprises a CDR3 region of SEQ ID NO:69, a CDR2 region of SEQ ID NO: 70, and a CDR1 region of SEQ ID NO:71, and the light chain variable domain comprises a CDR3 region of SEQ ID NO: 72, a CDR2 region of SEQ ID NO:73, and a CDR1 region of SEQ ID NO:74, or
- b) the heavy chain variable domain comprises a CDR3 region of SEQ ID NO: 77, a CDR2 region of SEQ ID NO: 78, and a CDR1 region of SEQ ID NO: 79, and the light chain variable domain comprises a CDR3 region of SEQ ID NO:80, a CDR2 region of SEQ ID NO: 81, and a CDR1 region of SEQ ID NO: 82.

In one embodiment the antibody binding to human CSF-1R used in the combination therapy is characterized in that
- a) the heavy chain variable domain comprises a CDR3 region of SEQ ID NO: 17, a CDR2 region of SEQ ID NO: 18, and a CDR1 region of SEQ ID NO:19, and the light chain variable domain comprises a CDR3 region of SEQ ID NO: 20, a CDR2 region of SEQ ID NO:21, and a CDR1 region of SEQ ID NO:22, or
- b) the heavy chain variable domain comprises a CDR3 region of SEQ ID NO: 25, a CDR2 region of SEQ ID NO: 26, and a CDR1 region of SEQ ID NO: 27, and the light chain variable domain comprises a CDR3 region of SEQ ID NO:28, a CDR2 region of SEQ ID NO: 29, and a CDR1 region of SEQ ID NO: 30, or
- c) the heavy chain variable domain comprises a CDR3 region of SEQ ID NO: 33, a CDR2 region of SEQ ID NO: 34, and a CDR1 region of SEQ ID NO: 35, and the light chain variable domain comprises a CDR3 region of SEQ ID NO:36, a CDR2 region of SEQ ID NO: 37, and a CDR1 region of SEQ ID NO: 38, or
- d) the heavy chain variable domain comprises a CDR3 region of SEQ ID NO:41, a CDR2 region of SEQ ID NO: 42, and a CDR1 region of SEQ ID NO:43, and the light chain variable domain comprises a CDR3 region of SEQ ID NO: 44, a CDR2 region of SEQ ID NO:45, and a CDR1 region of SEQ ID NO:46, or
- e) the heavy chain variable domain comprises a CDR3 region of SEQ ID NO: 49, a CDR2 region of SEQ ID NO: 50, and a CDR1 region of SEQ ID NO: 51, and the light chain variable domain comprises a CDR3 region of SEQ ID NO:52, a CDR2 region of SEQ ID NO: 53, and a CDR1 region of SEQ ID NO: 54.

In one embodiment the antibody binding to human CSF-1R used in the combination therapy is characterized in that
- a) the heavy chain variable domain comprises a CDR3 region of SEQ ID NO: 17, a CDR2 region of SEQ ID NO: 18, and a CDR1 region of SEQ ID NO:19, and the light chain variable domain comprises a CDR3 region of SEQ ID NO: 20, a CDR2 region of SEQ ID NO:21, and a CDR1 region of SEQ ID NO:22, or
- b) the heavy chain variable domain comprises a CDR3 region of SEQ ID NO: 25, a CDR2 region of SEQ ID NO: 26, and a CDR1 region of SEQ ID NO: 27, and the light chain variable domain comprises a CDR3 region of SEQ ID NO:28, a CDR2 region of SEQ ID NO: 29, and a CDR1 region of SEQ ID NO: 30, or
- c) the heavy chain variable domain comprises a CDR3 region of SEQ ID NO: 33, a CDR2 region of SEQ ID NO: 34, and a CDR1 region of SEQ ID NO: 35, and the light chain variable domain comprises a CDR3 region of SEQ ID NO:36, a CDR2 region of SEQ ID NO: 37, and a CDR1 region of SEQ ID NO: 38, or
- d) the heavy chain variable domain comprises a CDR3 region of SEQ ID NO:41, a CDR2 region of SEQ ID NO: 42, and a CDR1 region of SEQ ID NO:43, and the light chain variable domain comprises a CDR3 region of SEQ ID NO: 44, a CDR2 region of SEQ ID NO:45, and a CDR1 region of SEQ ID NO:46.

In one embodiment the antibody binding to human CSF-1R used in the combination therapy is characterized in that the heavy chain variable domain comprises a CDR3 region of SEQ ID NO: 17, a CDR2 region of SEQ ID NO: 18, and a CDR1 region of SEQ ID NO:19, and the light chain variable domain comprises a CDR3 region of SEQ ID NO: 20, a CDR2 region of SEQ ID NO:21, and a CDR1 region of SEQ ID NO:22.

In one embodiment the antibody binding to human CSF-1R used in the combination therapy is characterized in that the heavy chain variable domain comprises a CDR3 region of SEQ ID NO: 25, a CDR2 region of SEQ ID NO: 26, and a CDR1 region of SEQ ID NO: 27, and the light chain variable domain comprises a CDR3 region of SEQ ID NO:28, a CDR2 region of SEQ ID NO: 29, and a CDR1 region of SEQ ID NO: 30.

In one embodiment the antibody binding to human CSF-1R used in the combination therapy is characterized in that the heavy chain variable domain comprises a CDR3 region of SEQ ID NO: 33, a CDR2 region of SEQ ID NO: 34, and a CDR1 region of SEQ ID NO: 35, and the light chain variable domain comprises a CDR3 region of SEQ ID NO:36, a CDR2 region of SEQ ID NO: 37, and a CDR1 region of SEQ ID NO: 38.

In one embodiment the antibody binding to human CSF-1R used in the combination therapy is characterized in that the heavy chain variable domain comprises a CDR3 region of SEQ ID NO:41, a CDR2 region of SEQ ID NO: 42, and a CDR1 region of SEQ ID NO:43, and the light chain variable domain comprises a CDR3 region of SEQ ID NO: 44, a CDR2 region of SEQ ID NO:45, and a CDR1 region of SEQ ID NO:46.

In one embodiment the antibody binding to human CSF-1R used in the combination therapy is characterized in that the antibody binds to human CSF-1R fragment delD4 (SEQ ID NO: 65) and to human CSF-1R-ECD (SEQ ID NO: 64) with a ratio of 1:50 or lower, is further characterized in not binding to human CSF-1R fragment D1-D3 (SEQ ID NO: 66).

The term "antibody" encompasses the various forms of antibodies including but not being limited to whole antibodies, antibody fragments, human antibodies, humanized antibodies, chimeric antibodies, T cell epitope depleted antibodies, and further genetically engineered antibodies as long as the characteristic properties according to the invention are retained. "Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g., described in Houston, J. S., Methods in Enzymol. 203 (1991) 46-88). In addition, antibody fragments comprise single chain polypeptides having the characteristics of a $V_H$ domain binding to CSF-1R, namely being able to assemble together with a $V_L$ domain, or of a $V_L$ domain binding to CSF-1R, namely being able to assemble together with a $V_H$ domain to a functional antigen binding site and thereby providing the property.

The terms "monoclonal antibody" or "monoclonal antibody composition" as used herein refer to a preparation of antibody molecules of a single amino acid composition.

The term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising a mouse variable region and a human constant region are especially preferred. Such rat/human chimeric antibodies are the product of expressed immunoglobulin genes comprising DNA segments encoding rat immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad Sci. USA 81 (1984) 6851-6855; U.S. Pat. No. 5,202,238 and U.S. Pat. No. 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See e.g. Riechmann, L., et al., Nature 332 (1988) 323-327; and Neuberger, M. S., et al., Nature 314 (1985) 268-270. Optionally the framework region can be modified by further mutations. Also the CDRs can be modified by one or more mutations to generate antibodies according to the invention e.g. by mutagenesis based upon molecular modeling as described by Riechmann, L., et al., Nature 332 (1988) 323-327 and Queen, C., et al., Proc. Natl. Acad. Sci. USA 86 (1989) 10029-10033, or others. Particularly preferred CDRs correspond to those representing sequences recognizing the antigens noted above for chimeric antibodies. A "humanized version of an antibody according to the invention" (which is e.g. of mouse origin) refers to an antibody, which is based on the mouse antibody sequences in which the $V_H$ and $V_L$ are humanized by standard techniques (including CDR grafting and optionally subsequent mutagenesis of certain amino acids in the framework region and the CDRs). Preferably such humanized version is chimerized with a human constant region (see e.g. Sequences SEQ ID NO:57-61).

Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

In the following examples the terms "Mab" or "muMab" refer to murine monoclonal antibodies such as Mab 2F11 or Mab 2E10, whereas the term "hMab" refers to humanized monoclonal versions of such murine antibodies such as hMab 2F11-c11, hMab 2F11-d8, hMab 2F11-e7, hMab 2F11-f12, etc.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Brueggemann, M., et al., Year Immunol. 7 (1993) 33-40). Human antibodies can also be produced in phage display libraries (Hoogenboom, H. R., and Winter, G. J. Mol. Biol. 227 (1992) 381-388; Marks, J. D., et al., J. Mol. Biol.

222 (1991) 581-597). The techniques of Cole, et al., and Boerner, et al., are also available for the preparation of human monoclonal antibodies (Cole, S. P. C., et al., Monoclonal Antibodies and Cancer Therapy, Alan R. Liss, p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The antibodies according to the invention include, in addition, such antibodies having "conservative sequence modifications", nucleotide and amino acid sequence modifications which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-CSF-1R antibody can be preferably replaced with another amino acid residue from the same side chain family.

Amino acid substitutions can be performed by mutagenesis based upon molecular modeling as described by Riechmann, L., et al., Nature 332 (1988) 323-327 and Queen, C., et al., Proc. Natl. Acad. Sci. USA 86 (1989) 10029-10033.

The human CSF-1R(CSF-1 receptor; synonyms: M-CSF receptor; Macrophage colony-stimulating factor 1 receptor, Fms proto-oncogene, c-fms, SEQ ID NO: 22)) is known since 1986 (Coussens, L., et al., Nature 320 (1986) 277-280). CSF-1R is a growth factor and encoded by the c-fms proto-oncogene (reviewed e.g. in Roth, P. and Stanley, E. R., Curr. Top. Microbiol. Immunol. 181 (1992) 141-167).

CSF-1R is the receptor for the CSF-1R ligands CSF-1 (macrophage colony stimulating factor, also called M-CSF) (SEQ ID No.: 86) and IL-34 (SEQ ID No.: 87) and mediates the biological effects of these cytokines (Sherr, C. J., et al., Cell 41 (1985) 665-676; Lin, H., et al., Science 320 (2008) 807-811). The cloning of the colony stimulating factor-1 receptor (also called c-fms) was described for the first time in Roussel, M. F., et al., Nature 325 (1987) 549-552. In that publication, it was shown that CSF-1R had transforming potential dependent on changes in the C-terminal tail of the protein including the loss of the inhibitory tyrosine 969 phosphorylation which binds Cbl and thereby regulates receptor down regulation (Lee, P. S., et al., Embo J. 18 (1999) 3616-3628).

CSF-1R is a single chain, transmembrane receptor tyrosine kinase (RTK) and a member of the family of immunoglobulin (Ig) motif containing RTKs characterized by 5 repeated Ig-like subdomains D1-D5 in the extracellular domain (ECD) of the receptor (Wang, Z., et al Molecular and Cellular Biology 13 (1993) 5348-5359). The human CSF-1R Extracellular Domain (CSF-1R-ECD) (SEQ ID NO: 64) comprises all five extracellular Ig-like subdomains D1-D5. The human CSF-1R fragment delD4 (SEQ ID NO: 65) comprises the extracellular Ig-like subdomains D1-D3 and D5, but is missing the D4 subdomain. The human CSF-1R fragment D1-D3 (SEQ ID NO: 66) comprises the respective subdomains D1-D3. The sequences are listed without the signal peptide MGSGPGV-LLL LLVATAWHGQ G (SEQ ID NO: 67). The human CSF-1R fragment D4-D3 (SEQ ID NO: 85) comprises the respective subdomains D4-D3.

Currently two CSF-1R ligands that bind to the extracellular domain of CSF-1R are known. The first one is CSF-1 (colony stimulating factor 1, also called M-CSF, macrophage; human CSF-1, SEQ ID NO: 86) and is found extracellularly as a disulfide-linked homodimer (Stanley, E. R. et al., Journal of Cellular Biochemistry 21 (1983) 151-159; Stanley, E. R. et al., Stem Cells 12 Suppl. 1 (1995) 15-24). The second one is IL-34 (human IL-34; SEQ ID NO: 87) (Hume, D. A., et al, Blood 119 (2012) 1810-1820). Thus in one embodiment the term "CSF-1R ligand" refers to human CSF-1 (SEQ ID NO: 86) and/or human IL-34 (SEQ ID NO: 87).

For experiments often the active 149 amino acid (aa) fragment of human CSF-1 (aa 33-181 of SEQ ID NO: 86) is used. This active 149 aa fragment of human CSF-1 (aa 33-181 of SEQ ID NO: 86) is contained in all 3 major forms of CSF-1 and is sufficient to mediate binding to CSF-1R (Hume, D. A., et al, Blood 119 (2012) 1810-1820).

The main biological effects of CSF-1R signaling are the differentiation, proliferation, migration, and survival of hematopoietic precursor cells to the macrophage lineage (including osteoclast). Activation of CSF-1R is mediated by its CSF-1R ligands, CSF-1 (M-CSF) and IL-34. Binding of CSF-1 (M-CSF) to CSF-1R induces the formation of homodimers and activation of the kinase by tyrosine phosphorylation (Li, W. et al, EMBO Journal. 10 (1991) 277-288; Stanley, E. R., et al., Mol. Reprod. Dev. 46 (1997) 4-10).

The intracellular protein tyrosine kinase domain is interrupted by a unique insert domain that is also present in the other related RTK class III family members that include the platelet derived growth factor receptors (PDGFR), stem cell growth factor receptor (c-Kit) and fms-like cytokine receptor (FLT3). In spite of the structural homology among this family of growth factor receptors, they have distinct tissue-specific functions.

CSF-1R is mainly expressed on cells of the monocytic lineage and in the female reproductive tract and placenta. In addition expression of CSF-1R has been reported in Langerhans cells in skin, a subset of smooth muscle cells (Inaba, T., et al., J. Biol. Chem. 267 (1992) 5693-5699), B cells (Baker, A. H., et al., Oncogene 8 (1993) 371-378) and microglia (Sawada, M., et al., Brain Res. 509 (1990) 119-124). Cells with mutant human CSF-1R ((SEQ ID NO: 23) are known to proliferate independently of ligand stimulation.

As used herein, "binding to human CSF-1R" or "specifically binding to human CSF-1R" or "specifically binds to human CSF-1R" or "which binds to human CSF-1R" or "anti-CSF-1R antibody" refers to an antibody specifically binding to the human CSF-1R antigen with a binding affinity of KD-value of $1.0 \times 10^{-8}$ mol/l or lower at 35° C., in one embodiment of a KD-value of $1.0 \times 10^{-9}$ mol/l or lower at 35° C. The binding affinity is determined with a standard binding assay at 35° C., such as surface plasmon resonance technique (BIAcore®, GE-Healthcare Uppsala, Sweden) A method for determining the KD-value of the binding affinity is described in Example 4. Thus an "antibody binding to human CSF-1R" as used herein refers to an antibody specifically binding to the human CSF-1R antigen with a binding affinity of KD $1.0 \times 10^{-8}$ mol/l or lower (preferably $1.0 \times 10^{-8}$ mol/l-$1.0 \times 10^{-12}$ mol/l) at 35° C., preferably of a KD $1.0 \times 10^{-9}$ mol/l or lower at 35° C. (preferably $1.0 \times 10^{-9}$ mol/l-$1.0 \times 10^{-12}$ mol/l).

The "binding to human CSF-1R fragment delD4 (SEQ ID NO: 65) and to human CSF-1R Extracellular Domain (SEQ ID NO: 64)" as used herein is measured by a Surface Plasmon Resonance assay (Biacore assay) as described in Example 4. The human CSF-1R fragment delD4 (SEQ ID NO: 65) or human CSF-1R Extracellular Domain (SEQ ID NO: 64), respectively, are captured to the surface (each to a separate surface) and the test antibodies were added (each in a separate measurement) and the respective binding signals (Response Units (RU)) were determined. Reference signals (blank surface) were subtracted. If signals of nonbinding test antibodies were slightly below 0 the values were set as 0. Then the ratio of the respective binding signals (binding signal (RU) to human CSF-1R fragment delD4/binding signal (RU) to human CSF-1R Extracellular Domain (CSF-1R-ECD)) is determined. The antibodies according to the invention have a ratio of the binding signals (RU(delD4)/RU(CSF-1R-ECD) of 1:50 or lower, preferably of 1:100 or lower (the lower included end is 0 (e.g. if the RU is 0, then the ratio is 0:50 or 0:100)).

This means that such anti-CSF-1R antibodies according to the invention do not bind to the human CSF-1R fragment delD4 (like the anti-CCR5 antibody m<CCR5>Pz03.1C5 (deposited as DSM ACC 2683 on 18 Aug. 2004 at DSMZ) and have binding signals for binding to the human CSF-1R fragment delD4 in the range of the anti-CCR5 antibody m<CCR5>Pz03.1C5, which are below 20 RU (Response Units), preferably below 10 RU in a Surface Plasmon Resonance (BIAcore) assay as shown in Example 4.

The term "binding to human CSF-1R fragment D1-D3" refers to a binding affinity determination by a Surface Plasmon Resonance assay (Biacore assay). The test antibody is captured to the surface and the human CSF-1R fragment D1-D3 (SEQ ID NO: 66) was added and the respective binding affinities were determined. The terms "not binding to human CSF-1R fragment D1-D3" or "which do not bind to human CSF-1R fragment D1-D3" denotes that in such an assay the detected signal was in the area of no more than 1.2 fold of background signal and therefore no significant binding could be detected and no binding affinity could be determined (see Example 10).

The term "ligand dependent" as used herein refers to a ligand-independent signaling through the extracellular ECD (and does not include the ligand independent signaling mediated by activating point mutations in the intracellular kinase domain).

In one embodiment CSF-1R ligand in this context refers a CSF-1R ligand selected from human CSF-1 (SEQ ID No: 86) and human IL-34 (SEQ ID No: 87); in one embodiment the CSF-1R ligand is human CSF-1 (SEQ ID No: 86); in one embodiment the CSF-1R ligand is human IL-34 (SEQ ID No: 87)).

The invention comprises an antibody binding to human CSF-1R, antibody binding to human CSF-1R, for use in the treatment of a patient having a CSF-1R expressing tumor or having a tumor with CSF-1R expressing macrophage infiltrate, wherein the tumor is characterized by an increase of CSF-1R ligand (in one embodiment the CSF-1R ligand is selected from human CSF-1 (SEQ ID No: 86) and human IL-34 (SEQ ID No: 87); in one embodiment the CSF-1R ligand is human CSF-1 (SEQ ID No: 86); in one embodiment the CSF-1R ligand is human IL-34 (SEQ ID No: 87)) (detectable in serum, urine or tumor biopsies), wherein the anti-CSF-1R antibody is administered in combination with TLR9 agonist. (In one embodiment the CSF-1R antibody is characterized in binding to the (dimerization) domains D4 to D5 (SEQ ID NO: 85) of the extracellular domain of human CSF-1R.

The term "increase of CSF-1R ligand" refers to the overexpression of human CSF-1R ligand (in one embodiment the CSF-1R ligand is selected from human CSF-1 (SEQ ID No: 86) and human IL-34 (SEQ ID No: 87); in one embodiment the CSF-1R ligand is human CSF-1 (SEQ ID No: 86); in one embodiment the CSF-1R ligand is human IL-34 (SEQ ID No: 87)) (compared to normal tissue) before treatment or overexpression of human CSF-1R ligand induced by treatment with anti-CSF-1R antibody (and compared to the expression levels before treatment). In certain embodiments, the term "increase" or "above" refers to a level above the reference level or to an overall increase of 5%, 10%, 20%, 25%, 30%, 40%, 50%, 60%, 70%, 80%, 85%, 90%, 95%, 100% or greater, in CSF-1R ligand level detected by the methods described herein, as compared to the CSF-1R ligand level from a reference sample. In certain embodiments, the term increase refers to the increase in CSF-1R ligand level wherein, the increase is at least about 1.5-, 1.75-, 2-, 3-, 4-, 5-, 6-, 7-, 8-, 9-, 10-, 15-, 20-, 25-, 30-, 40-, 50-, 60-, 70-, 75-, 80-, 90-, or 100-fold higher as compared to the CSF-1R ligand level e.g. predetermined from a reference sample. In one preferred embodiment the term increased level relates to a value at or above a reference level.

In one embodiment of the invention the anti-CSF-1R antibody is characterized in that the antibody binds to human CSF-1R Extracellular Domain (SEQ ID NO: 64) (comprising domains D1 to D5) and binds to domains D1 to D3 (SEQ ID NO: 66) of the extracellular domain of human CSF-1R.

In one embodiment of the invention the anti-CSF-1R antibody is characterized in that the antibody binds to human CSF-1R Extracellular Domain (SEQ ID NO: 64) (comprising domains D1 to D5) and does not bind to domains D1 to D3 (SEQ ID NO: 66) of the extracellular domain of human CSF-1R.

The term "Toll-like receptor 9" (TLR9, CD289; SEQ ID NO: 88) refers to a protein of the Toll-like receptor (TLR) family which plays a fundamental role in pathogen recognition and activation of innate immunity. TLRs are highly conserved from *Drosophila* to humans and share structural and functional similarities. They recognize pathogen-associated molecular patterns (PAMPs) that are expressed on infectious agents, and mediate the production of cytokines necessary for the development of effective immunity. The various TLRs exhibit different patterns of expression. This gene is preferentially expressed in immune cell rich tissues, such as spleen, lymph node, bone marrow and peripheral blood leukocytes. Studies in mice and human indicate that this receptor mediates cellular response to unmethylated CpG dinucleotides in bacterial DNA to mount an innate immune response.

TLR9 is mainly found in the endosomal compartment of B cells, monocytes, macrophages and plasmacytoid Dendritic Cells DCs (Galluzzi et al., OncoImmunology, 1:5, (2012) 699-716). The main ligand of TLR9 is bacterial/viral DNA, differing from its mammalian counterpart for the elevated frequency of unmethylated CpG oligodeoxynucleotides. Indeed, whereas mammalian DNA has no immunostimulatory activity, the administration of bacterial/viral DNA induces a potent Th1 immune response in vivo, which is entirely abrogated in TLR9$^{-/-}$ mice. CpG oligodeoxynucleotides (or CpG ODN) are short single-stranded synthetic DNA molecules that contain a cytidine triphosphate deoxynucleotide ("C") followed by a guanidine triphosphate deoxynucleotide ("G"). The "p" refers to the phosphodiester link between consecutive nucleotides, although some ODN have a modified phosphorothioate (PS) backbone instead. When these CpG motifs are unmethlyated, they act as immunostimulants (Weiner, G J; et al, PNAS 94 (1997) 10833-7). Thus "Toll-like receptor δ agonists" (TLR9 agonist) are characterized in binding to Toll-like receptor 9 and in stimulating TLR9 immune response. E.g. in one embodiment a Toll-like receptor 9 agonist (TLR9 agonist) is characterized by binding to Toll-like receptor 9 on human plasmacytoid dendritic cells (pDCs) and by induction of IFN-alpha, IL-6, and/or IL-12 (elevating the levels of IFN-alpha, IL-6, and/or IL-12) in these plasmacytoid dendritic cells (pDCs).

CpG motifs are considered pathogen-associated molecular patterns (PAMPs) due to their abundance in microbial genomes but their rarity in vertebrate genomes (Bauer, S; Current Topics in Microbiology and Immunology 270 (2002) 145-54). The CpG PAMP is recognized by the pattern recognition receptor (PRR) Toll-Like Receptor 9 (TLR9), which is constitutively expressed only in B cells and plasmacytoid dendritic cells (pDCs) in humans and other higher primates (Rothenfusser, S; et al, Human immunology 63 (2002) 1111-9)

Synthetic CpG ODN differ from microbial DNA in that they have a partially or completely phosphorothioated (PS) backbone instead of the typical phosphodiester backbone and a poly G tail at the 3' end, 5' end, or both. PS modification protects the ODN from being degraded by nucleases such as DNase in the body and poly G tail enhances cellular uptake (Dalpke, A H et al, Immunology 106 (2002) 102-12). The poly G tails form intermolecular tetrads that result in high molecular weight aggregates. These aggregates are responsible for the increased activity the poly G sequence impart; not the sequence itself.

These synthetic oligodeoxynucleotides containing unmethylated CpG motifs (CpG ODNs), such as ODN 1826, have been extensively studied as adjuvants (Steinhagen F. et al., 2011; Vaccine 29(17):3341-55). These CpG motifs are present at a 20-fold greater frequency in bacterial DNA compared to mammalian DNA (Hemmi H. et al., 2000. Nature 408: 740-5). CpG ODNs agonize TLR9, which is expressed on human B cells and plasmacytoid dendritic cells (pDCs), thereby inducing Th1-dominated immune responses (Coffman et al., 2010. Immunity 33(4):492-503). Pre-clinical studies, conducted in rodents and non-human primates, and human clinical trials have demonstrated that CpG ODNs can significantly improve vaccine-specific antibody responses (Steinhagen F. et al., 2011; Vaccine 29(17):3341-55).

Numerous sequences have been shown to stimulate TLR9 with variations in the number and location of CpG dimers, as well as the precise base sequences flanking the CpG dimers. This led to the creation of classes or categories of CpG ODN, which are all TLR9 agonist based on their sequence, secondary structures, and effect on human peripheral blood mononuclear cells (PBMCs). The three main classes of CpG ODNs are class A, B and C, which differ in their immune-stimulatory activities (Krug A. et al., 2001, Eur J Immunol, 31(7): 2154-63). Furthermore, CpG ODNs activate TLR9 in a species-specific manner (Bauer, S. et al., 2001, PNAS, 98(16): 9237-42). One of the first Class A ODN, ODN 2216, was described in 2001 by Krug et al (see above) This class of ODN was distinctly different from the previously described Class B ODN (i.e., ODN 2006) in that it stimulated the production of large amounts of Type I interferons, the most important one being IFNα, and induced the maturation of pDCs.

Class A ODN are also strong activators of NK cells through indirect cytokine signaling. Class A ODN typically contain 7 to 10 PS-modified bases at one or both ends that resist degradation by nucleases and increase the longevity of the ODN. The above rules strictly define the class, but variability of the sequence within these "rules" is possible. It should also be noted that changes to the sequence will affect the magnitude of the response. For example, the internal palindrome sequence can be 4 to 8 base pairs in length and vary in the order of bases, however the pattern, 5'-Pu Pu CG Pu Py CG Py Py-3', was found to be the most active when compared to several other sequences. The poly G tail found at either end of the DNA strand can vary in length and even number, but its presence is critical to the activity of the molecule.

Class B ODN (i.e. ODN 2007) are strong stimulators of human B cell and monocyte maturation. They also stimulate the maturation of pDC but to a lesser extent than Class A ODN and very small amounts of IFNα. The strongest ODN in this class have three 6mer sequences. Class B ODNs have been studied extensively as therapeutic agents because of their ability to induce a strong humoral immune response, making them ideal as a vaccine adjuvant.

ODN 1826 is a type B CpG ODN specific for mouse TLR9. Type B CpG ODNs contain a full phosphorothioate backbone with one or more CpG dinucleotides and can strongly activate B cells (Krug A. et al., 2001, Eur J Immunol, 31(7): 2154-63). ODN 1826, a mouse-reactive surrogate TLR9-agonist has been tested as an adjuvant in numerous animal models (Bauer, S. et al., 2001, PNAS, 98(16):9237-42). Research in mice demonstrated that ODN 1826 administration can induce the activation of antigen presenting cells and type I IFN anti-viral activity 8-9, indicative of a Th1 immune response (Longhi Mp. et al., 2009, J Exp Med 206: 1589-602).

Moreover, the administration of type B CpG oligonucleotides (alone or combined with chemotherapeutics or peptide vaccines) to tumor-bearing rodents reportedly exerts potent anticancer effects. Initial Phase I/II clinical trials to test the safety and efficacy of CpG-7909 for oncological indications were launched in April 2000. Approximately in the same period, CpG-7909 begun to be extensively investigated as an adjuvant for cancer-unrelated indications (mainly antiviral vaccines), showing no severe side effects and encouraging efficacy.

During the last decade, the safety and anticancer potential of CpG-7909 (as a standalone agent or in combination with chemotherapy and/or vaccination approaches) have been investigated in a large number of Phase I/II clinical trials, including studies with leukemia, lymphoma, basal cell carcinoma, 1melanoma, esophageal squamous cell carcinoma, NSCLC, renal cell carcinoma, and prostate cancer patients. Several TLR9 agonist are known and currently developed in clinical testing Agatolimod (tricosasodium salt of a synthetic 24-mer oligonucleotide containing 3 CpG motifs; Pfizer) GNKG168 (CpG ODN; SBI Biotech), IMO-2055 (synthetic oligonucleotide containing unmethylated CpG dinucleotides; Idera Pharmaceuticals), MGN-1703 (Mologen). Typically these TLR9 agonist are used in the treatment of different cancers:

Bacterial and synthetic DNA containing unmethylated CpG motifs act as agonists of TLR9 and induce Th1-type immune response profiles. The immune-stimulatory effects of TLR9 agonists are multifactorial and depend on the nucleotide sequence, the nature of the backbone and the presence of specific structural motifs. Based on the cytokine profiles induced, three distinct types of TLR9 agonists, class A, B and C, have been described. Each class of TLR9 agonist is composed of a different nucleotide sequence that allows formation of structures (or no structures) that generate different immune profiles.

The structure-activity relationships of oligonucleotides that act as agonists of TLR9 was systematically studied (Kandimalla, E. R. and Agrawal, S. (2005) in Toll and Toll Receptors: An Immunologic Perspective (Rich, T., ed.), pp. 181-212, Kluwer Academic/Plenum Publishers, New York). The presence of a CpG motif in oligonucleotides is required for TLR9 stimulation. Oligonucleotides with phosphodiester and phosphorothioate backbone stimulate TLR9-mediated immune responses. Phosphorothioate backbone oligonucleotides are commonly used because they are less susceptible to degradation by ubiquitous nucleases than are phosphodiester oligonucleotides. Introduction of a sulfur atom on the internucleotide phosphodiester bond results in the formation of Rp and Sp diastereoisomers; the Rp diastereomer of phosphorothioate linkage stimulates a stronger TLR9-mediated immune response than does the Sp diastereomer. The negative charges on phosphates between and adjacent to cytosine (C) and guanine (G) are also required for TLR9-mediated activity. Neutralization of charges by incorporation of methylphosphonate linkages at these positions results in the loss of immune-stimulatory activity. Moreover, TLR9 activation is also dependent on the sequences flanking the CpG dinucleotide, the nature of the nucleotide backbone and the secondary structures.

Flanking Sequences Play a Significant Role in TLR9 Stimulation

Chemical modifications introduced at the 2'-position of the sugar ring of a C or G nucleotide in the CpG motif result in the loss of immune-stimulatory activity of TLR9 agonists. In addition, studies of TLR9 agonists containing chemical modifications such as methylphosphonate linkages, 2'-alkyl or 3'-deoxy or -alkyl ribonucleosides, non-nucleotide linkers or abasic nucleotides in the flanking sequences indicate that substitutions incorporated at the fourth to sixth nucleotide positions 5' to the CpG dinucleotide significantly enhance immune-stimulatory activity. In general, modifications incorporated in the 3'-flanking sequence distal to the CpG dinucleotide have effects dependent on the nature of the modification.

TLR9 Requires a Free 5'-End of Agonist for Stimulation

Two CpG oligonucleotides linked through their 5'-ends do not activate immune cells despite the availability of two CpG motifs. When the same oligonucleotides are linked through their 3'-ends, they produce higher and distinct cytokine profiles than the parent CpG oligonucleotide with a single 5'-end. These are the first studies demonstrating the requirement of an accessible or free 5'-end for TLR9 activation and that the receptor reads the sequence from the 5'-end. The transcription factor NF-κB is rapidly activated by TLR9 agonists that contain two 5'-ends, but these compounds have the same activity as conventional TLR9 agonists on the MAPK (mitogen-activated protein kinase) pathway in J774 cells.

These studies suggest that agonists containing two 5'-ends facilitate dimerization of the receptor, leading to rapid activation of immune responses. Moreover, TLR9 activation can be modulated through appropriate presentation of the free 5'-ends and synthetic immune-stimulatory motifs, leading to changes in the downstream cytokine induction profiles. Consistent with these results, recent studies have shown that TLR9 exists in dimer form and binds to single-stranded oligonucleotides. However, only oligonucleotides containing the CpG motif cause conformational changes in the receptor, leading to the activation of immune signalling pathways.

The attachment of oligonucleotides through their 3'-ends not only provides two 5'-ends for optimal activation of TLR9, but also increases the stability against 3'-exonucleases. Oligonucleotides with a phosphodiester backbone and as short as 5 and 6 nt linked through their 3'-ends act as potent TLR9 agonists and produce immune responses. Moreover, oral administration of the novel structure containing TLR9 agonists induces potent mucosal immune responses, acts as an adjuvant with antigens, and prevents and reverses peanut allergy in mouse models because of their greater stability in the gastrointestinal tract.

Functional Groups of Cytosine and Guanine Required for TLR9 Stimulation

As described above, certain chemical modifications introduced within the CpG dinucleotide that alter structure and conformation lead to the loss of immune-stimulatory activity of agonists. One such modification is a replacement of the methyl group at the 5-position of cytosine in the CpG motif of TLR9 agonists. Vertebrates use this feature to distinguish self-DNA from that of bacterial DNA, which contains more unmethylated CpG motifs.

The effects of various pyrimidine analogues (Y), such as 5-OH-dC, dU, dP, 1-(2'-deoxy-β-D-ribofuranosyl)-2-oxo-7-deaza-8-methyl-purine, N3-Me-dC and N4-Et-dC, in place of cytosine (Kandimalla, E. R., et al (2001) Bioorg. Med. Chem. 9, 807-813; Kandimalla, E. R., et al, S. (2003) PNAS. 100, 14303-14308; or Putta, M. R., et al, S. (2006) Nucleic Acids Res. 34, 3231-3238). To understand the role of different functional groups of guanine in the recognition of TLR9, several purine nucleobases (R) such as 7-deaza-dG, N1-Me-dG, 2-amino-D-purine, nebularine, 2-amino-dA, 7-deaza-D-xanthine, K-base and dI were examined in place of guanine in the CpG (Kandimalla, E. R., et al (2001) Bioorg. Med. Chem. 9, 807-813; Kandimalla, E. R., et al. (2003) PNAS. 100, 14303-14308; Putta, M. R., et al, (2006) Nucleic Acids Res. 34, 3231-3238; Kandimalla, E. R., et al (2003) Nucleic Acids Res. 31, 2393-2400; or Kandimalla, E. R., et al. (2005) PNAS. 102, 6925-6930). These studies led to the development of alternative synthetic nucleotide motifs (YpG, CpR) for immune modulation and have demonstrated acceptance by TLR9 of certain heterocyclic base variants.

Novel synthetic agonists of TLR9 (S. Agrawal and E. R. Kandimalla, Biochemical Society Transactions (2007) 35, (1461-1467)): The combinations of novel structures and synthetic immune-stimulatory motifs described above provided us with tools to generate combinatorial libraries of novel synthetic agonists of TLR9. Systematic studies of several TLR9 agonists that have two 5'-ends and contain synthetic CpR dinucleotides in different nucleotide compositions in mouse, human and monkey systems suggest that nucleotide sequence and secondary structures play a role in modulating the immune response. Based on these studies, we have broadly identified two different groups of synthetic agonists of TLR9.

In one embodiment the TLR9 agonist is characterized by induction of IFN-alpha, IL-6, and/or IL-12 (elevating the levels of IFN-alpha, IL-6, and/or IL-12) in plasmacytoid dendritic cells (pDCs). In one embodiment the TLR9 agonist is characterized by elevating the level of IFN-alpha in human plasmacytoid dendritic cells (pDCs) (as measured by sandwich ELISA as described below or e.g in WO2010/088395) Assay for Measuring IFN-Alpha Induction (Elevating the Levels of IFN-Alpha, IL-6, and/or IL-12) by TLR9 Agonist of the Invention in Human pDCs:

Human PBMC isolation: Peripheral blood mononuclear cells (PBMCs) from freshly drawn healthy volunteer blood (CBR Laboratories, Boston, Mass.) are isolated by Ficoll density gradient centrifugation method (Histopaque-1077, Sigma).

Human pDC isolation: Human plasmacytoid dendritic cells (pDCs) are isolated from freshly obtained healthy human volunteer's blood PBMCs by positive selection using the BDC A4 cell isolation kits (Miltenyi Biotec) according to the manufacturer's instructions.

Human pDCs are plated in 96-well dishes using $1 \times 10^6$ cells/ml. Individual immune modulatory compounds from Table I were dissolved in DPBS (pH 7.4; Mediatech) are added to the cell cultures at doses of 0, 0.1, 0.3, 1.0, 3.0, or 10.0 .micro.g/ml. The cells were then incubated at 37 (0)C for 24 hours and the supernatants were collected for luminex multiplex or ELISA assays.

In the levels of IFN-alpha, IL-6, and/or IL-12 are measured by sandwich ELISA. The required reagents, including cytokine antibodies and standards, can be purchased from PharMingen.

IFN-alpha has been known as an antiviral cytokine for many years. It stimulates Th1 cell development, therefore promoting the effects of CG-containing DNA molecules. IFN-alpha also exhibits antitumour activity in mouse and human malignancies and is capable of decreasing the tumourigenicity of transplanted tumour cells, partially by activating cytotoxic T cells and thereby increasing the likelihood of tumour-cell cytolysis. NK cell and macrophage activity, both also important for antitumour cytotoxicity, are also increased by IFN-alpha (Brassard et al., J. Leukoc. Biol. 2002 71: 565-81). Therefore, increasing the amount of IFN-alpha upon stimulation with the DNA constructs of the present disclosure is expected to be beneficial for the treatment of cancer.

In one embodiment of the invention the TLR9 agonist of the invention is an oligodeoxynucleotide containing a) cytosine-phosphate-guanosine (CpG) motifs (CpG ODNs) b) pyrimidine-phosphate-guanosine (YpG) motifs (YpG ODNs) or c) cytosine-phosphate-purine (CpR) motifs (CpR ODNs).

In one embodiment of the invention the TLR9 agonist of the invention is an oligodeoxynucleotide containing a) cytosine-phosphate-guanosine (CpG) motifs (CpG ODNs) b) pyrimidine-phosphate-guanosine (YpG) motifs (YpG ODNs) or c) Purine-phosphate-guanosine (RpG) motifs (RpG ODNs) wherein the TLR9 agonist stimulates TLR9 (in one embodiment the TLR9 agonist induces the maturation of plasmacytoid dendritic cells (pDCs); in one embodiment the TLR9 agonist is characterized by human B cell maturation; in one embodiment)

In one embodiment of the invention the TLR9 agonist of the invention is an oligodeoxynucleotide containing cytosine-phosphate-guanosine (CpG) motifs (CpG ODNs).

In one embodiment of the invention the TLR9 agonist of the invention is a Class A CpG ODN.

In one embodiment the TLR9 agonist of the invention is an oligodeoxynucleotide comprising a) a poly G sequence at the 5' end, or the 3' end, or at both ends b) an internal palindrome sequence;

c) GC dinucleotides contained within the internal palindrome, and d) a partially PS-modified backbone Class A CpG ODN typically contain 7 to 10 PS-modified bases at one or both ends that resist degradation by nucleases and increase the longevity of the ODN. The above rules strictly define the class, but variability of the sequence within these rules is possible. The internal palindrome sequence can be 4 to 8 base pairs in length and vary in the order of bases, however the pattern, 5'-Pu Pu CG Pu Py CG Py Py-3', was found to be the most active when compared to several other sequences. The poly G tail found at either end of the DNA strand can vary in length and number.

In one embodiment the Class A CpG ODN (Xueqing Liang, et al, Blood. 2010 Jun. 17; 115(24): 5041-5052) is selected from the group consisting of CpG ODN 2216 (5'-ggGGGACGATCGTCggggG-3') (SEQ ID NO: 89) CpG ODN PB4 (5'-tcgGACGATCGTCggggG-3') (SEQ ID NO: 90); or CpG ODN 1002 (5'-ggGGTCGTTCGTCGT-TggggG-3') (SEQ ID NO: 91).

In one embodiment of the invention the TLR9 agonist of the invention is a Class B CpG ODN.

In one embodiment the TLR9 agonist of the invention is a oligodeoxynucleotides comprising a) one or more 6mer unmethylated cytosine-phosphate-guanosine (CpG) motifs 5'-Pu Py C G Py Pu-3' (one or more 6mer 5'-RYCGYR-3' 6-mers (R=A or G; Y=T or C))

b) a fully phosphorothioated (PS-modified) backbone; and c) 18 to 28 nucleotides in length In one embodiment the Class B CPG ODN is selected from the group consisting of CpG-28, CpG-685 (GNKG168; CpG ODN; SBI Biotech), CpG-684 and CpG-7909 (CPG-ODN 2006, PF-3512676, Agatolimod).

CpG-7909 (CpG 2006, PF-3512676, Agatolimod) is a Synthetic, 24-mer phosphothioate oligodeoxynucleotide (d(P-Thio)(T-C-G-T-C-G-T-T-T-T-G-T-C-G-T-T-T-T-G-T-C-G-T-T)DNA) (5'-tcgtcgttttgtcgttttgtcgtt-3') (SEQ ID NO: 92) containing multiple cytosine-phosphate-guanosine (CpG) motifs or one of its derivatives like tricosasodium salt. The preparation is described e.g. in WO 9818810 or U.S. Pat. No. 7,223,741)

CpG-685 (GNKG168; CpG ODN; SBI Biotech) is synthetic, 21-mer, unmethylated CpG motif-based oligodeoxynucleotide (ODN) (685, 5'-tcgtcgacgtcgttcgttctc-3') (SEQ ID NO: 93), with immunostimulatory activity. CpG685 (GNKG168), a 21-mer fully phosphorothioated oligonucleotides designed to directly target Toll-like receptor 9 that mediates cellular responses in B cells, showed antitumor effects in SCID mouse and is under clinical development for the treatment of human chronic lymphocytic leukemia (B-CLL) by SBI Biotech Co. Herein, a sensitive and specific assay was developed in plasma and cell lysate to support its preclinical pharmacology studies. CpG oligodeoxynucleotide GNKG168 binds to and activates Toll-like receptor 9 (TLR9) and is taken up into cells by endocytosis; once internalized, it may activate numerous signaling transduction pathways resulting in the release of multiple cytokines, such as immunoglobulins (Igs), interferons (IFNs), interleukins (ILs) and tumor necrosis factor (TNF).

CpG-684 is synthetic, 23-mer, unmethylated CpG motif-based oligodeoxynucleotide (ODN) 684, 5'-tcgacgttcgtcgt-tcgtcgttc-3' (SEQ ID NO: 94);

CpG-28 synthetic unmethylated CpG motif-based oligodeoxynucleotide (ODN), containing multiple repeats of unmethylated CpG motifs (CpG ODN) with immunostimulatory activity (5'-TAAACGTTATAACGTTATGACGTCAT-3') (SEQ ID NO: 95) with a wholly phosphorothioate backbone (Carpentier A F, et al Front Biosci. 2003; 8:e115-e127; Meng Y, et al, Int J Cancer. 2005; 116:992-997; or Carpentier A, et al. Neuro-Oncology 2006; 8:60-66). Upon entering the cell via endocytosis, CpG-28 activates numerous signaling transduction pathways resulting in the release of multiple cytokines. CpG-28 has immunomodulatory properties with direct activation of B-lymphocytes, dendritic and NK cells resulting in the stimulation of innate immunity and antibody-dependant cell cytotoxicity (ADCC). Additionally, this agent indirectly modulates T-cell responses though the release of cytokines (IL-12 and IFN gamma) to induce a preferential shift to the Th1 (helper) phenotype resulting in enhanced CD8+ cellular cytotoxicity.

In one embodiment of the invention the TLR9 agonist of the invention is a oligodeoxynucleotides containing pyrimidine-phosphate-guanosine (YpG) motifs (YpG ODNs).

In one embodiment of the invention the TLR9 agonist of the invention is a oligodeoxynucleotides containing cytosine-phosphate-purine (CpR) motifs (CpR ODNs).

In one embodiment of the invention the TLR9 agonist of the invention is IMO-2055 (Idera) (ODN consisting of 3'-3'-linked structure and synthetic CpR(R=2'-deoxy-7-deazaguanosine) motif)

In one embodiment of the invention the TLR9 agonist of the invention is a oligodeoxynucleotides containing a) cytosine-phosphate-guanosine (CpG) motifs (CpG ODNs) b) pyrimidine-phosphate-guanosine (YpG) motifs (YpG ODNs) or c) cytosine-phosphate-purine (CpR) motifs (CpR ODNs).

In one embodiment of the invention the TLR9 agonist of the invention is a oligodeoxynucleotides based CpG motif-containing circular ODN (e.g MGN-1703 from Mologen as described in WO2012/085291) based on the dSLIM® technology (this technology is described in WO2001/07055).

In one embodiment of the invention the TLR9 agonist is selected from the group consisting of CpG ODN 2216 CpG ODN 1002 CpG-28, CpG-685, CpG-684, CpG-7909, IMO-2055 or MGN-1703. In one embodiment of the invention the TLR9 agonist is selected from the group consisting of CpG-685, CpG-7909, IMO-2055 or MGN-1703. In one embodiment the TLR9 agonist is selected from the group consisting of CpG-7909, IMO-2055 or MGN-1703.

In one embodiment of the invention the CSF-1R antibody is selected from antibodies described in WO 2009/026303, WO 2009/112245, WO2011/123381(A1) or WO2011/070024; and the TLR9 agonist is selected from the group consisting of CpG-685, CpG-7909, IMO-2055 or MGN-1703.

In one embodiment of the invention the CSF-1R antibody is selected from antibodies binding to human CSF-1R, characterized in that
 a) the heavy chain variable domain comprises a CDR3 region of SEQ ID NO:1, a CDR2 region of SEQ ID NO: 2, and a CDR1 region of SEQ ID NO:3, and the light chain variable domain comprises a CDR3 region of SEQ ID NO: 4, a CDR2 region of SEQ ID NO:5, and a CDR1 region of SEQ ID NO:6, or,
 b) the heavy chain variable domain comprises a CDR3 region of SEQ ID NO: 9, a CDR2 region of SEQ ID NO: 10, and a CDR1 region of SEQ ID NO: 11, and the light chain variable domain comprises a CDR3 region of SEQ ID NO:12, a CDR2 region of SEQ ID NO: 13, and a CDR1 region of SEQ ID NO: 14, or
 c) the heavy chain variable domain comprises a CDR3 region of SEQ ID NO: 17, a CDR2 region of SEQ ID NO: 18, and a CDR1 region of SEQ ID NO:19, and the light chain variable domain comprises a CDR3 region of SEQ ID NO: 20, a CDR2 region of SEQ ID NO:21, and a CDR1 region of SEQ ID NO:22, or
 d) the heavy chain variable domain comprises a CDR3 region of SEQ ID NO: 25, a CDR2 region of SEQ ID NO: 26, and a CDR1 region of SEQ ID NO: 27, and the light chain variable domain comprises a CDR3 region of SEQ ID NO:28, a CDR2 region of SEQ ID NO: 29, and a CDR1 region of SEQ ID NO: 30, or
 e) the heavy chain variable domain comprises a CDR3 region of SEQ ID NO: 33, a CDR2 region of SEQ ID NO: 34, and a CDR1 region of SEQ ID NO: 35, and the light chain variable domain comprises a CDR3 region of SEQ ID NO:36, a CDR2 region of SEQ ID NO: 37, and a CDR1 region of SEQ ID NO: 38, or
 f) the heavy chain variable domain comprises a CDR3 region of SEQ ID NO:41, a CDR2 region of SEQ ID NO: 42, and a CDR1 region of SEQ ID NO:43, and the light chain variable domain comprises a CDR3 region of SEQ ID NO: 44, a CDR2 region of SEQ ID NO:45, and a CDR1 region of SEQ ID NO:46, or
 g) the heavy chain variable domain comprises a CDR3 region of SEQ ID NO: 49, a CDR2 region of SEQ ID NO: 50, and a CDR1 region of SEQ ID NO: 51, and the light chain variable domain comprises a CDR3 region of SEQ ID NO:52, a CDR2 region of SEQ ID NO: 53, and a CDR1 region of SEQ ID NO: 54;
 and the TLR9 agonist is selected from the group consisting of CpG-685, CpG-7909, IMO-2055 or MGN-1703

In one embodiment of the invention the CSF-1R antibody is selected from antibodies binding to human CSF-1R, is characterized in that
 the heavy chain variable domain is SEQ ID NO:39 and the light chain variable domain is SEQ ID NO:40.
 and the TLR9 agonist is selected from the group consisting of CpG-685, CpG-7909, IMO-2055 or MGN-1703

In general, many suitable TLR9 agonists are known in the art. Thes TLR9 agonists are contemplated to be used for the present combination therapy of the invention. TLR9 specifically recognises CpG DNA that is unmethylated, and initiates a signalling cascade leading to the production of proinflammatory cytokines. Methylation of the cytosine within the CpG motif strongly reduces the affinity of TLR9. Double stranded (ds) CpG DNA is a weaker stimulator of TLR9 compared to its single stranded (ss) counterpart.

Naturally occurring agonists of TLR9 are described in Smith & Wickstrom (1998) J. Natl. Cancer Inst. 90:1146-1154), and their role in cancer is described in Damiano et al. (2007) Proc. Nat. Acad. Sci. USA 104: 12468-12473.

CPG 7909 is an immunostimulatory TLR9 agonist oligodeoxynucleotide that was found to be well tolerated in a phase 1/1 I clinical study (Cooper et al, (2004) J. Clin. Immunol., 24(6): 693-701). The CpG enriched, synthetic oligodeoxynucleotide TLR9 agonist PF-3512676 was found to have antilymphoma activity in a phase 1/1 I clinical study (Brody et al (2010) J. Clin. Oncol., 28(28): 4324-32).

Certain TLR9 agonists are comprised of 3-3' linked DNA structures containing a core CpR dinucleotide, wherein the R is a modified guanosine (U.S. Pat. No. 7,276,489). In addition, specific chemical modifications have allowed the preparation of specific oligonucleotide analogues that generate distinct modulations of the immune response. In particular, structure activity relationship studies have allowed identification of synthetic motifs and novel DNA-based compounds that generate specific modulations of the immune response and these modulations are distinct from those generated by unmethylated CpG dinucleotides (Kandimalla et al. (2005) Proc. Natl. Acad. Sci. USA 102: 6925-6930; Kandimalla of al. (2003) Proc. Nat. Acad. Sci. USA 100: 14303-14308; Cong et al. (2003) Biochem Biophys Res. Commun. 310: 1133-1139; Kandimalla of al. (2003) Biochem. Biophys. Res. Commun 306: 948-953; Kandimalla et al. (2003) Nucleic Acids Res. 31:2393-2400; Yu, D. et al. (2003) Bioorg. Med. Chem. 11:459-464; Bhagat, L. et al. (2003) Biochem. Biophys. Res. Commun 300:853-861; Yu, D. et al. (2002) Nucleic Acids Res. 30:4460-4469; Yu, D. et al. (2002) J. Med. Chem. 45:4540-4548. Yu, D. et al. (2002) Biochem. Biophys. Res. Commun 297:83-90; Kandimalla. E. et al. (2002) Bioconjug. Chem. 13:966-974; Yu, D. et al. (2002) Nucleic Acids Res. 30:1613-1619; Yu, D. et al. (2001) Bioorg. Med. Chem. 9: 2803-2808; Yu et al. (2001) Bioorg. Med. Chem. Lett. 1:2263-2267; Kandimalla et al. (2001) Bioorg. Med. Chem. 9: 807-813; Yu et al. (2000) Bioorg. Med. Chem. Lett. 10: 2585-2588; and Putta et al. (2006) Nucleic Acids Res. 34: 3231-3238).

US 2009/0053206 describes a number of TLR9 agonists, in particular compounds 1-169 listed in Table 1; US 2008/0292648 describes a number of TLR9 agonists, in particular compounds 1-92 listed in Table 1; and US 2007/0105800 describes oligonucleotide based compounds that are TLR9 agonists (Idera Pharmaceuticals). Suitable TLR9 agonists may also include the selective TLR9 agonists IMO-2055, IMO-2125 and IMO-2134 that are undergoing phase 1/phase 2 clinical trials (Idera Pharmaceuticals). US 2010/0016250 describes a number of TLR9 agonists, in particular compounds of Formula I (Kyowa Hakko Kirin Co). As mentioned above, US 2009/0041809 describes compositions that are TLR9 agonists or both TLR3 and TLR9 agonists (Nventa Pharmaceuticals).

Different TLR9 agonists to be used for the present combination therapy of the invention are described in detail in WO2007/7047396, WO2007/7047396, WO2010088395, WO03035695, WO2012085291, WO 1998/018810, WO 2005/042018, WO2008073959, WO2009018431, WO2007084237.

The term "epitope" denotes a protein determinant of human CSF-1R capable of specifically binding to an antibody. Epitopes usually consist of chemically active surface groupings of molecules such as amino acids or sugar side chains and usually epitopes have specific three dimensional structural characteristics, as well as specific charge characteristics. Conformational and nonconformational epitopes are distinguished in that the binding to the former but not the latter is lost in the presence of denaturing solvents. Preferably an antibody according to the invention binds specifically to native and to denatured CSF-1R.

The "variable domain" (variable domain of a light chain ($V_L$), variable domain of a heavy chain ($V_H$)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

The terms "nucleic acid" or "nucleic acid molecule", as used herein, are intended to include DNA molecules and RNA molecules. A nucleic acid molecule may be single-stranded or double-stranded, but preferably is double-stranded DNA.

The term "amino acid" as used within this application denotes the group of naturally occurring carboxy-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The antibodies according to the invention are preferably produced by recombinant means. Therefore the antibody is preferably an isolated monoclonal antibody. Such recombinant methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in appropriate prokaryotic or eukaryotic host cells like CHO cells, NS0 cells, SP2/0 cells, HEK293 cells, COS cells, yeast, or E. coli cells, and the antibody is recovered from the cells (supernatant or cells after lysis).

Recombinant production of antibodies is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The antibodies may be present in whole cells, in a cell lysate, or in a partially purified or substantially pure form. Purification is performed in order to eliminate other cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987).

Expression in NS0 cells is described by, e.g., Barnes, L. M., et al., Cytotechnology 32 (2000) 109-123; and Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies are readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

As used herein, the expressions "cell", "cell line", and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

The "Fc part" of an antibody is not involved directly in binding of an antibody to an antigen, but exhibit various effector functions. A "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ, and μ, respectively. The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described e.g. by Boackle, R. J., et al., Nature 282 (1979) 742-743; Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virology 75 (2001) 12161-12168; Morgan, A., et al., Immunology 86 (1995) 319-324; EP 0 307 434. Such binding sites are e.g. L234, L235, D270, N297, E318, K320, K322, P331 and P329 (numbering according to EU index of Kabat, E. A., see below). Antibodies of subclass IgG1, IgG2 and IgG3 usually show complement activation and C1q and C3 binding, whereas IgG4 do not activate the complement system and do not bind C1q and C3.

In one embodiment the antibody according to the invention comprises a Fc part derived from human origin and preferably all other parts of the human constant regions. As used herein the term "Fc part derived from human origin" denotes a Fc part which is either a Fc part of a human antibody of the subclass IgG1, IgG2, IgG3 or IgG4, preferably a Fc part from human IgG1 subclass, a mutated Fc part from human IgG1 subclass (preferably with a mutation on L234A+L235A), a Fc part from human IgG4 subclass or a mutated Fc part from human IgG4 subclass (preferably with a mutation on S228P). Mostly preferred are the human heavy chain constant regions of SEQ ID NO: 58 (human IgG1 subclass), SEQ ID NO: 59 (human IgG1 subclass with mutations L234A and L235A), SEQ ID NO: 60 human IgG4 subclass), or SEQ ID NO: 61 (human IgG4 subclass with mutation S228P).

Preferably the antibody according to the invention is of human IgG1 subclass or of human IgG4 subclass. In one embodiment the antibody according to the invention is of human IgG1 subclass. In one embodiment the antibody according to the invention is of human IgG4 subclass.

In one embodiment the antibody according to the invention is characterized in that the constant chains are of human origin. Such constant chains are well known in the state of the art and e.g. described by Kabat, E. A., (see e.g. Johnson, G. and Wu, T. T., Nucleic Acids Res. 28 (2000) 214-218). For example, a useful human heavy chain constant region comprises an amino acid sequence of SEQ ID NO: 58. For example, a useful human light chain constant region comprises an amino acid sequence of a kappa-light chain constant region of SEQ ID NO: 57.

In one embodiment the antibody binding to human CSF-1R used in the combination therapy is characterized in that
  a) the heavy chain variable domain is SEQ ID NO:23 and the light chain variable domain is SEQ ID NO:24, or
  b) the heavy chain variable domain is SEQ ID NO:31 and the light chain variable domain is SEQ ID NO:32, or
  c) the heavy chain variable domain is SEQ ID NO:39 and the light chain variable domain is SEQ ID NO:40, or
  d) the heavy chain variable domain is SEQ ID NO:47 and the light chain variable domain is SEQ ID NO:48, or
  e) the heavy chain variable domain is SEQ ID NO:55 and the light chain variable domain is SEQ ID NO:56.

In one embodiment the antibody binding to human CSF-1R used in the combination therapy is characterized in that
a) the heavy chain variable domain is SEQ ID NO:23 and the light chain variable domain is SEQ ID NO:24, or
b) the heavy chain variable domain is SEQ ID NO:31 and the light chain variable domain is SEQ ID NO:32, or
c) the heavy chain variable domain is SEQ ID NO:39 and the light chain variable domain is SEQ ID NO:40, or
d) the heavy chain variable domain is SEQ ID NO:47 and the light chain variable domain is SEQ ID NO:48.

In one embodiment the antibody binding to human CSF-1R used in the combination therapy is characterized in that the heavy chain variable domain is SEQ ID NO:23 and the light chain variable domain is SEQ ID NO:24.

In one embodiment the antibody binding to human CSF-1R used in the combination therapy is characterized in that the heavy chain variable domain is SEQ ID NO:31 and the light chain variable domain is SEQ ID NO:32.

In one embodiment the antibody binding to human CSF-1R used in the combination therapy is characterized in that the heavy chain variable domain is SEQ ID NO:39 and the light chain variable domain is SEQ ID NO:40.

In one embodiment the antibody binding to human CSF-1R used in the combination therapy is characterized in that the heavy chain variable domain is SEQ ID NO:47 and the light chain variable domain is SEQ ID NO:48.

In one embodiment the antibody binding to human CSF-1R used in the combination therapy is characterized in that the heavy chain variable domain is SEQ ID NO:15 and the light chain variable domain is SEQ ID NO:16, or a humanized version thereof.

In one embodiment the antibody binding to human CSF-1R used in the combination therapy is characterized in that the heavy chain variable domain is SEQ ID NO:75 and the light chain variable domain is SEQ ID NO:76; or a humanized version thereof.

In one embodiment the antibody binding to human CSF-1R used in the combination therapy is characterized in that the heavy chain variable domain is SEQ ID NO:83 and the light chain variable domain is SEQ ID NO:84; or a humanized version thereof.

In one embodiment the antibody binding to human CSF-1R used in the combination therapy is characterized in that
a) the heavy chain variable domain comprises a CDR3 region of SEQ ID NO:1, a CDR2 region of SEQ ID NO: 2, and a CDR1 region of SEQ ID NO:3, and the light chain variable domain comprises a CDR3 region of SEQ ID NO: 4, a CDR2 region of SEQ ID NO:5, and a CDR1 region of SEQ ID NO:6, or,
b) the heavy chain variable domain comprises a CDR3 region of SEQ ID NO: 9, a CDR2 region of SEQ ID NO: 10, and a CDR1 region of SEQ ID NO: 11, and the light chain variable domain comprises a CDR3 region of SEQ ID NO:12, a CDR2 region of SEQ ID NO: 13, and a CDR1 region of SEQ ID NO: 14, or
c) the heavy chain variable domain comprises a CDR3 region of SEQ ID NO: 17, a CDR2 region of SEQ ID NO: 18, and a CDR1 region of SEQ ID NO:19, and the light chain variable domain comprises a CDR3 region of SEQ ID NO: 20, a CDR2 region of SEQ ID NO:21, and a CDR1 region of SEQ ID NO:22, or
d) the heavy chain variable domain comprises a CDR3 region of SEQ ID NO: 25, a CDR2 region of SEQ ID NO: 26, and a CDR1 region of SEQ ID NO: 27, and the light chain variable domain comprises a CDR3 region of SEQ ID NO:28, a CDR2 region of SEQ ID NO: 29, and a CDR1 region of SEQ ID NO: 30, or
e) the heavy chain variable domain comprises a CDR3 region of SEQ ID NO: 33, a CDR2 region of SEQ ID NO: 34, and a CDR1 region of SEQ ID NO: 35, and the light chain variable domain comprises a CDR3 region of SEQ ID NO:36, a CDR2 region of SEQ ID NO: 37, and a CDR1 region of SEQ ID NO: 38, or
f) the heavy chain variable domain comprises a CDR3 region of SEQ ID NO:41, a CDR2 region of SEQ ID NO: 42, and a CDR1 region of SEQ ID NO:43, and the light chain variable domain comprises a CDR3 region of SEQ ID NO: 44, a CDR2 region of SEQ ID NO:45, and a CDR1 region of SEQ ID NO:46, or
g) the heavy chain variable domain comprises a CDR3 region of SEQ ID NO: 49, a CDR2 region of SEQ ID NO: 50, and a CDR1 region of SEQ ID NO: 51, and the light chain variable domain comprises a CDR3 region of SEQ ID NO:52, a CDR2 region of SEQ ID NO: 53, and a CDR1 region of SEQ ID NO: 54; or
h) the heavy chain variable domain comprises a CDR3 region of SEQ ID NO:69, a CDR2 region of SEQ ID NO: 70, and a CDR1 region of SEQ ID NO:71, and the light chain variable domain comprises a CDR3 region of SEQ ID NO: 72, a CDR2 region of SEQ ID NO:73, and a CDR1 region of SEQ ID NO:74, or
i) the heavy chain variable domain comprises a CDR3 region of SEQ ID NO: 77, a CDR2 region of SEQ ID NO: 78, and a CDR1 region of SEQ ID NO: 79, and the light chain variable domain comprises a CDR3 region of SEQ ID NO:80, a CDR2 region of SEQ ID NO: 81, and a CDR1 region of SEQ ID NO: 82.

In one embodiment the combination therapy with an antibody binding to human CSF-1R, is characterized in that the heavy chain variable domain comprises a CDR3 region of SEQ ID NO: 17, a CDR2 region of SEQ ID NO: 18, and a CDR1 region of SEQ ID NO:19, and the light chain variable domain comprises a CDR3 region of SEQ ID NO: 20, a CDR2 region of SEQ ID NO:21, and a CDR1 region of SEQ ID NO:22.

In one embodiment the combination therapy with an antibody binding to human CSF-1R, is characterized in that the heavy chain variable domain comprises a CDR3 region of SEQ ID NO: 25, a CDR2 region of SEQ ID NO: 26, and a CDR1 region of SEQ ID NO: 27, and the light chain variable domain comprises a CDR3 region of SEQ ID NO:28, a CDR2 region of SEQ ID NO: 29, and a CDR1 region of SEQ ID NO: 30.

In one embodiment the combination therapy with an antibody binding to human CSF-1R, is characterized in that the heavy chain variable domain comprises a CDR3 region of SEQ ID NO: 33, a CDR2 region of SEQ ID NO: 34, and a CDR1 region of SEQ ID NO: 35, and the light chain variable domain comprises a CDR3 region of SEQ ID NO:36, a CDR2 region of SEQ ID NO: 37, and a CDR1 region of SEQ ID NO: 38.

In one embodiment the combination therapy with an antibody binding to human CSF-1R, is characterized in that the heavy chain variable domain comprises a CDR3 region of SEQ ID NO:41, a CDR2 region of SEQ ID NO: 42, and a CDR1 region of SEQ ID NO:43, and the light chain variable domain comprises a CDR3 region of SEQ ID NO: 44, a CDR2 region of SEQ ID NO:45, and a CDR1 region of SEQ ID NO:46.

The invention comprises a method for the treatment of a patient in need of therapy, characterized by administering to the patient a therapeutically effective amount of an antibody according to the invention.

The invention comprises the use of an antibody according to the invention for the described therapy.

One preferred embodiment of the invention are the CSF-1R antibodies of the present invention for use in the treatment of "CSF-1R mediated diseases" or the CSF-1R antibodies of the present invention for use for the manufacture of a medicament in the treatment of "CSF-1R mediated diseases", which can be described as follows:

There are 3 distinct mechanisms by which CSF-1R signaling is likely involved in tumor growth and metastasis. The first is that expression of CSF-ligand and receptor has been found in tumor cells originating in the female reproductive system (breast, ovarian, endometrium, cervical) (Scholl, S. M., et al., J. Natl. Cancer Inst. 86 (1994) 120-126; Kacinski, B. M., Mol. Reprod. Dev. 46 (1997) 71-74; Ngan, H. Y., et al., Eur. J. Cancer 35 (1999) 1546-1550; Kirma, N., et al., Cancer Res 67 (2007) 1918-1926) and the expression has been associated with breast cancer xenograft growth as well as poor prognosis in breast cancer patients. Two point mutations were seen in CSF-1R in about 10-20% of acute myelocytic leukemia, chronic myelocytic leukemia and myelodysplasia patients tested in one study, and one of the mutations was found to disrupt receptor turnover (Ridge, S. A., et al., Proc. Natl. Acad. Sci USA 87 (1990) 1377-1380). However the incidence of the mutations could not be confirmed in later studies (Abu-Duhier, F. M., et al., Br. J. Haematol. 120 (2003) 464-470). Mutations were also found in some cases of hepatocellular cancer (Yang, D. H., et al., Hepatobiliary Pancreat. Dis. Int. 3 (2004) 86-89) and idiopathic myelofibrosis (Abu-Duhier, F. M., et al., Br. J. Haematol. 120 (2003) 464-470). Recently, in the GDM-1 cell line derived from a patient with myelomonoblastic leukemia the Y571D mutation in CSF-1R was identified (Chase, A., et al., Leukemia 23 (2009) 358-364).

Pigmented villonodular synovitis (PVNS) and Tenosynovial Giant cell tumors (TGCT) can occur as a result of a translocation that fuses the M-CSF gene to a collagen gene COL6A3 and results in overexpression of M-CSF (West, R. B., et al., Proc. Natl. Acad. Sci. USA 103 (2006) 690-695). A landscape effect is proposed to be responsible for the resulting tumor mass that consists of monocytic cells attracted by cells that express M-CSF. TGCTs are smaller tumors that can be relatively easily removed from fingers where they mostly occur. PVNS is more aggressive as it can recur in large joints and is not as easily controlled surgically.

The second mechanism is based on blocking signaling through M-CSF/CSF-1R at metastatic sites in bone which induces osteoclastogenesis, bone resorption and osteolytic bone lesions. Breast, multiple myeloma and lung cancers are examples of cancers that have been found to metastasize to the bone and cause osteolytic bone disease resulting in skeletal complications. M-CSF released by tumor cells and stroma induces the differentiation of hematopoietic myeloid monocyte progenitors to mature osteoclasts in collaboration with the receptor activator of nuclear factor kappa-B ligand-RANKL. During this process, M-CSF acts as a permissive factor by giving the survival signal to osteoclasts (Tanaka, S., et al., J. Clin. Invest. 91 (1993) 257-263). Inhibition of CSF-1R activity during osteoclast differentiation and maturation with an anti-CSF-1R antibody is likely to prevent unbalanced activity of osteoclasts that cause osteolytic disease and the associated skeletal related events in metastatic disease. Whereas breast, lung cancer and multiple myeloma typically result in osteolytic lesions, metastasis to the bone in prostate cancer initially has an osteoblastic appearance in which increased bone forming activity results in 'woven bone' which is different from typical lamellar structure of normal bone. During disease progression bone lesions display a significant osteolytic component as well as high serum levels of bone resorption and suggests that anti-resorptive therapy may be useful. Bisphosphonates have been shown to inhibit the formation of osteolytic lesions and reduced the number of skeletal-related events only in men with hormone-refractory metastatic prostate cancer but at this point their effect on osteoblastic lesions is controversial and bisphosphonates have not been beneficial in preventing bone metastasis or hormone responsive prostate cancer to date. The effect of anti-resorptive agents in mixed osteolytic/osteoblastic prostate cancer is still being studied in the clinic (Choueiri, M. B., et al., Cancer Metastasis Rev. 25 (2006) 601-609; Vessella, R. L. and Corey, E., Clin. Cancer Res. 12 (20 Pt 2) (2006) 6285s-6290s).

The third mechanism is based on the recent observation that tumor associated macrophages (TAM) found in solid tumors of the breast, prostate, ovarian and cervical cancers correlated with poor prognosis (Bingle, L., et al., J. Pathol. 196 (2002) 254-265; Pollard, J. W., Nat. Rev. Cancer 4 (2004) 71-78). Macrophages are recruited to the tumor by M-CSF and other chemokines. The macrophages can then contribute to tumor progression through the secretion of angiogenic factors, proteases and other growth factors and cytokines and may be blocked by inhibition of CSF-1R signaling. Recently it was shown by Zins et al (Zins, K., et al., Cancer Res. 67 (2007) 1038-1045) that expression of siRNA of Tumor necrosis factor alpha (TNF alpha), M-CSF or the combination of both would reduce tumor growth in a mouse xenograft model between 34% and 50% after intratumoral injection of the respective siRNA. SiRNA targeting the TNF alpha secreted by the human SW620 cells reduced mouse M-CSF levels and led to reduction of macrophages in the tumor. In addition treatment of MCF7 tumor xenografts with an antigen binding fragment directed against M-CSF did result in 40% tumor growth inhibition, reversed the resistance to chemotherapeutics and improved survival of the mice when given in combination with chemotherapeutics (Paulus, P., et al., Cancer Res. 66 (2006) 4349-4356).

TAMs are only one example of an emerging link between chronic inflammation and cancer. There is additional evidence for a link between inflammation and cancer as many chronic diseases are associated with an increased risk of cancer, cancers arise at sites of chronic inflammation, chemical mediators of inflammation are found in many cancers; deletion of the cellular or chemical mediators of inflammation inhibits development of experimental cancers and long-term use of anti-inflammatory agents reduce the risk of some cancers. A link to cancer exists for a number of inflammatory conditions among—those *H. pylori* induced gastritis for gastric cancer, Schistosomiasis for bladder cancer, HHVX for Kaposi's sarcoma, endometriosis for ovarian cancer and prostatitis for prostate cancer (Balkwill, F., et al., Cancer Cell 7 (2005) 211-217). Macrophages are key cells in chronic inflammation and respond differentially to their microenvironment. There are two types of macrophages that are considered extremes in a continuum of functional states: M1 macrophages are involved in Type 1 reactions. These reactions involve the activation by microbial products and consequent killing of pathogenic microorganisms that result in reactive oxygen intermediates. On the other end of the extreme are M2 macrophages involved in Type 2 reactions that promote cell proliferation, tune inflammation and adaptive immunity and promote tissue remodeling, angiogenesis and repair (Mantovani, A., et al., Trends Immunol. 25 (2004) 677-686). Chronic inflammation resulting in established neoplasia is usually associated with M2 macrophages. A pivotal cytokine that mediates inflammatory reactions is TNF alpha that true to its name can stimulate anti-tumor immunity and hemorrhagic necrosis at high doses but has also recently been found to be expressed by tumor cells and acting as a tumor promoter (Zins, K., et al., Cancer Res. 67 (2007) 1038-1045; Balkwill, F., Cancer Metastasis Rev. 25 (2006) 409-416). The specific role of macrophages with respect to the tumor still needs to be better understood including the potential spatial and temporal dependence on their function and the relevance to specific tumor types.

Thus one embodiment of the invention are the CSF-1R antibodies of the present invention for use in the treatment of cancer. The term "cancer" as used herein may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers. In one preferred embodiment such cancer is a breast cancer, colorectal cancer, melanoma, head and neck cancer, lung cancer or prostate cancer. In one preferred embodiment such cancer is a breast cancer, ovarian cancer, cervical cancer, lung cancer or prostate cancer. In one preferred embodiment such cancers are further characterized by CSF-1 or CSF-1R expression or overexpression. One further embodiment the invention are the CSF-1R antibodies of the present invention for use in the simultaneous treatment of primary tumors and new metastases.

Thus another embodiment of the invention are the CSF-1R antibodies of the present invention for use in the treatment of periodontitis, histiocytosis X, osteoporosis, Paget's disease of bone (PDB), bone loss due to cancer therapy, periprosthetic osteolysis, glucocorticoid-induced osteoporosis, rheumatoid arthritis, psiratic arthritis, osteoarthritis, inflammatory arthridies, and inflammation.

Rabello, D., et al., Biochem. Biophys. Res. Commun. 347 (2006) 791-796 has demonstrated that SNPs in the CSF1 gene exhibited a positive association with aggressive periodontitis: an inflammatory disease of the periodontal tissues that causes tooth loss due to resorption of the alveolar bone.

Histiocytosis X (also called Langerhans cell histiocytosis, LCH) is a proliferative disease of Langerhans dendritic cells that appear to differentiate into osteoclasts in bone and extra osseous LCH lesions. Langerhans cells are derived from circulating monocytes. Increased levels of M-CSF that have been measured in sera and lesions where found to correlate with disease severity (da Costa, C. E., et al., J. Exp. Med. 201 (2005) 687-693). The disease occurs primarily in a pediatric patient population and has to be treated with chemotherapy when the disease becomes systemic or is recurrent.

The pathophysiology of osteoporosis is mediated by loss of bone forming osteoblasts and increased osteoclast dependent bone resorption. Supporting data has been described by Cenci et al showing that an anti-M-CSF antibody injection preserves bone density and inhibits bone resorption in ovariectomized mice (Cenci, S., et al., J. Clin. Invest. 105 (2000) 1279-1287). Recently a potential link between postmenopausal bone loss due to estrogen deficiency was identified and found that the presence of TNF alpha producing T-cell affected bone metabolism (Roggia, C., et al., Minerva Med. 95 (2004) 125-132). A possible mechanism could be the induction of M-CSF by TNF alpha in vivo. An important role for M-CSF in TNF-alpha-induced osteoclastogenesis was confirmed by the effect of an antibody directed against M-CSF that blocked the TNF alpha induced osteolysis in mice and thereby making inhibitors of CSF-1R signaling potential targets for inflammatory arthritis (Kitaura, H., et al., J. Clin. Invest. 115 (2005) 3418-3427).

Paget's disease of bone (PDB) is the second most common bone metabolism disorder after osteoporosis in which focal abnormalities of increased bone turnover lead to complications such as bone pain, deformity, pathological fractures and deafness. Mutations in four genes have been identified that regulate normal osteoclast function and predispose individuals to PDB and related disorders: insertion mutations in TNFRSF11A, which encodes receptor activator of nuclear factor (NF) kappaB (RANK)—a critical regulator of osteoclast function, inactivating mutations of TNFRSF11B which encodes osteoprotegerin (a decoy receptor for RANK ligand), mutations of the sequestosome 1 gene (SQSTM1), which encodes an important scaffold protein in the NFkappaB pathway and mutations in the valosin-containing protein (VCP) gene. This gene encodes VCP, which has a role in targeting the inhibitor of NFkappaB for degradation by the proteasome (Daroszewska, A. and Ralston, S. H., Nat. Clin. Pract. Rheumatol. 2 (2006) 270-277). Targeted CSF-1R inhibitors provide an opportunity to block the deregulation of the RANKL signaling indirectly and add an additional treatment option to the currently used bisphosphonates.

Cancer therapy induced bone loss especially in breast and prostate cancer patients is an additional indication where a targeted CSF-1R inhibitor could prevent bone loss (Lester, J. E., et al., Br. J. Cancer 94 (2006) 30-35). With the improved prognosis for early breast cancer the long-term consequences of the adjuvant therapies become more important as some of the therapies including chemotherapy, irradiation, aromatase inhibitors and ovary ablation affect bone metabolism by decreasing the bone mineral density, resulting in increased risk for osteoporosis and associated fractures (Lester, J. E., et al., Br. J. Cancer 94 (2006) 30-35). The equivalent to adjuvant aromatase inhibitor therapy in breast cancer is androgen ablation therapy in prostate cancer which leads to loss of bone mineral density and significantly increases the risk of osteoporosis-related fractures (Stoch, S. A., et al., J. Clin. Endocrinol. Metab. 86 (2001) 2787-2791).

Targeted inhibition of CSF-1R signaling is likely to be beneficial in other indications as well when targeted cell types include osteoclasts and macrophages e.g. treatment of specific complications in response to joint replacement as a consequence of rheumatoid arthritis. Implant failure due to periprosthetic bone loss and consequent loosing of prostheses is a major complication of joint replacement and requires repeated surgery with high socioeconomic burdens for the individual patient and the health-care system. To date, there is no approved drug therapy to prevent or inhibit periprosthetic osteolysis (Drees, P., et al., Nat. Clin. Pract. Rheumatol. 3 (2007) 165-171).

Glucocorticoid-induced osteoporosis (GIOP) is another indication in which a CSF-1R inhibitor could prevent bone loss after longterm glucocorticocosteroid use that is given as a result of various conditions among those chronic obstructive pulmonary disease, asthma and rheumatoid arthritis (Guzman-Clark, J. R., et al., Arthritis Rheum. 57 (2007) 140-146; Feldstein, A. C., et al., Osteoporos. Int. 16 (2005) 2168-2174).

Rheumatoid arthritis, psioratic arthritis and inflammatory arthridities are in itself potential indications for CSF-1R signaling inhibitors in that they consist of a macrophage component and to a varying degree bone destruction (Ritchlin, C. T., et al., J. Clin. Invest. 111 (2003) 821-831). Osteoarthritis and rheumatoid arthritis are inflammatory autoimmune disease caused by the accumulation of macrophages in the connective tissue and infiltration of macrophages into the synovial fluid, which is at least partially mediated by M-CSF. Campbell, I., K., et al., J. Leukoc. Biol. 68 (2000) 144-150, demonstrated that M-CSF is produced by human-joint tissue cells (chondrocytes, synovial fibroblasts) in vitro and is found in synovial fluid of patients with rheumatoid arthritis, suggesting that it contributes to the synovial tissue proliferation and macrophage infiltration which is associated with the pathogenesis of the disease. Inhibition of CSF-1R signaling is likely to control the number of macrophages in the joint and alleviate the pain from the associated bone destruction. In order to minimize adverse effects and to further understand the impact of the CSF-1R signaling in these indications, one method is to specifically inhibit CSF-1R without targeting a myriad other kinases, such as Raf kinase.

Recent literature reports correlate increased circulating M-CSF with poor prognosis and atherosclerotic progression in chronic coronary artery disease (Saitoh, T., et al., J. Am. Coll. Cardiol. 35 (2000) 655-665; Ikonomidis, I., et al., Eur. Heart. J. 26 (2005) p. 1618-1624); M-CSF influences the atherosclerotic process by aiding the formation of foam cells (macrophages with ingested oxidized LDL) that express CSF-1R and represent the initial plaque (Murayama, T., et al., Circulation 99 (1999) 1740-1746).

Expression and signaling of M-CSF and CSF-1R is found in activated microglia. Microglia, which are resident macrophages of the central nervous system, can be activated by various insults, including infection and traumatic injury. M-CSF is considered a key regulator of inflammatory responses in the brain and M-CSF levels increase in HIV-1, encephalitis, Alzheimer's disease (AD) and brain tumors. Microgliosis as a consequence of autocrine signaling by M-CSF/CSF-1R results in induction of inflammatory cytokines and nitric oxides being released as demonstrated by e.g. using an experimental neuronal damage model (Hao, A. J., et al., Neuroscience 112 (2002) 889-900; Murphy, G. M., Jr., et al., J. Biol. Chem. 273 (1998) 20967-20971). Microglia that have increased expression of CSF-1R are found to surround plaques in AD and in the amyloid precursor protein V717F transgenic mouse model of AD (Murphy, G. M., Jr., et al., Am. J. Pathol. 157 (2000) 895-904). On the other hand op/op mice with fewer microglia in the brain resulted in fibrilar deposition of A-beta and neuronal loss compared to normal control suggesting that microglia do have a neuroprotective function in the development of AD lacking in the op/op mice (Kaku, M., et al., Brain Res. Brain Res. Protoc. 12 (2003) 104-108).

Expression and signaling of M-CSF and CSF-1R is associated with inflammatory bowel disease (IBD) (WO 2005/046657). The term "inflammatory bowel disease" refers to serious, chronic disorders of the intestinal tract characterized by chronic inflammation at various sites in the gastrointestinal tract, and specifically includes ulcerative colitis (UC) and Crohn's disease.

Thus another embodiment of the invention are the CSF-1R antibodies of the present invention for use in the treatment of periodontitis, histiocytosis X, osteoporosis, Paget's disease of bone (PDB), bone loss due to cancer therapy, periprosthetic osteolysis, glucocorticoid-induced osteoporosis, rheumatoid arthritis, psiratic arthritis, osteoarthritis, inflammatory arthridities, and inflammation.

The invention comprises the combination therapy with an antibody binding to human CSF-1R being characterized by the above mentioned epitope binding properties or alternatively by the above mentioned amino acid sequences and amino acid sequence fragments with an TLR9 agonist for the treatment of cancer.

The invention comprises the combination therapy with an antibody binding to human CSF-1R being characterized by the above mentioned epitope binding properties or alternatively by the above mentioned amino acid sequences and amino acid sequence fragments with an TLR9 agonist for the treatment of bone loss.

The invention comprises the combination therapy with an antibody binding to human CSF-1R being characterized by the above mentioned epitope binding properties or alternatively by the above mentioned amino acid sequences and amino acid sequence fragments with an TLR9 agonist for the prevention or treatment of metastasis.

The invention comprises the combination therapy with an antibody binding to human CSF-1R being characterized by the above mentioned epitope binding properties or alternatively by the above mentioned amino acid sequences and amino acid sequence fragments with an TLR9 agonist for treatment of inflammatory diseases.

The invention comprises the use of an antibody characterized in comprising the antibody binding to human CSF-1R being characterized by the above mentioned epitope binding properties or alternatively by the above mentioned amino acid sequences and amino acid sequence fragments for the combination treatment of cancer as described herein or alternatively for the manufacture of a medicament for the combination treatment of cancer with an TLR9 agonist as described herein.

The invention comprises the use of an antibody characterized in comprising the antibody binding to human CSF-1R being characterized by the above mentioned epitope binding properties or alternatively by the above mentioned amino acid sequences and amino acid sequence fragments for the combination treatment as described herein of bone loss or alternatively for the manufacture of a medicament for the combination treatment of bone loss with an TLR9 agonist as described herein.

The invention comprises the use of an antibody characterized in comprising the antibody binding to human CSF-1R being characterized by the above mentioned epitope binding properties or alternatively by the above mentioned amino acid sequences and amino acid sequence fragments for the prevention or treatment of metastasis with the combination as described herein or alternatively for the manufacture of a medicament for the prevention or treatment of metastasis with the combination with an TLR9 agonist as described herein.

The invention comprises the use of an antibody characterized in comprising the antibody binding to human CSF-1R being characterized by the above mentioned epitope binding properties or alternatively by the above mentioned amino acid sequences and amino acid sequence fragments for combination treatment of inflammatory diseases as described herein or alternatively for the manufacture of a medicament for the combination treatment of inflammatory diseases with an TLR9 agonist as described herein.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or E. coli cells, and the antibody is recovered from the cells (from the supernatant or after cells lysis).

Recombinant production of antibodies is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The antibodies may be present in whole cells, in a cell lysate, or in a partially purified, or substantially pure form. Purification is performed in order to eliminate other cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987).

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; Norderhaug, L., et al., J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199.

Nucleic acid molecules encoding amino acid sequence variants of anti-CSF-1R antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-CSF-1R antibody.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

In another aspect, the present invention provides a composition, e.g. a pharmaceutical composition, containing one or a combination of monoclonal antibodies, or the antigen-binding portion thereof, of the present invention, formulated together with a pharmaceutically acceptable carrier.

As used herein, "pharmaceutically acceptable carrier" includes any and all solvents, dispersion media, coatings, antibacterial and antifungal agents, isotonic and absorption/resorption delaying agents, and the like that are physiologically compatible. Preferably, the carrier is suitable for injection or infusion.

A composition of the present invention can be administered by a variety of methods known in the art. As will be appreciated by the skilled artisan, the route and/or mode of administration will vary depending upon the desired results.

Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient (effective amount). The selected dosage level will depend upon a variety of pharmacokinetic factors including the activity of the particular compositions of the present invention employed, or the ester, salt or amide thereof, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

The term "a method of treating" or its equivalent, when applied to, for example, cancer refers to a procedure or course of action that is designed to reduce or eliminate the number of cancer cells in a patient, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of a patient, is nevertheless deemed to induce an overall beneficial course of action.

The terms "administered in combination with" or "co-administration", "co-administering" or "a combination" refer to the administration of the anti-CSF-1R, and the TLR 9 agonist e.g. as separate formulations/applications (or as one single formulation/application). The co-administration can be simultaneous or sequential in either order, wherein preferably there is a time period while both (or all) active agents simultaneously exert their biological activities. Said antibody and said TLR9 agonist are co-administered either simultaneously or sequentially (e.g. intravenous (i.v.) through a continuous infusion. When both therapeutic agents are co-administered sequentially the dose is administered either on the same day in two separate administrations, or one of the agents is administered on day 1 and the second is co-administered on day 2 to day 7, preferably on day 2 to 4. Thus in one embodiment the term "sequentially" means within 7 days after the dose of the first component, preferably within 4 days after the dose of the first component; and the term "simultaneously" means at the same time. The terms "co-administration" with respect to the maintenance doses of anti-CSF-1R antibody mean that the maintenance doses can be either co-administered simultaneously, if the treatment cycle is appropriate for both drugs, e.g. every week. Or the further agent is e.g. administered e.g. every first to third day and said antibody is administered every week. Or the maintenance doses are co-administered sequentially, either within one or within several days.

It is self-evident that the antibodies are administered to the patient in a "therapeutically effective amount" (or simply "effective amount") which is the amount of the respective compound or combination that will elicit the biological or medical response of a tissue, system, animal or human that is being sought by the researcher, veterinarian, medical doctor or other clinician.

The amount of co-administration and the timing of co-administration will depend on the type (species, gender, age, weight, etc.) and condition of the patient being treated and the severity of the disease or condition being treated. Said anti-CSF-1R antibody and further agent are suitably co-administered to the patient at one time or over a series of treatments e.g. on the same day or on the day after.

Depending on the type and severity of the disease, about 0.1 mg/kg to 50 mg/kg (e.g. 0.1-20 mg/kg) of said anti-CSF-1R antibody; is an initial candidate dosage for co-administration of both drugs to the patient. The invention comprises the use of the antibodies according to the invention for the treatment of a patient suffering from cancer, especially from colon, lung or pancreas cancer.

Depending on the type and severity of the disease, about 0.1 mg/kg to 50 mg/kg (e.g. 0.1-20 mg/kg) of said anti-CSF-1R antibody; is an initial candidate dosage for co-administration of both drugs to the patient. The invention comprises the use of the antibodies according to the invention for the treatment of a patient suffering from cancer, especially from colon, lung or pancreas cancer.

In addition to the anti-CSF-1R antibody in combination with the TLR9 agonist also a chemotherapeutic agent can be administered.

In one embodiment such additional chemotherapeutic agents, which may be administered with anti-CSF-1R antibody and the TLR9 agonist, include, but are not limited to, anti-neoplastic agents including alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); Temodal™ (temozolamide), ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil (5FU), fluorodeoxyuridine, gemcitabine, cytosine arabinoside (AraC, cytarabine), 5-azacytidine, 2,2'-difluorodeoxycytidine, purine analogs such as 6-merca.rho.topurine, 6-thioguamne, azathioprine, T-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; pipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as oxaliplatin, cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o, p-DDD) and aminoglutethimide; hormones and antagonists including adrenocorticosteroid antagonists such as prednisone and equivalents, dexamethasone and aminoglutethimide; Gemzar™ (gemcitabine), progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide. Therapies targeting epigenetic mechanism including, but not limited to, histone deacetylase inhibitors, demethylating agents (e.g., Vidaza) and release of transcriptional repression (ATRA) therapies can also be combined with the antigen binding proteins. In one embodiment the chemotherapeutic agent is selected from the group consisting of taxanes (like e.g. paclitaxel (Taxol), docetaxel (Taxotere), modified paclitaxel (e.g., Abraxane and Opaxio), doxorubicin, sunitinib (Sutent), sorafenib (Nexavar), and other multikinase inhibitors, oxaliplatin, cisplatin and carboplatin, etoposide, gemcitabine, and vinblastine. In one embodiment the chemotherapeutic agent is selected from the group consisting of taxanes (like e.g. taxol (paclitaxel), docetaxel (Taxotere), modified paclitaxel (e.g. Abraxane and Opaxio). In one embodiment, the additional chemotherapeutic agent is selected from 5-fluorouracil (5-FU), leucovorin, irinotecan, or oxaliplatin. In one embodiment the chemotherapeutic agent is 5-fluorouracil, leucovorin and irinotecan (FOLFIRI). In one embodiment the chemotherapeutic agent is 5-fluorouracil, and oxaliplatin (FOLFOX).

Specific examples of combination therapies with additional chemotherapeutic agents include, for instance, therapies taxanes (e.g., docetaxel or paclitaxel) or a modified paclitaxel (e.g., Abraxane or Opaxio), doxorubicin), capecitabine and/or bevacizumab (Avastin) for the treatment of breast cancer; therapies with carboplatin, oxaliplatin, cisplatin, paclitaxel, doxorubicin (or modified doxorubicin (Caelyx or Doxil)), or topotecan (Hycamtin) for ovarian cancer, the therapies with a multi-kinase inhibitor, MKI, (Sutent, Nexavar, or 706) and/or doxorubicin for treatment of kidney cancer; therapies with oxaliplatin, cisplatin and/or radiation for the treatment of squamous cell carcinoma; therapies with taxol and/or carboplatin for the treatment of lung cancer.

Therefore, in one embodiment the additional chemotherapeutic agent is selected from the group of taxanes (docetaxel or paclitaxel or a modified paclitaxel (Abraxane or Opaxio), doxorubicin, capecitabine and/or bevacizumab for the treatment of breast cancer.

In one embodiment the CSF-1R antibody/TLR9 agonist combination therapy is no chemotherapeutic agents are administered.

The invention comprises also a method for the treatment of a patient suffering from such disease.

The invention further provides a method for the manufacture of a pharmaceutical composition comprising an effective amount of an antibody according to the invention together with a pharmaceutically acceptable carrier and the use of the antibody according to the invention for such a method.

The invention further provides the use of an antibody according to the invention in an effective amount for the manufacture of a pharmaceutical agent, preferably together with a pharmaceutically acceptable carrier, for the treatment of a patient suffering from cancer.

The invention also provides the use of an antibody according to the invention in an effective amount for the manufacture of a pharmaceutical agent, preferably together with a pharmaceutically acceptable carrier, for the treatment of a patient suffering from cancer.

The following examples, sequence listing and figures are provided to aid the understanding of the present invention, the true scope of which is set forth in the appended claims. It is understood that modifications can be made in the procedures set forth without departing from the spirit of the invention.

Description of the Sequences
SEQ ID NO: 1 heavy chain CDR3, Mab 2F11
SEQ ID NO: 2 heavy chain CDR2, Mab 2F11
SEQ ID NO: 3 heavy chain CDR1, Mab 2F11
SEQ ID NO: 4 light chain CDR3, Mab 2F11
SEQ ID NO: 5 light chain CDR2, Mab 2F11
SEQ ID NO: 6 light chain CDR1, Mab 2F11
SEQ ID NO: 7 heavy chain variable domain, Mab 2F11
SEQ ID NO: 8 light chain variable domain, Mab 2F11
SEQ ID NO: 9 heavy chain CDR3, Mab 2E10
SEQ ID NO: 10 heavy chain CDR2, Mab 2E10
SEQ ID NO: 11 heavy chain CDR1, Mab 2E10
SEQ ID NO: 12 light chain CDR3, Mab 2E10
SEQ ID NO: 13 light chain CDR2, Mab 2E10
SEQ ID NO: 14 light chain CDR1, Mab 2E10
SEQ ID NO: 15 heavy chain variable domain, Mab 2E10
SEQ ID NO: 16 light chain variable domain, Mab 2E10
SEQ ID NO: 17 heavy chain CDR3, hMab 2F11-c11
SEQ ID NO: 18 heavy chain CDR2, hMab 2F11-c11
SEQ ID NO: 19 heavy chain CDR1, hMab 2F11-c11
SEQ ID NO: 20 light chain CDR3, hMab 2F11-c11
SEQ ID NO: 21 light chain CDR2, hMab 2F11-c11
SEQ ID NO: 22 light chain CDR1, hMab 2F11-c11
SEQ ID NO: 23 heavy chain variable domain, hMab 2F11-c11
SEQ ID NO: 24 light chain variable domain, hMab 2F11-c11
SEQ ID NO: 25 heavy chain CDR3, hMab 2F11-d8
SEQ ID NO: 26 heavy chain CDR2, hMab 2F11-d8
SEQ ID NO: 27 heavy chain CDR1, hMab 2F11-d8
SEQ ID NO: 28 light chain CDR3, hMab 2F11-d8
SEQ ID NO: 29 light chain CDR2, hMab 2F11-d8
SEQ ID NO: 30 light chain CDR1, hMab 2F11-d8
SEQ ID NO: 31 heavy chain variable domain, hMab 2F11-d8
SEQ ID NO: 32 light chain variable domain, hMab 2F11-d8
SEQ ID NO: 33 heavy chain CDR3, hMab 2F11-e7
SEQ ID NO: 34 heavy chain CDR2, hMab 2F11-e7
SEQ ID NO: 35 heavy chain CDR1, hMab 2F11-e7
SEQ ID NO: 36 light chain CDR3, hMab 2F11-e7
SEQ ID NO: 37 light chain CDR2, hMab 2F11-e7
SEQ ID NO: 38 light chain CDR1, hMab 2F11-e7
SEQ ID NO: 39 heavy chain variable domain, hMab 2F11-e7
SEQ ID NO: 40 light chain variable domain, hMab 2F11-e7
SEQ ID NO: 41 heavy chain CDR3, hMab 2F11-f12
SEQ ID NO: 42 heavy chain CDR2, hMab 2F11-f12
SEQ ID NO: 43 heavy chain CDR1, hMab 2F11-f12
SEQ ID NO: 44 light chain CDR3, hMab 2F11-f12
SEQ ID NO: 45 light chain CDR2, hMab 2F11-f12
SEQ ID NO: 46 light chain CDR1, hMab 2F11-f12
SEQ ID NO: 47 heavy chain variable domain, hMab 2F11-f12
SEQ ID NO: 48 light chain variable domain, hMab 2F11-f12
SEQ ID NO: 49 heavy chain CDR3, hMab 2F11-g1
SEQ ID NO: 50 heavy chain CDR2, hMab 2F11-g1
SEQ ID NO: 51 heavy chain CDR1, hMab 2F11-g1
SEQ ID NO: 52 light chain CDR3, hMab 2F11-g1
SEQ ID NO: 53 light chain CDR2, hMab 2F11-g1
SEQ ID NO: 54 light chain CDR1, hMab 2F11-g1
SEQ ID NO: 55 heavy chain variable domain, hMab 2F11-g1
SEQ ID NO: 56 light chain variable domain, hMab 2F11-g1
SEQ ID NO: 57 human kappa light chain constant region
SEQ ID NO: 58 human heavy chain constant region derived from IgG1
SEQ ID NO: 59 human heavy chain constant region derived from IgG1 mutated on L234A and L235A
SEQ ID NO: 60 human heavy chain constant region derived from IgG4
SEQ ID NO: 61 human heavy chain constant region derived from IgG4 mutated on S228P
SEQ ID NO: 62 human wildtype CSF-1R (wt CSF-1R)
SEQ ID NO: 63 human mutant CSF-1R L301S Y969F
SEQ ID NO: 64 human CSF-1R Extracellular Domain (domains D1-D5)
SEQ ID NO: 65 human CSF-1R fragment delD4
SEQ ID NO: 66 human CSF-1R fragment domains D1-D3
SEQ ID NO: 67 signal peptide
SEQ ID NO: 68 Primer
SEQ ID NO: 69 heavy chain CDR3, Mab 1G10
SEQ ID NO: 70 heavy chain CDR2, Mab 1G10
SEQ ID NO: 71 heavy chain CDR1, Mab 1G10
SEQ ID NO: 72 light chain CDR3, Mab 1G10
SEQ ID NO: 73 light chain CDR2, Mab 1G10
SEQ ID NO: 74 light chain CDR1, Mab 1G10
SEQ ID NO: 75 heavy chain variable domain, Mab 1G10
SEQ ID NO: 76 light chain variable domain, Mab 1G10
SEQ ID NO: 77 heavy chain CDR3, Mab 2H7
SEQ ID NO: 78 heavy chain CDR2, Mab 2H7
SEQ ID NO: 79 heavy chain CDR1, Mab 2H7
SEQ ID NO: 80 light chain CDR3, Mab 2H7
SEQ ID NO: 81 light chain CDR2, Mab 2H7
SEQ ID NO: 82 light chain CDR1, Mab 2H7
SEQ ID NO: 83 heavy chain variable domain, Mab 2H7
SEQ ID NO: 84 light chain variable domain, Mab 2H7
SEQ ID NO: 85 human CSF-1R fragment domains D4-D5
SEQ ID NO: 86 human CSF-1
SEQ ID NO: 87 human IL-34
SEQ ID NO: 88 human toll-like receptor 9 (TLR9)
SEQ ID NO: 89 TLR9 agonist CpG ODN 2216
SEQ ID NO: 90 TLR9 agonist CpG ODN PB4
SEQ ID NO: 91 TLR9 agonist CpG ODN 1002
SEQ ID NO: 92 TLR9 agonist CpG-7909 (CpG 2006, PF-3512676, Agatolimod)
SEQ ID NO: 93 TLR9 agonist CpG-685 (GNKG168; CpG ODN; SBI Biotech)
SEQ ID NO: 94 TLR9 agonist CpG-684
SEQ ID NO: 95 TLR9 agonist CpG-28

In the following embodiment of the invention are described:

1. An antibody which binds to human CSF-1R wherein the antibody is administered in combination with a Toll-like receptor 9 (TLR9) agonist for use in the treatment of cancer.
2. Use of a combination of
   i) an antibody which binds to human CSF-1R, and
   ii) a Toll-like receptor 9 (TLR9) agonist for the manufacture of a medicament for use in the treatment of cancer.
3. The antibody or use according to embodiments 1 or 2, wherein the cancer is further characterized by CSF-1R expression or overexpression.
4. The antibody or use according to any one of embodiments 1 or 2, wherein the cancer is a breast cancer, colorectal cancer, melanoma, head and neck cancer, lung cancer or prostate cancer.
5. An antibody which binds to human CSF-1R characterized in binding to the (dimerization) domains D4 to D5 (SEQ ID No: 85) of the extracellular domain of human CSF-1R for use in
   a) the inhibition of cell proliferation in CSF-1R ligand-dependent and/or CSF-1 ligand-independent CSF-1R expressing tumor cells;
   b) the inhibition of cell proliferation of tumors with CSF-1R ligand-dependent and/or CSF-1R ligand-independent CSF-1R expressing macrophage infiltrate;
   c) the inhibition of cell survival (in CSF-1R ligand-dependant and/or CSF-1R ligand-independent) CSF-1R expressing monocytes and macrophages; and/or
   d) the inhibition of cell differentiation (in CSF-1R ligand-dependent and/or CSF-1R ligand-independent) CSF-1R expressing monocytes into macrophages,
   wherein the antibody is administered in combination with a TLR9 agonist.
6. Use of a combination of
   i) an antibody which binds to the (dimerization) domains D4 to D5 (SEQ ID No: 85) of the extracellular domain of human CSF-1R, and
   ii) a Toll-like receptor 9 (TLR9) agonist
   for the manufacture of a medicament for use in
      a) the inhibition of cell proliferation in CSF-1R ligand-dependent and/or CSF-1 ligand-independent CSF-1R expressing tumor cells;
      b) the inhibition of cell proliferation of tumors with CSF-1R ligand-dependent and/or CSF-1R ligand-independent CSF-1R expressing macrophage infiltrate;
      c) the inhibition of cell survival (in CSF-1R ligand-dependant and/or CSF-1R ligand-independent) CSF-1R expressing monocytes and macrophages; and/or
      d) the inhibition of cell differentiation (in CSF-1R ligand-dependent and/or CSF-1R ligand-independent) CSF-1R expressing monocytes into macrophages.
7. An antibody which binds to human CSF-1R, for use in the treatment of a patient having a CSF-1R expressing tumor or having a tumor with CSF-1R expressing macrophage infiltrate, wherein the tumor is characterized by an increase of CSF-1R ligand and wherein the anti-CSF-1R antibody is administered in combination with a TLR9 agonist.
8. Use of a combination of
   i) an antibody which binds to human CSF-1R, and
   ii) a Toll-like receptor 9 (TLR9) agonist
   for the manufacture of a medicament for use in for use in the treatment of a patient having a CSF-1R expressing tumor or having a tumor with CSF-1R expressing macrophage infiltrate, wherein the tumor is characterized by an increase of CSF-1R ligand.
9. The antibody or use according to any one of embodiments 1 or 8 wherein the TLR9 agonist is characterized by induction of IFN-alpha, IL-6, and/or IL-12 in plasmacytoid dendritic cells (pDCs).
10. The antibody or use according to any one of embodiments 1 to 8, wherein the TLR9 agonist is a oligodeoxynucleotides containing cytosine-phosphate-guanosine (CpG) motifs (CpG ODNs).
11. The antibody or use according to any one of embodiments 1 to 10 wherein the antibody is characterized in binding to the domains D4 to D5 (SEQ ID No: 85) of the extracellular domain of human CSF-1R.
12. The antibody according any one of the preceding embodiments, wherein the antibody is characterized in that the antibody does not bind to human CSF-1R fragment delD4 (SEQ ID NO: 65).
13. The antibody according any one of the preceding embodiments, characterized in that
   a) the heavy chain variable domain is SEQ ID NO:7 and the light chain variable domain is SEQ ID NO:8,
   b) the heavy chain variable domain is SEQ ID NO:15 and the light chain variable domain is SEQ ID NO:16;
   c) the heavy chain variable domain is SEQ ID NO:75 and the light chain variable domain is SEQ ID NO:76;
   d) the heavy chain variable domain is SEQ ID NO:83 and the light chain variable domain is SEQ ID NO:84;
   e) the heavy chain variable domain is SEQ ID NO:23 and the light chain variable domain is SEQ ID NO:24, or
   f) the heavy chain variable domain is SEQ ID NO:31 and the light chain variable domain is SEQ ID NO:32, or
   g) the heavy chain variable domain is SEQ ID NO:39 and the light chain variable domain is SEQ ID NO:40, or
   h) the heavy chain variable domain is SEQ ID NO:47 and the light chain variable domain is SEQ ID NO:48, or
   i) the heavy chain variable domain is SEQ ID NO:55 and the light chain variable domain is SEQ ID NO:56.
14. The antibody according any one of the preceding embodiments, characterized in that
   a) the heavy chain variable domain comprises a CDR3 region of SEQ ID NO: 1, a CDR2 region of SEQ ID NO: 2, and a CDR1 region of SEQ ID NO:3, and the light chain variable domain comprises a CDR3 region of SEQ ID NO: 4, a CDR2 region of SEQ ID NO:5, and a CDR1 region of SEQ ID NO:6, or
   b) the heavy chain variable domain comprises a CDR3 region of SEQ ID NO: 9, a CDR2 region of SEQ ID NO: 10, and a CDR1 region of SEQ ID NO: 11, and the light chain variable domain comprises a CDR3 region of SEQ ID NO:12, a CDR2 region of SEQ ID NO: 13, and a CDR1 region of SEQ ID NO: 14, or
   c) the heavy chain variable domain comprises a CDR3 region of SEQ ID NO: 17, a CDR2 region of SEQ ID NO: 18, and a CDR1 region of SEQ ID NO:19, and the light chain variable domain comprises a CDR3 region of SEQ ID NO: 20, a CDR2 region of SEQ ID NO:21, and a CDR1 region of SEQ ID NO:22, or
   d) the heavy chain variable domain comprises a CDR3 region of SEQ ID NO: 25, a CDR2 region of SEQ ID NO: 26, and a CDR1 region of SEQ ID NO: 27, and the light chain variable domain comprises a CDR3 region of SEQ ID NO:28, a CDR2 region of SEQ ID NO: 29, and a CDR1 region of SEQ ID NO: 30, or
   e) the heavy chain variable domain comprises a CDR3 region of SEQ ID NO: 33, a CDR2 region of SEQ ID NO: 34, and a CDR1 region of SEQ ID NO: 35, and the light chain variable domain comprises a CDR3 region of SEQ ID NO:36, a CDR2 region of SEQ ID NO: 37, and a CDR1 region of SEQ ID NO: 38, or
   f) the heavy chain variable domain comprises a CDR3 region of SEQ ID NO:41, a CDR2 region of SEQ ID NO: 42, and a CDR1 region of SEQ ID NO:43, and the light chain variable domain comprises a CDR3 region of SEQ ID NO: 44, a CDR2 region of SEQ ID NO:45, and a CDR1 region of SEQ ID NO:46, or g) the heavy chain variable domain comprises a CDR3 region of SEQ ID NO: 49, a CDR2 region of SEQ ID NO: 50, and a CDR1 region of SEQ ID NO: 51, and the light chain variable domain comprises a CDR3 region of SEQ ID NO:52, a CDR2 region of SEQ ID NO: 53, and a CDR1 region of SEQ ID NO: 54; or h) the heavy chain variable domain comprises a CDR3 region of SEQ ID NO:69, a CDR2 region of SEQ ID NO: 70, and a CDR1 region of SEQ ID NO:71, and the light chain variable domain comprises a CDR3 region of SEQ ID NO: 72, a CDR2 region of SEQ ID NO:73, and a CDR1 region of SEQ ID NO:74, or i) the heavy chain variable domain comprises a CDR3 region of SEQ ID NO: 77, a CDR2 region of SEQ ID NO: 78, and a CDR1 region of SEQ ID NO: 79, and the light chain variable domain comprises a CDR3 region of SEQ ID NO:80, a CDR2 region of SEQ ID NO: 81, and a CDR1 region of SEQ ID NO: 82.

15. The antibody according any one of the preceding embodiments, characterized in that said antibody is of human IgG1 subclass or is of human IgG4 subclass.

16. A method of treatment comprising administering to a patient suffering from cancer an effective amount of an antibody which binds to human CSF-1R wherein the antibody is administered in combination with a Toll-like receptor 9 (TLR9) agonist.

17. The method according to embodiment 16, wherein the cancer is further characterized by CSF-1R expression or overexpression.

18. The method according to embodiment 16, wherein the cancer is a breast cancer, colorectal cancer, melanoma, head and neck cancer, lung cancer or prostate cancer.

19. A method comprising administering an effective amount of an antibody which binds to human CSF-1R and is characterized in binding to the (dimerization) domains D4 to D5 (SEQ ID No: 85) of the extracellular domain of human CSF-1R for use in a) the inhibition of cell proliferation in CSF-1R ligand-dependent and/or CSF-1 ligand-independent CSF-1R expressing tumor cells;

b) the inhibition of cell proliferation of tumors with CSF-1R ligand-dependent and/or CSF-1R ligand-independent CSF-1R expressing macrophage infiltrate;

c) the inhibition of cell survival (in CSF-1R ligand-dependant and/or CSF-1R ligand-independent) CSF-1R expressing monocytes and macrophages; and/or d) the inhibition of cell differentiation (in CSF-1R ligand-dependent and/or CSF-1R ligand-independent) CSF-1R expressing monocytes into macrophages, wherein the antibody is administered in combination with an effective amount of a TLR9 agonist.

20. A method of treatment comprising administering an effective amount of an antibody which binds to human CSF-1R, for use in the treatment of a patient having a CSF-1R expressing tumor or having a tumor with CSF-1R expressing macrophage infiltrate, wherein the tumor is characterized by an increase of CSF-1R ligand and wherein the anti-CSF-1R antibody is administered in combination with an effective amount of a TLR9 agonist.

The following examples, sequence listing and figures are provided to aid the understanding of the present invention, the true scope of which is set forth in the appended claims. It is understood that modifications can be made in the procedures set forth without departing from the spirit of the invention.

EXAMPLES

Example 1

Generation of a Hybridoma Cell Line Producing Anti-CSF-1R Antibodies

Immunization Procedure of NMRI Mice

NMRI mice were immunized with an expression vector pDisplay™ (Invitrogen, USA) encoding the extracellular domain of huCSF-1R by utilizing electroporation. Every mouse was 4 times immunized with 100 µg DNA. When serum titers of anti-huCSF-1R were found to be sufficient, mice were additionally boosted once with 50 µg of a 1:1 mixture huCSF-1R ECD/huCSF-1R ECDhuFc chimera in 200 µl PBS intravenously (i.v.) 4 and 3 days before fusion.

Antigen Specific ELISA

Anti-CSF-1R titers in sera of immunized mice were determined by antigen specific ELISA. 0.3 µg/ml huCSF-1R-huFc chimera (soluble extracellular domain) was captured on a streptavidin plate (MaxiSorb; MicroCoat, DE, Cat. No. 11974998/MC1099) with 0.1 mg/ml biotinylated anti Fcγ (Jackson ImmunoResearch, Cat. No. 109-066-098) and horse radish peroxidase (HRP)-conjugated F(ab')$_2$ anti-mouse IgG (GE Healthcare, UK, Cat. No. NA9310V) diluted 1/800 in PBS/0.05% Tween20/0.5% BSA was added. Sera from all taps were diluted 1/40 in PBS/0.05% Tween20/0.5% BSA and serially diluted up to 1/1638400. Diluted sera were added to the wells. Pre-tap serum was used as negative control. A dilution series of mouse anti-human CSF-1R Mab3291 (R&D Systems, UK) from 500 ng/ml to 0.25 ng/ml was used as positive control. All components were incubated together for 1.5 hours, Wells were washed 6 times with PBST (PBS/0.2% Tween20) and assays were developed with freshly prepared ABTS® solution (1 mg/ml) (ABTS: 2,2'-azino bis(3-ethylbenzthiazoline-6-sulfonic acid) for 10 minutes at RT. Absorbance was measured at 405 nm.

Hybridoma Generation

The mouse lymphocytes can be isolated and fused with a mouse myeloma cell line using PEG based standard protocols to generate hybridomas. The resulting hybridomas are then screened for the production of antigen-specific antibodies. For example, single cell suspensions of splenic derived lymphocytes from immunized mice are fused to Ag8 non-secreting mouse myeloma cells P3X63Ag8.653 (ATCC, CRL-1580) with 50% PEG. Cells are plated at approximately $10^4$ in flat bottom 96 well micro titer plate, followed by about two weeks incubation in selective medium. Individual wells are then screened by ELISA for human anti-CSF-1R monoclonal IgM and IgG antibodies. Once extensive hybridoma growth occurs, the antibody secreting hybridomas are replated, screened again, and if still positive for human IgG, anti-CSF-1R monoclonal antibodies, can be subcloned by FACS. The stable subclones are then cultured in vitro to produce antibody in tissue culture medium for characterization. Antibodies according to the invention could be selected using the determination of the binding of anti-CSF-1R antibodies to human CSF-1R fragment delD4 and to human CSF-1R Extracellular Domain (CSF-1R-ECD) as described in Example 4, as well as the determination of growth inhibition of NIH3T3 cells transfected with wildtype CSF-1R (ligand dependent signalling) or mutant CSF-1R L301S Y969F (ligand independent signalling) under treatment with anti-CSF-1R monoclonal antibodies as described in Example 5.

Culture of Hybridomas

Generated muMAb hybridomas were cultured in RPMI 1640 (PAN—Catalogue No. (Cat. No.) PO4-17500) supplemented with 2 mM L-glutamine (GIBCO—Cat. No. 35050-038), 1 mM Na-Pyruvat (GIBCO—Cat. No. 11360-039), 1×NEAA (GIBCO—Cat. No. 11140-035), 10% FCS (PAA—Cat. No. A15-649), 1× Pen Strep (Roche—Cat. No. 1074440), 1× Nutridoma CS (Roche—Cat. No. 1363743), 50 μM Mercaptoethanol (GIBCO—Cat. No. 31350-010) and 50 U/ml IL 6 mouse (Roche—Cat. No. 1 444 581) at 37° C. and 5% $CO_2$. Some of the resulting mouse antibodies have been humanized (e.g. Mab 2F11) and been expressed recombinantly.

Example 2

Inhibition of CSF-1 Binding to CSF-1R

ELISA

By setting-up this assay to first allow for anti-CSF-1R antibody binding to the CSF-1R-ECD followed by detection of ligand not bound to the receptor both-ligand displacing antibodies and dimerization inhibitor anti-CSF-1R antibodies—can be tested. The test was performed on 384 well microtiter plates (MicroCoat, DE, Cat. No. 464718) at RT. After each incubation step plates were washed 3 times with PBST.

At the beginning, plates were coated with 0.5 mg/ml goat F(ab')2 biotinylated anti Fcγ (Jackson ImmunoResearch, Cat. No. 109-006-170) for 1 hour (h).

Thereafter the wells were blocked with PBS supplemented with 0.2% Tween®-20 and 2% BSA (Roche Diagnostics GmbH, DE) for 0.5 h. 75 ng/ml of huCSF-1R-huFc chimera (which forms the dimeric soluble extracellular domain of huCSF-1R) was immobilized to plate for 1 h. Then dilutions of purified antibodies in PBS/0.05% Tween20/0.5% BSA were incubated for 1 h. After adding a mixture of 3 ng/ml hu CSF-1 (active 149 aa fragment of human CSF-1 (aa 33-181 of SEQ ID NO: 86); Biomol, DE, Cat. No. 60530), 50 ng/ml biotinylated anti CSF-1 clone BAF216 (R&D Systems, UK) and 1:5000 diluted streptavidin HRP (Roche Diagnostics GmbH, DE, Cat. No. 11089153001) for 1 h the plates were washed 6 times with PBST. Anti CSF-1R SC 2-4A5 (Santa Cruz Biotechnology, US), which inhibits the ligand-receptor interaction, was used as positive control. Plates were developed with freshly prepared BM Blue® POD substrate solution (BM Blue®: 3,3'-5,5'-Tetramethylbenzidine, Roche Diagnostics GmbH, DE, Cat. No. 11484281001) for 30 minutes at RT. Absorbance was measured at 370 nm. A decrease of absorbance is found, if the anti-CSF-1R antibody causes a release of CSF-1 from the dimeric complex. All anti-CSF-1R antibodies showed significant inhibition of the CSF-1 interaction with CSF-1R (see Table 1). Anti CSF-1R SC 2-4A5 (Santa Cruz Biotechnology, US see also Sherr, C. J. et al., Blood 73 (1989) 1786-1793), which inhibits the ligand-receptor interaction, was used as reference control.

TABLE 1

Calculated IC50 values for the inhibition of the CSF-1/CSF-1R interaction

| CSF-1R Mab | IC50 CSF-1/CSF-1R Inhibition [ng/ml] |
|---|---|
| Mab 2F11 | 19.3 |
| Mab 2E10 | 20.6 |
| Mab 2H7 | 18.2 |
| Mab 1G10 | 11.8 |
| SC-2-4A5 | 35.2 |

Example 3

Inhibition of CSF-1-Induced CSF-1R Phosphorylation in NIH3T3-CSF-1R Recombinant Cells $4.5 \times 10^3$ NIH 3T3 cells, retrovirally infected with an expression vector for full-length CSF-1R, were cultured in DMEM (PAA Cat. No. E15-011), 2 mM L-glutamine (Sigma, Cat. No. G7513, 2 mM Sodium pyruvate, 1× nonessential aminoacids, 10% FKS (PAA, Cat. No. A15-649) and 100 μg/ml PenStrep (Sigma, Cat. No. P4333 [10 mg/ml]) until they reached confluency. Thereafter cells were washed with serum-free DMEM media (PAA Cat. No. E15-011) supplemented with sodium selenite [5 ng/ml] (Sigma, Cat. No. S9133), transferrin [10 μg/ml] (Sigma, Cat. No. T8158), BSA [400 μg/ml] (Roche Diagnostics GmbH, Cat. No. 10735078), 4 mM L-glutamine (Sigma, Cat. No. G7513), 2 mM sodium pyruvate (Gibco, Cat. No. 11360), 1× nonessential aminoacids (Gibco, Cat: 11140-035), 2-mercaptoethanol [0.05 mM] (Merck, Cat. No. M7522), 100 μg/ml and PenStrep (Sigma, Cat. No. P4333) and incubated in 30 μl of the same medium for 16 hours to allow for receptor up-regulation. 10 μl of diluted anti-CSR-1R antibodies were added to the cells for 1.5 h. Then cells were stimulated with 10 μl of 100 ng/ml hu CSF-1 (active 149 aa fragment of human CSF-1 (aa 33-181 of SEQ ID NO: 86); Biomol, DE, Cat. No. 60530) for 5 min. After the incubation, supernatant was removed, cells were washed twice with 80 μl of ice-cold PBS and 50 μl of freshly prepared ice-cold lysis buffer (150 mM NaCl/20 mM Tris pH 7.5/1 mM EDTA/1 mM EGTA/1% Triton X-100/1 protease inhibitor tablet (Roche Diagnostics GmbH Cat. No. 1 836 170) per 10 ml buffer/10 μl/ml phosphatase inhibitor cocktail 1 (Sigma Cat. No. P-2850, 100× Stock)/10 μl/ml protease inhibitor 1 (Sigma Cat. No. P-5726, 100× Stock)/10 μl/ml 1 M NaF) was added. After 30 minutes on ice the plates were shaken vigorously on a plateshaker for 3 minutes and then centrifuged 10 minutes at 2200 rpm (Heraeus Megafuge 10).

The presence of phosphorylated and total CSF-1 receptor in the cell lysate was analyzed with Elisa. For detection of the phosphorylated receptor the kit from R&D Systems (Cat. No. DYC3268-2) was used according to the instructions of the supplier. For detection of total CSF-1R 10 μl of the lysate was immobilized on plate by use of the capture antibody contained in the kit. Thereafter 1:750 diluted biotinylated anti CSF-1R antibody BAF329 (R&D Systems) and 1:1000 diluted streptavidin-HRP conjugate was added. After 60 minutes plates were developed with freshly prepared ABTS® solution and the absorbance was detected. Data were calculated as % of positive control without antibody and the ratio value phospho/total receptor expressed. The negative control was defined without addition of M-CSF-1. Anti CSF-1R SC 2-4A5 (Santa Cruz Biotechnology, US, see also Sherr, C. J. et al., Blood 73 (1989) 1786-1793), which inhibits the ligand-receptor interaction, was used as reference control.

TABLE 2

Calculated IC50 values for the inhibition of CSF-1 receptor phosphorylation.

| CSF-1R Mab | IC50 CSF-1R Phosphorylation [ng/ml] |
|---|---|
| Mab 2F11 | 219.4 |
| Mab 2E10 | 752.0 |
| Mab 2H7 | 703.4 |

TABLE 2-continued

Calculated IC50 values for the inhibition of
CSF-1 receptor phosphorylation.

| CSF-1R Mab | IC50 CSF-1R Phosphorylation [ng/ml] |
|---|---|
| Mab 1G10 | 56.6 |
| SC-2-4A5 | 1006.6 |

Example 4

Determination of the Binding of Anti-CSF-1R
Antibodies to Human CSF-1R Fragment delD4 and
to Human CSF-1R Extracellular Domain

CSF-1R-ECD

Preparation of Human CSF-1R Extracellular Domain (CSF-1R-ECD) (Comprising the Extracellular Subdomains D1-D5, hCSF-1R-ECD) of SEQ ID NO: 64:

pCMV-preS-Fc-hCSF-1R-ECD (7836 bp) encodes the complete ECD of human CSF-1R (SEQ ID NO: 64) C-terminally fused to a PreScission protease cleavage site, followed by aa100-330 of human IgG1 and a 6×His-Tag, under the control of CMV promoter. The natural signal peptide has been varied by insertion of amino acids G and S after the first M, in order to create a BamHI restriction site.

Preparation of Human CSF-1R Fragment delD4 (Comprising the Extracellular Subdomains D1-D3 and D5, hCSF-1R-delD4) of SEQ ID NO: 65:

hCSF1R-delD4-V1-PreSc-hFc-His was cloned from pCMV-preS-Fc-hCSF-1R-ECD by means of the Stratagene QuikChange XL site-directed mutagenesis protocol, using delD4-for with sequence CACCTCCATGTTCTTCCGG-TACCCCCCAGAGGTAAG (SEQ ID NO: 68) as the forward primer and delD4-rev with the reverse complement sequence as the reverse primer. A protocol variation published in Bio-Techniques 26 (1999) 680 was used to extend both primers in separate reactions in three cycles preceeding the regular Stratagene protocol:

Two separate 50 µl reaction mixtures were set up according to the manufacturer's manual, each containing 10 ng plasmid pCMV-preS-Fc-hCSF1R-ECD as the template and 10 pM of one of the primers delD4-for or delD4-rev, and 0.5 µl Pfu DNA polymerase as provided with the kit. Three PCR cycles 95° C. 30 sec/55° C. 60 sec/68° C. 8 min were run, then 25 µl each of both reaction mixtures were combined in a new tube and 0.5 µl fresh Pfu DNA polymerase were added. The regular PCR protocol with 18 temperature cycles as specified by Stratagene in the kit manual was carried out, followed by 2 hrs final digestion with the Dpn1 restriction enzyme provided with the kit. Clones bearing the deletion were detected by digestion with Cel II and Not I and verified by sequencing.

Protein was prepared by transient transfection in the Hek293 FreeStyle suspension cell system (Invitrogen) according to the manufacturer's specifications. After 1 week 500 ml supernatant was filtered and loaded onto a 1 ml HiTrap MabSelect Xtra (GE healthcare) protein A column (0.2 ml/min). The column was washed first with PBS, then with 50 mM Tris/150 mM NaCl/1 mM EDTA/pH 7.3. 75 µl PreScission Protease (GE #27-0843-01) diluted in 375 µl of the same buffer were loaded onto the column and the closed column was incubated over night at 4° C. with rolling. The column was mounted on top of a 1 ml GSTrap FF column (GE helthcare) and the desired protein was eluted (0.2 ml/min, 0.2 ml fractions). Pooled fractions were concentrated from 1.8 ml to 0.4 ml by centrifugal ultrafiltration via a 3k Nanosep and chromatographed over an S200 HR SEC in PBS (0.5 ml/min).

Human CSF-1R fragment delD4 was obtained in two fractions as a dimeric molecule (pool 1, V=1.5 ml; c=0.30 mg/ml; apparent mass on SDS page 83 kDa, reduced 62 kDa) and as the monomer (pool 2, V=1.4 ml; c=0.25 mg/ml apparent mass on SDS page 62 kDa). The dimeric form was used for all experiments.

Determination of the Binding of Anti-CSF-1R Antibodies to Human CSF-1R Fragment delD4 and to Human CSF-1R Extracellular Domain (CSF-1R-ECD) (Binding Signals as Response Units (RU):

Instrument: Biacore T100 (GE Healthcare)
Software:
T100 Control, Version 2.0.1
T100 Evaluation, Version 2.0.2
Assay format Chip: CM5
Temperature: 25° C.

CSF-1R fragments were immobilized via amine coupling. To compare the binding of different anti-CSF-1R antibodies according to the invention one concentration of the test antibody was injected. Anti CSF-1R Mab3291 (R&D-Systems) and SC 2-4A5 (Santa Cruz Biotechnology, US—see also Sherr, C. J. et al., Blood 73 (1989) 1786-1793), was used as reference control, anti-CCR5 m<CCR5>Pz03.1C5 (deposited as DSM ACC 2683 on 18 Aug. 2004 at DSMZ) as negative control, all under the same conditions as the anti-CSF-1R antibodies according to the invention.

Amine Coupling of CSF-1R Fragments

Standard amine coupling according to the manufacturer's instructions: running buffer: PBS-T (Roche: 11 666 789+ 0.05% Tween20: 11 332 465), activation by mixture of EDC/NHS, injection of human CSF-1R fragment delD4 (comprising the extracellular subdomains D1-D3 and D5) (SEQ ID NO: 65) and human CSF-1R Extracellular Domain (CSF-1R-ECD) (comprising the extracellular subdomains D1-D5) (SEQ ID NO: 64) for 600 seconds at flow rate 10 µl/min; diluted in coupling buffer NaAc, pH 5.0, c=10 µg/mL; finally remaining activated carboxyl groups were blocked by injection of 1 M Ethanolamin.

Binding of <CSF-1R> Mab 2F11, Mab 2E10, Mab 3291 and Sc2-4A5 and Other Anti-CSF-1R Antibodies to Human CSF-1R Fragment delD4 and Human CSF-1R Extracellular Domain (CSF-1R-ECD) at 25° C.

Running buffer: PBS-T (Roche: 11 666 789+0.05% Tween20: 11 332 465)

Analyte Sample:

Binding was measured at a flow rate of 30 µL/min by one injection of the analyte with concentration c=10 nM. (for Mab 1G10, Mab 2H7 and humanized hMab 2F11-e7 in second experiment) Each injection was 700 seconds long, followed by a dissociation phase of 180 seconds. Final regeneration was performed after each cycle using 50 mM NaOH, contact time 60 seconds, flow rate 30 µL/min.

Signals were measured by a report point 10 seconds after end of injection. Reference signals (signals from a blank reference flow cell (treated with EDC/NHS and ethanolamine, only) were subtracted to give the binding signals (as RU). If binding signals of nonbinding antibodies were slightly below 0 (Mab 2F11=−3; Mab 2E10=−2; Mab 1G10=−6, Mab 2H7=−9; and humanized hMab 2F11-e7=−7) the values were set as 0.

TABLE 3a

Binding of <CSF-1R> MAbs to human CSF-1R fragment
delD4 and CSF-1R-ECD and ratio at 25° C., measured by SPR

| | Binding to delD4 [RU] | Binding to CSF-1R-ECD [RU] | Ratio of binding of anti-CSF1R antibodies to CSF1R fragment delD4/ to CSF-1R-ECD |
|---|---|---|---|
| Mab 3291 | 1015 | 627 | 1015/627 = 1.61 |
| sc2-4A5 | 374 | 249 | 374/249 = 1.50 |
| Mab 2F11 | 0 | 176 | 0/176 = 0 |
| hMab 2F11-e7 | 0 | 237 | 0/237 = 0 |
| Mab 2E10 | 0 | 120 | 0/120 = 0 |
| Mab 1G10 | 0 | 2708 | 0/2708 = 0 |
| Mab 2H7 | 0 | 147 | 0/147 = 0 |
| m<CCR5>Pz03.1C5 | 2 | 5 | — |

Mab 2F11 and Mab 2E10 showed binding to the human CSF-1R Extracellular Domain (CSF-1R-ECD) (see FIG. 3b); however no binding was detected to CSF-1R fragment delD4. (see FIG. 3a).

Figure 3A:
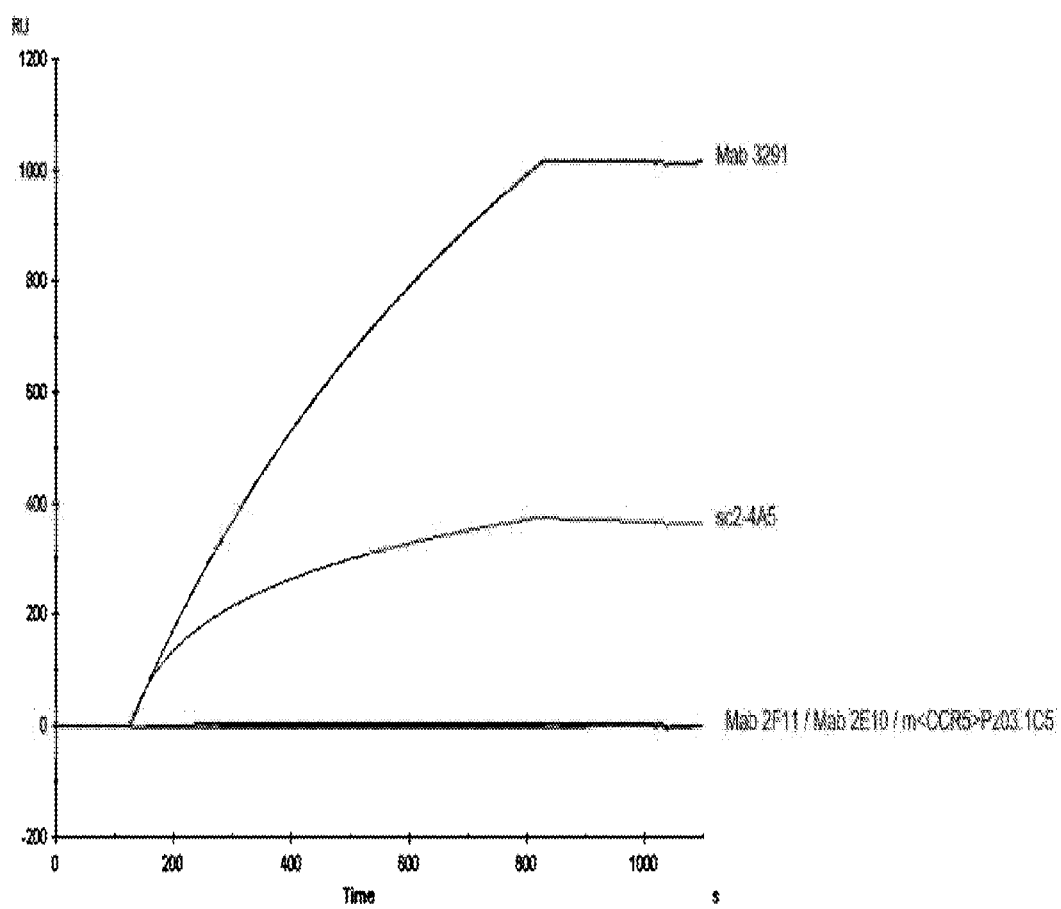
FIGS. 3A-3F illustrate data demonstrating binding of different anti-CSF-1R antibodies to immobilized human CSF-1R.
Figure 3B:
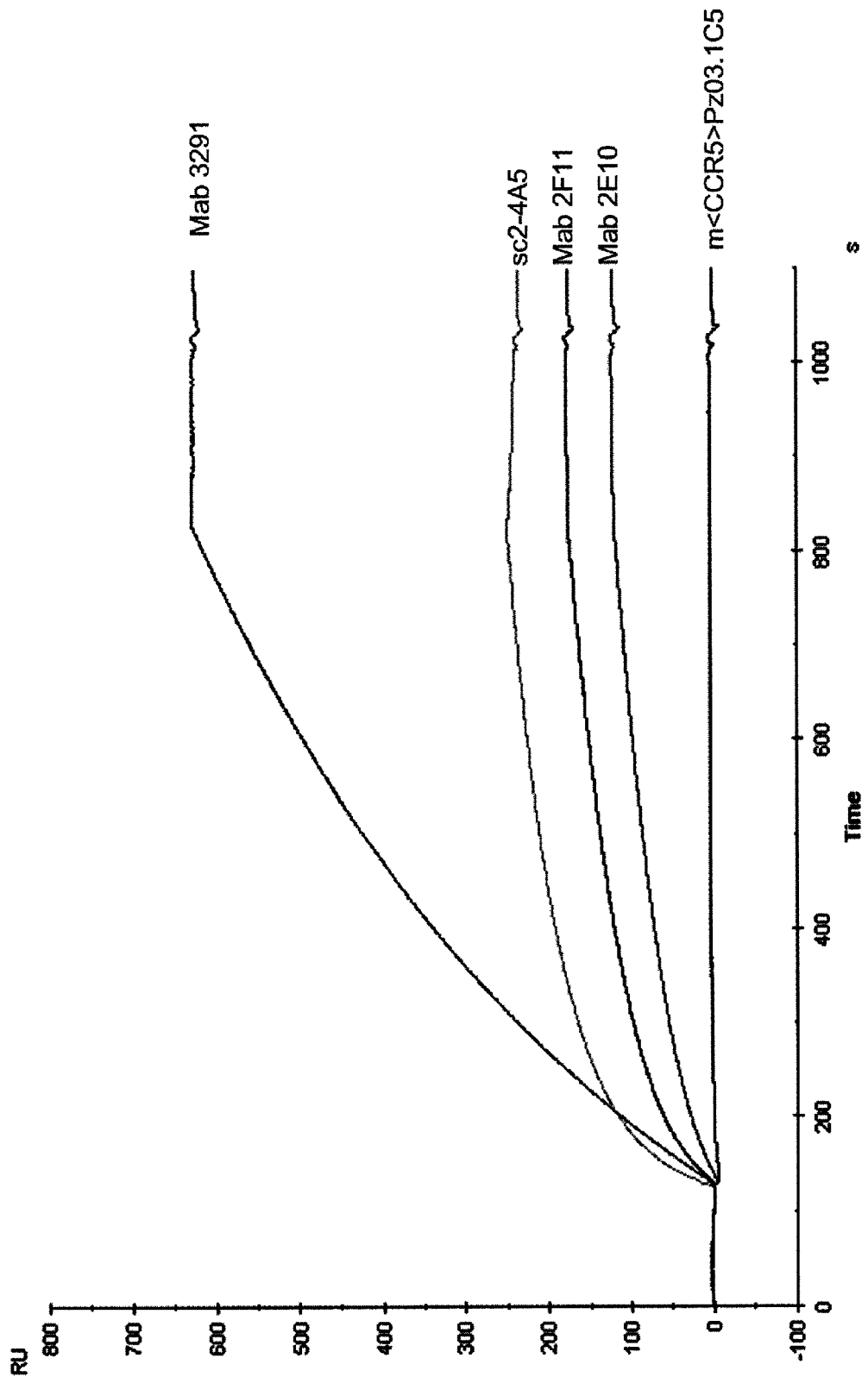
Figure 3C:
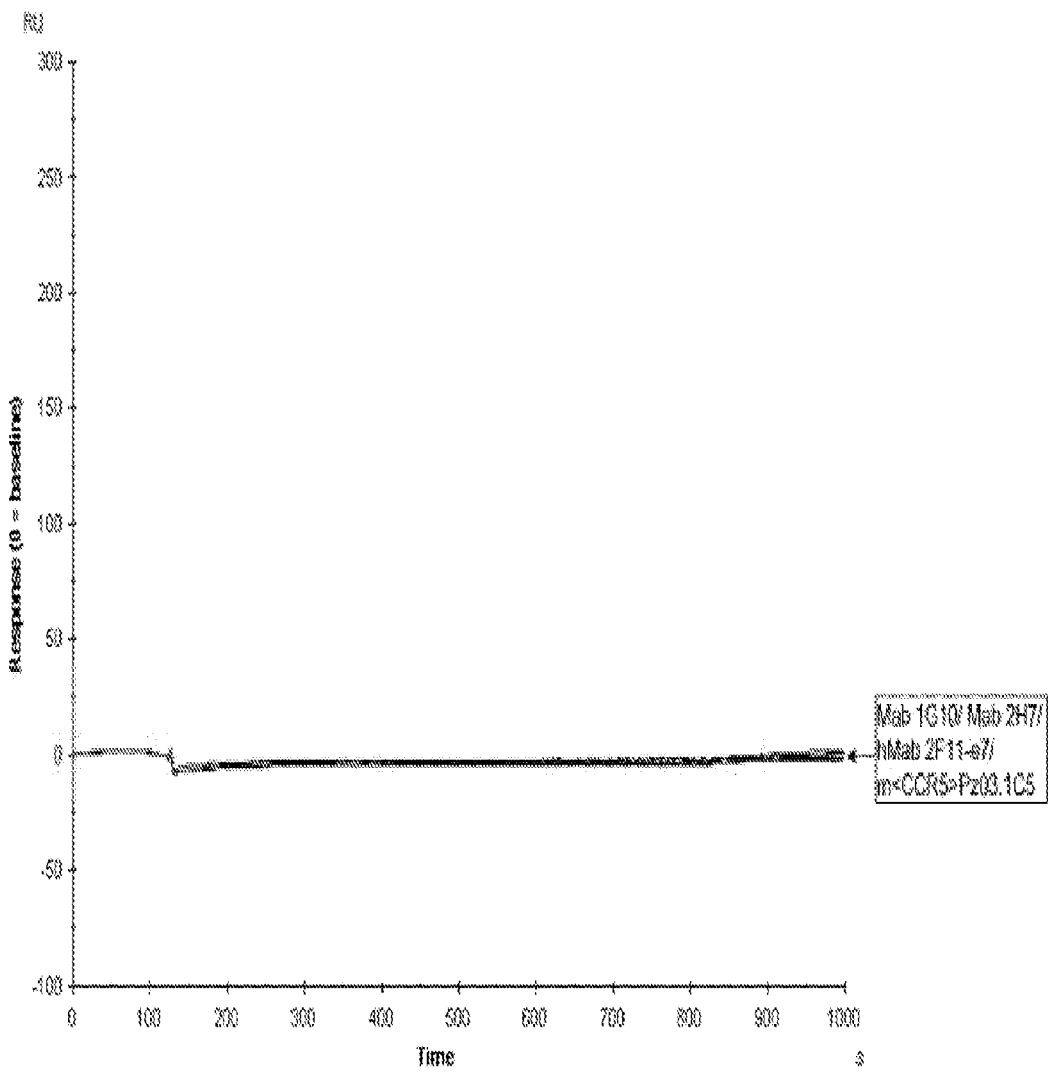

Sc2-4A5 and MAB3291 showed binding to CSF-1R-ECD and to del D4 (see FIGS. 3b and 3a).

Thus the ratio of binding of anti-CSF1R antibodies Mab 2F11 and Mab 2E10 to CSF1R fragment delD4/to CSF-1R-ECD was clearly below 1:50 (=0.02), while the binding ratio of MAB3291 and Sc2-4A5 were 1.61 and 1.50, respectively and were highly above 1:50 (=0.02). Negative control antibody m<CCR5>Pz03.1C5 did not show any binding (as expected).

Figure 3D:
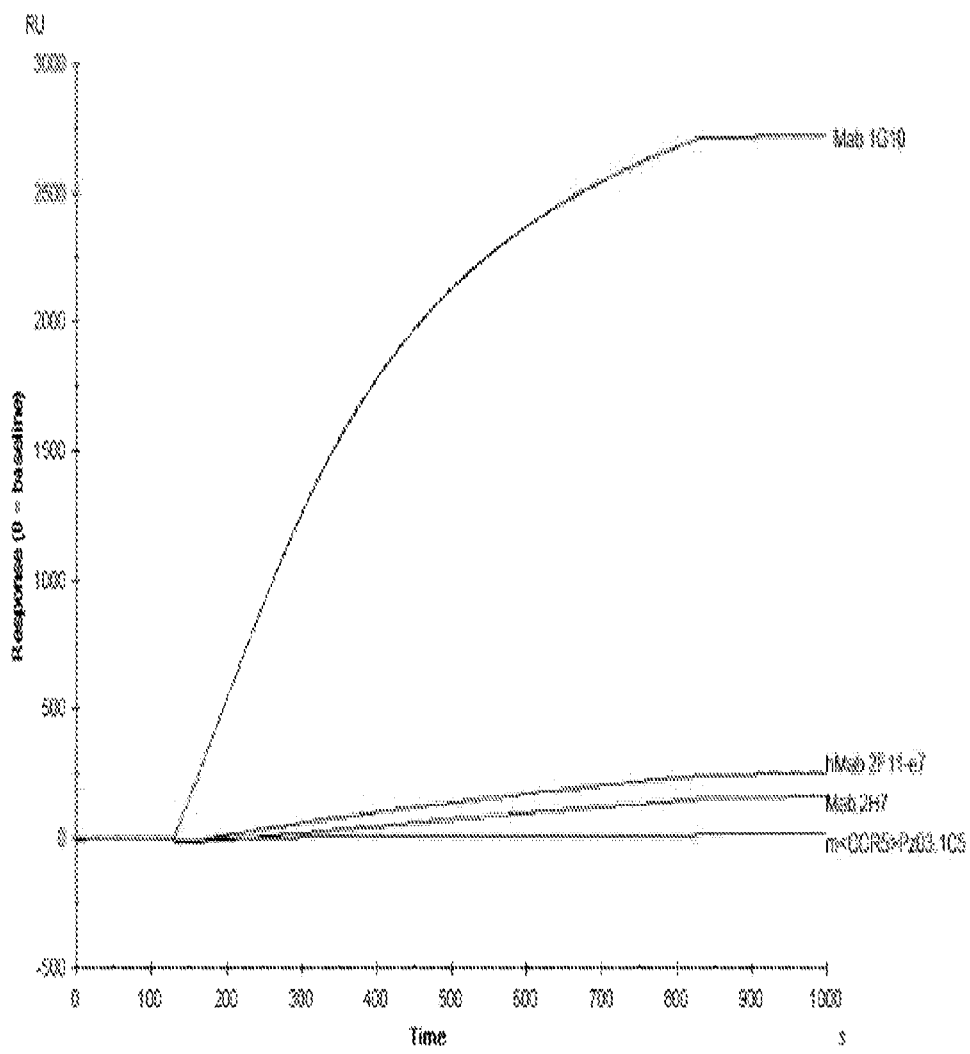

Mab 1G10, Mab 2H7 and humanized hMab 2F11-e7 showed binding to the human CSF-1R Extracellular Domain (CSF-1R-ECD) (see FIG. 3d); however no binding was detected to CSF-1R fragment delD4. (see FIG. 3). Thus the ratio of binding of anti-CSF1R antibodies Mab 1G10, Mab 2H7 and humanized hMab 2F11-e7 to CSF1R fragment delD4/to CSF-1R-ECD was clearly below 1:50 (=0.02).

In a further experiment anti-CSF-1R antibodies 1.2.5M (ligand displacing CSF-1R antibody described in WO2009026303), CXIIG6 (ligand displacing CSF-1R antibody described in WO 2009/112245), the goat polyclonal anti-CSF-1R antibody ab10676 (abcam) were investigated. Anti-CSF-1R antibody Mab3291 (R&D-Systems) was used as reference control. Anti-CCR5 m<CCR5>Pz03.1C5 (deposited as DSM ACC 2683 on 18 Aug. 2004 at DSMZ) was used as negative control.

TABLE 3b

Binding of <CSF-1R> MAbs to human CSF-1R fragment
delD4 and CSF-1R-ECD and ratio at 25° C., measured by SPR

| | Binding to delD4 [RU] | Binding to CSF-1R-ECD [RU] | Ratio of binding of anti-CSF1R antibodies to CSF1R fragment delD4/ to CSF-1R-ECD |
|---|---|---|---|
| MAB3291 | 1790 | 1222 | 1790/1222 = 1.47 |
| 1.2.SM | 469 | 704 | 469/704 = 0.67 |
| CXIIG6 | 1983 | 1356 | 1983/1356 = 1.46 |
| ab10676 | 787 | 547 | 787/547 = 1.44 |
| m<CCR5>Pz03.1C5 | 0 | 0 | — |

Figure 3E:
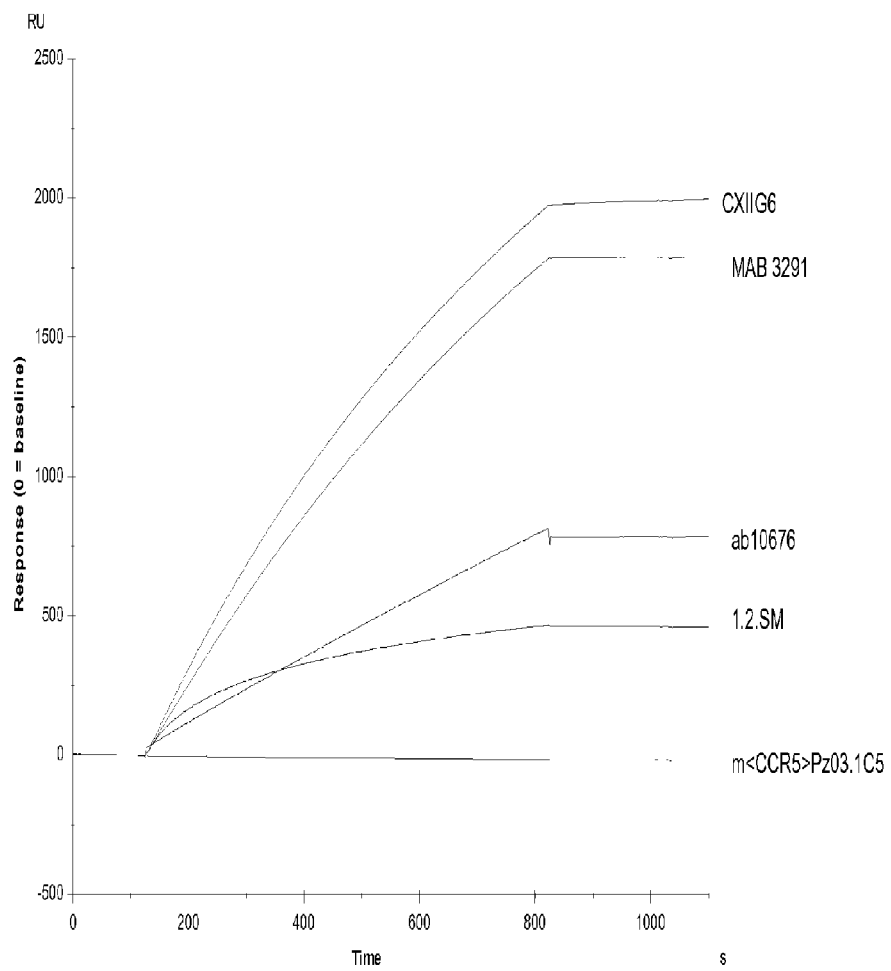
Figure 3F:
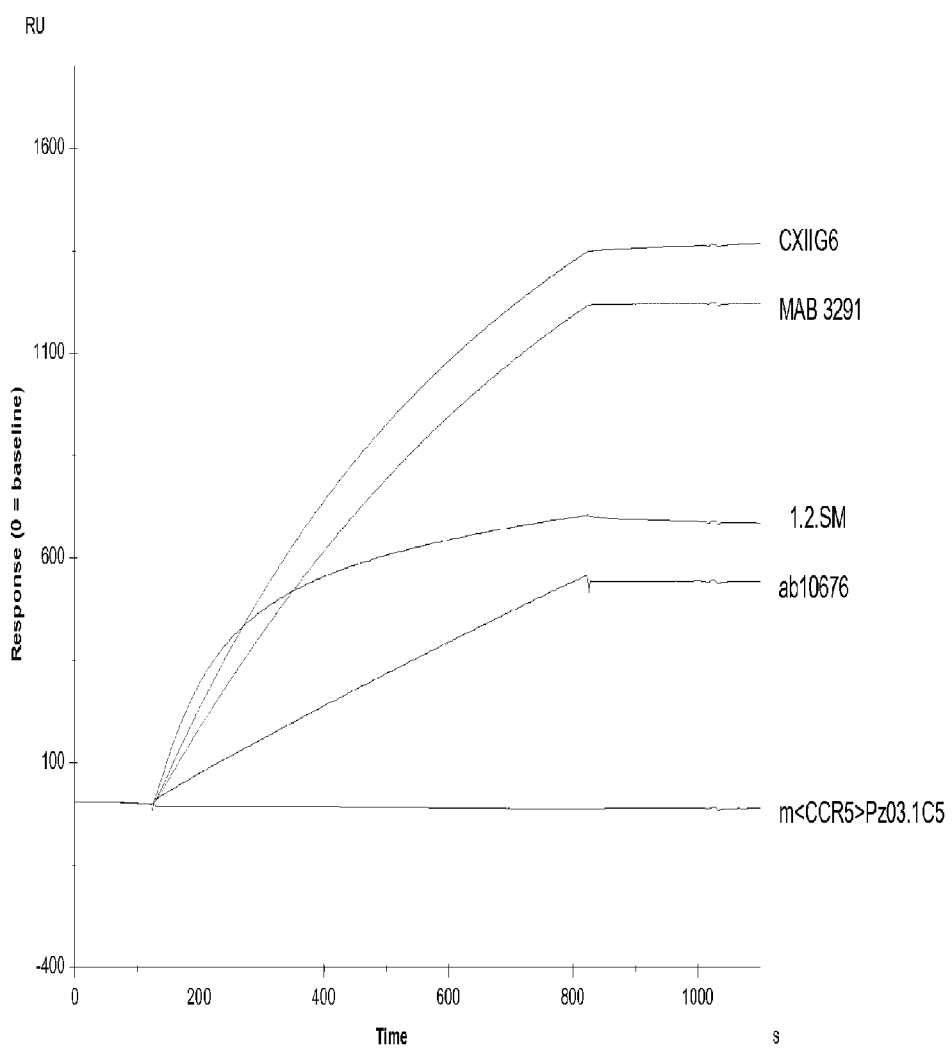
Figure 4A:
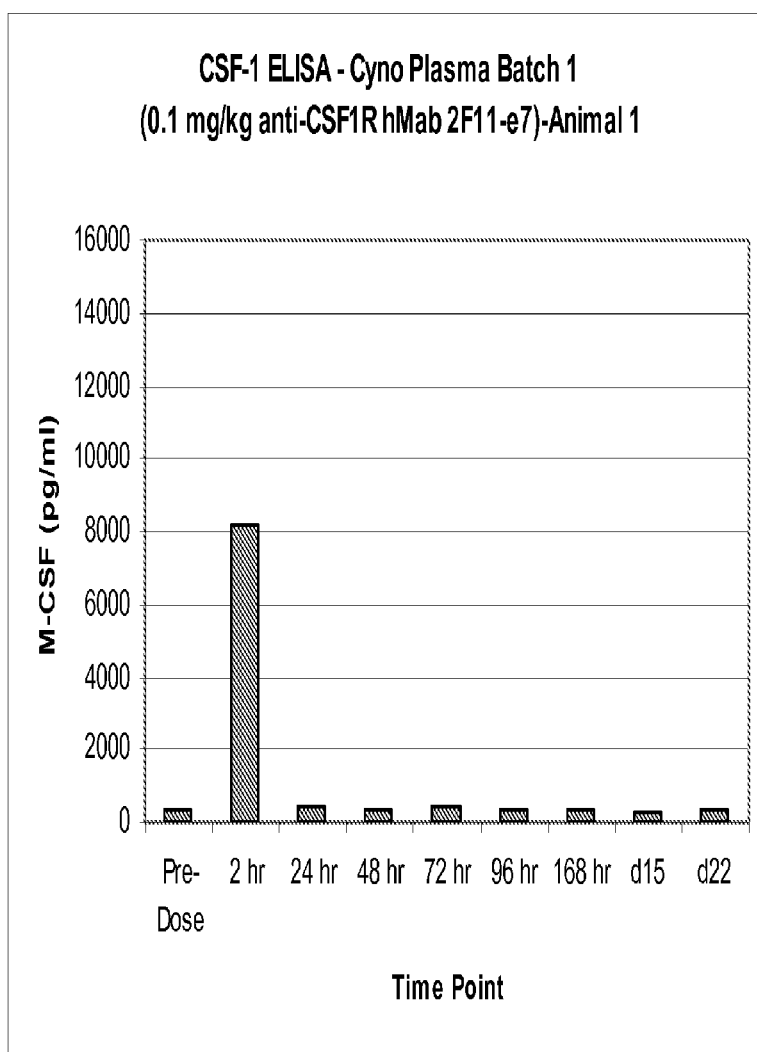
FIGS. 4A-4D illustrate data showing CSF-1 levels in Cynomolgous monkey after administration of different dosages of anti-CSF-1R antibody.
Figure 4B:
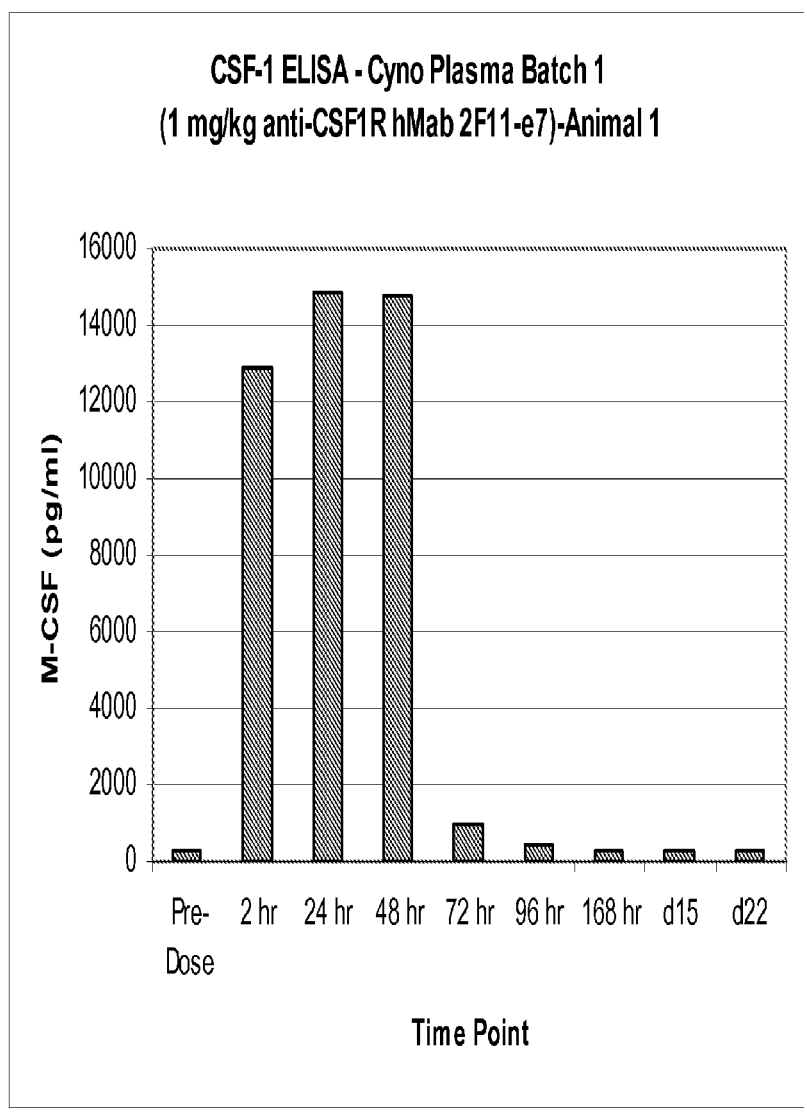
Figure 4C:
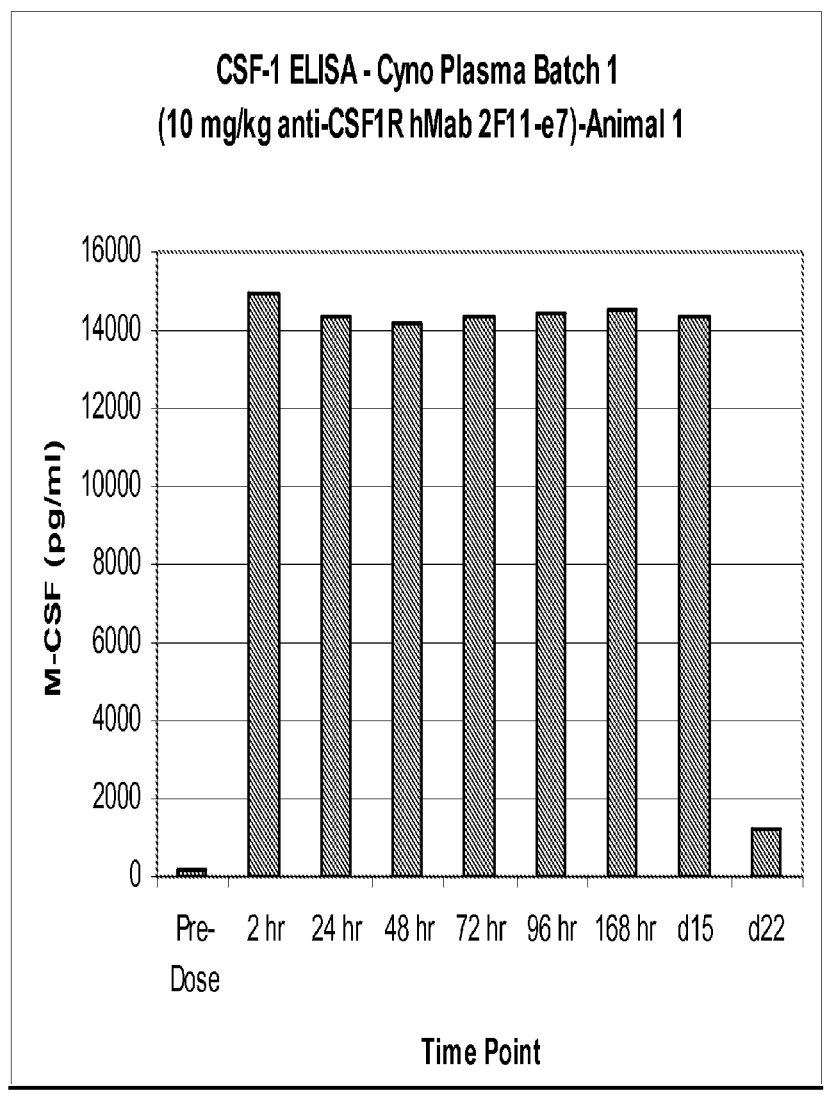
Figure 4D:
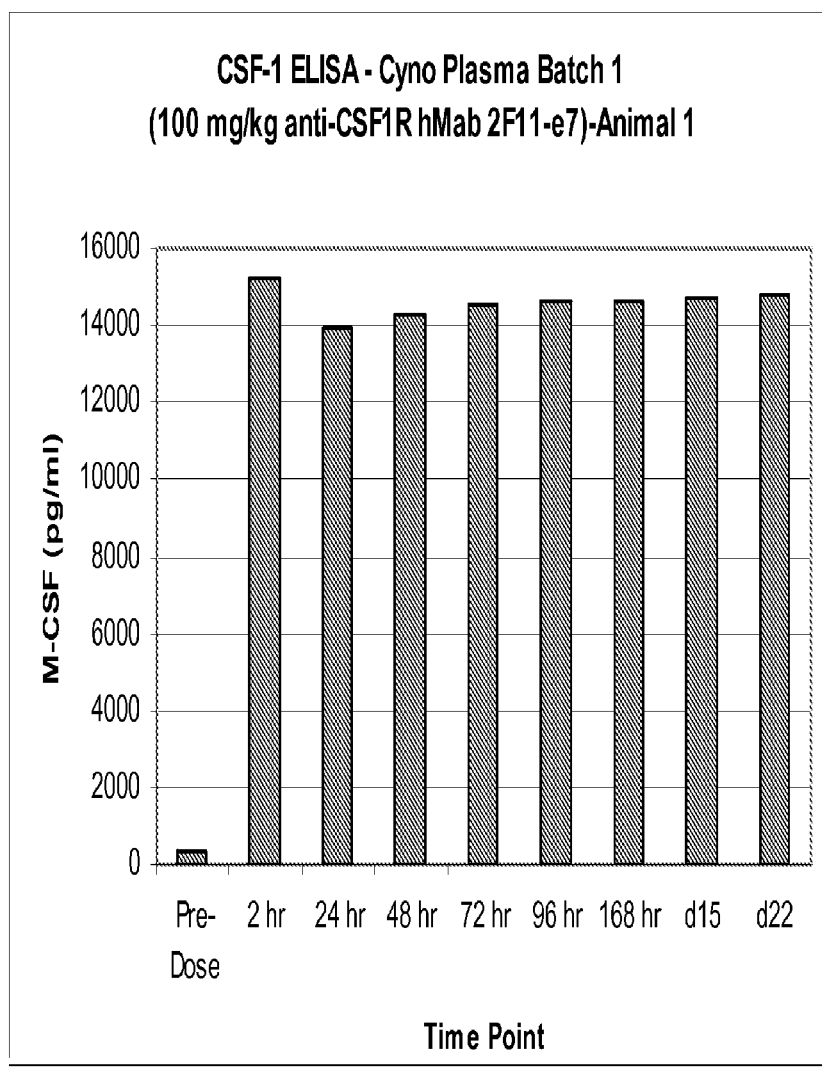

1.2.5M, CXIIG6, ab10676 and MAB3291 showed binding to CSF-1R-ECD and to del D4 (see FIGS. 3f and 3e).

The binding ratio of 1.2.5M, CXIIG6, ab10676 and MAB3291 was highly above 1:50 (=0.02). Negative control antibody m<CCR5>Pz03.1C5 did not show any binding (as expected).

Example 5

Growth Inhibition of NIH3T3-CSF-1R Recombinant Cells in 3D Culture Under Treatment with Anti-CSF-1R Monoclonal Antibodies (CellTiterGlo®-Assay)

NIH 3T3 cells, retrovirally infected with either an expression vector for full-length wildtype CSF-1R (SEQ ID NO: 62) or mutant CSF-1R L301S Y969F (SEQ ID NO: 63), were cultured in DMEM high glucose media (PAA, Pasching, Austria) supplemented with 2 mM L-glutamine, 2 mM sodium pyruvate and non-essential amino acids and 10% fetal bovine serum (Sigma, Taufkirchen, Germany) on poly-HEMA (poly (2hydroxyethylmethacrylate)) (Polysciences, Warrington, Pa., USA)) coated dishes to prevent adherence to the plastic surface. Cells are seeded in medium replacing serum with 5 ng/ml sodium selenite, 10 mg/ml transferrin, 400 µg/ml BSA and 0.05 mM 2-mercaptoethanol.

When treated with 100 ng/ml hu CSF-1 (active 149 aa fragment of human CSF-1 (aa 33-181 of SEQ ID NO: 86); Biomol, DE, Cat. No. 60530) wtCSF-1R (expressing cells form dense spheroids that grow three dimensionally, a property that is called anchorage independence. These spheroids resemble closely the three dimensional architecture and organization of solid tumors in situ. Mutant CSF-1R recombinant cells are able to form spheroids independent of the CSF-1 ligand. Spheroid cultures were incubated for 3 days in the presence of different concentrations of antibody in order to determine an IC50 (concentration with 50 percent inhibition of cell viability). The CellTiterGlo® Assay was used to detect cell viability by measuring the ATP-content of the cells.

TABLE 4

| CSF-1R Mab | wtCSF-1R IC50 [µg/ml] | Mutant CSF-1R IC50 [µg/ml] |
|---|---|---|
| Mab 2F11 | 1.1 | 8.0 |
| Mab 2E10 | 0.49 | 4.9 |
| Mab 2H7 | 0.31 | 5.3 |
| Mab 1G10 | 0.29 | 14.2 |
| SC 2-4A5 | 10.0 | 10.0 |

Reference control Mab R&D-Systems 3291 did not show inhibition of mutant CSF-1R recombinant cell proliferation.

In a further experiment the anti-CSF-1R antibody according to the invention hMab 2F11-e7 and the anti-CSF-1R antibodies 1.2.5M (ligand displacing CSF-1R antibody described in WO 2009/026303), CXIIG6 (ligand displacing CSF-1R antibody described in WO 2009/112245), the goat polyclonal anti-CSF-1R antibody ab10676 (abcam), and SC 2-4A5 (Santa Cruz Biotechnology, US—see also Sherr, C. J. et al., Blood 73 (1989) 1786-1793) were investigated.

Spheroid cultures were incubated for 3 days in the presence of different concentrations of antibody in order to determine an IC30 (concentration with 30 percent inhibition of cell viability). Maximum concentration was 20 µg/ml. The CellTiterGlo® Assay was used to detect cell viability by measuring the ATP-content of the cells.

TABLE 5

| CSF-1R Mab | wtCSF-1R IC30 [µg/ml] | Mutant CSF-1R IC30 [µg/ml] |
|---|---|---|
| hMab 2F11-e7 | 4.91 | 0.54 |
| 1.2.SM | 1.19 | >20 µg/ml (−19%) |

TABLE 5-continued

| CSF-1R Mab | wtCSF-1R IC30 [μg/ml] | Mutant CSF-1R IC30 [μg/ml] |
|---|---|---|
| CXIIG6 | >20 μg/ml (21% inhibition at 20 μg/ml) | inhibition at 20 μg/ml = 19% stimulation)<br>>20 μg/ml (−36% inhibition at 20 μg/ml = 36% stimulation) |
| ab10676 | 14.15 | >20 μg/ml (0% inhibition at 20 μg/ml) |
| SC 2-4A5 | 16.62 | 2.56 |

Example 6

Growth Inhibition of BeWo Tumor Cells in 3D Culture Under Treatment with Anti-CSF-1R Monoclonal Antibodies (CellTiterGlo®-Assay)

Figure 2A:
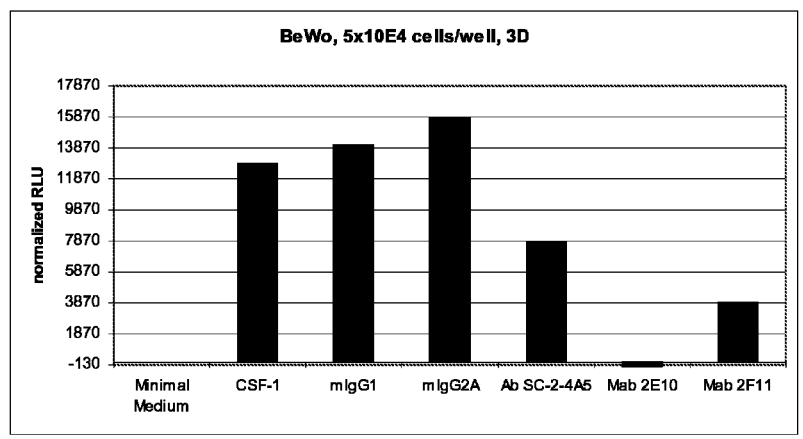
FIGS. 2A-2B illustrate data demonstrating growth inhibition of BeWo tumor cells in 3D culture under treatment with different anti-CSF-1R monoclonal antibodies at a concentration of 10 μg/ml.
X axis: viability normalized mean relative light units (RLU) corresponding to the ATP-content of the cells (CellTiterGlo® Assay).
Y axis: tested probes: Minimal Medium (0.5% FBS), mouse IgG1 (mIgG1, 10 μg/ml), mouse IgG2a (mIgG2a 10 μg/ml), CSF-1 only, Mab 2F11, Mab 2E10, Mab2H7, Mab1G10 and SC 2-4A5.
Highest inhibition of CSF-1 induced growth was observed with the anti-CSF-1R antibodies according to the invention.
Figure 2B:
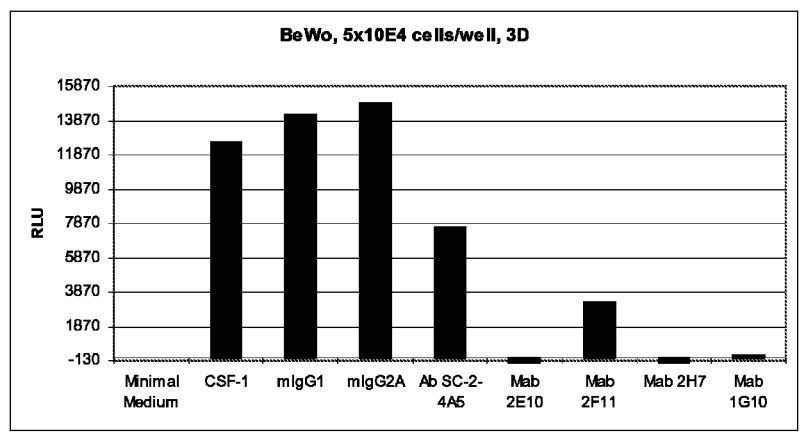

BeWo choriocarcinoma cells (ATCC CCL-98) were cultured in F12K media (Sigma, Steinheim, Germany) supplemented with 10% FBS (Sigma) and 2 mM L-glutamine. $5 \times 10^4$ cells/well were seeded in 96-well poly-HEMA (poly (2-hydroxyethylmethacrylate)) coated plates containing F12K medium supplemented with 0.5% FBS and 5% BSA. Concomitantly, 200 ng/ml huCSF-1 (active 149 aa fragment of human CSF-1 (aa 33-181 of SEQ ID NO: 86)) and 10 μg/ml of different anti-CSF-1R monoclonal antibodies were added and incubated for 6 days. The CellTiterGlo® Assay was used to detect cell viability by measuring the ATP-content of the cells in relative light units (RLU). When BeWo spheroid cultures were treated with different anti-CSF-1R antibodies (10 μg/ml) inhibition of CSF-1 induced growth was observed. To calculate antibody-mediated inhibition the mean RLU value of unstimulated BeWo cells was subtracted from all samples. Mean RLU value of CSF-1 stimulated cells was set arbitrarily to 100%. Mean RLU values of cells stimulated with CSF-1 and treated with anti-CSF-1R antibodies were calculated in % of CSF-1 stimulated RLUs. The Table 6 shows the calculated data of growth inhibition of BeWo tumor cells in 3D culture under treatment with anti-CSF-1R monoclonal antibodies; FIGS. 2a and b depicts normalized mean RLU values.

TABLE 6

| CSF-1R Mab | % inhibition 10 μg/ml antibody concentration |
|---|---|
| CSF-1 only | 0 |
| Mab 2F11 | 70 |
| Mab 2E10 | 102 |
| Mab 2H7 | 103 |
| Mab 1G10 | 99 |
| SC 2-4A5 | 39 |

Example 7

Growth Inhibition of Human Macrophage Differentiation Under Treatment with Anti-CSF-1R Monoclonal Antibodies (CellTiterGlo®-Assay)

Human monocytes were isolated from peripheral blood using the RosetteSep™ Human Monocyte Enrichment Cocktail (StemCell Tech. —Cat. No. 15028). Enriched monocyte populations were seeded into 96 well microtiterplates ($2.5 \times 10^4$ cells/well) in 100 μl RPMI 1640 (Gibco—Cat. No. 31870) supplemented with 10% FCS (GIBCO—Cat. No. 011-090014M), 4 mM L-glutamine (GIBCO—Cat. No. 25030) and 1× PenStrep (Roche Cat. No. 1 074 440) at 37° C. and 5% $CO_2$ in a humidified atmosphere. When 150 ng/ml huCSF-1 was added to the medium, a clear differentiation into adherent macrophages could be observed. This differentiation could be inhibited by addition of anti-CSF-1R antibodies. Furthermore, the monocyte survival is affected and could be analyzed by CellTiterGlo® (CTG) analysis. From the concentration dependent inhibition of the survival of monocytes by antibody treatment, an IC50 was calculated (see Table 7).

TABLE 7

| CSF-1R Mab | IC50 [μg/ml] |
|---|---|
| Mab 2F11 | 0.08 |
| Mab 2E10 | 0.06 |
| Mab 2H7 | 0.03 |
| Mab 1G10 | 0.06 |
| SC 2-4A5 | 0.36 |

In a separate test series humanized versions of Mab 2 F11, e.g. hMab 2F11-c11, hMab 2F11-d8, hMab 2F11-e7, hMab 2F11-f12, showed IC50 values of 0.07 μg/ml (hMab 2F11-c11), 0.07 μg/ml (hMab 2F11-d8), 0.04 μg/ml (hMab 2F11-e7) and 0.09 μg/ml (hMab 2F11-f12).

Example 8

Inhibition of Cynomolgous Macrophage Differentiation Under Treatment with Anti-CSF-1R Monoclonal Antibodies (CellTiterGlo®-Assay)

Cynomolgous monocytes were isolated from peripheral blood using the CD14 MicroBeads non-human primate kit (Miltenyi Biotec—Cat. No. 130-091-097) according to the manufacturers description. Enriched monocyte populations were seeded into 96 well microtiterplates ($1-3 \times 10^4$ cells/well) in 100 μl RPMI 1640 (Gibco—Cat. No. 31870) supplemented with 10% FCS (GIBCO—Cat. No. 011-090014M), 4 mM L-glutamine (GIBCO—Cat. No. 25030) and 1× PenStrep (Roche Cat. No. 1 074 440) at 37° C. and 5% $CO_2$ in a humidified atmosphere. When 150 ng/ml huCSF-1 was added to the medium, a clear differentiation into adherent macrophages could be observed. This differentiation could be inhibited by addition of anti-CSF-1R antibodies. Furthermore, the monocyte survival is affected and could be analyzed by CellTiterGlo® (CTG) analysis. The viability was analyzed at a concentration of 5 μg/ml antibody treatment (see Table 8).

TABLE 8

| CSF-1R Mab | % survival | % inhibition (of survival) = (100% − % survival) |
|---|---|---|
| Mab 2F11 | 4* | 96 |
| Mab 2E10 | 17** | 83 |
| Mab 2H7 | 8 | 92 |
| Mab 1G10 | 2 | 98 |
| SC 2-4A5 | 31 | 69 |

*mean of four experiments (3 expts. using the murine, 1 expt. using the chimeric mAb)
**mean of two experiments using the murine mAb only

Example 9

Inhibition of Human M1 and M2 Macrophage Differentiation Under Treatment with Anti-CSF-1R Monoclonal Antibodies (CellTiterGlo®-Assay)

Human monocytes were isolated from peripheral blood using the RosetteSep™ Human Monocyte Enrichment Cocktail (StemCell Tech.—Cat. No. 15028). Enriched monocyte populations were seeded into 96 well microtiterplates (2.5× $10^4$ cells/well) in 100 µl RPMI 1640 (Gibco—Cat. No. 31870) supplemented with 10% FCS (GIBCO—Cat. No. 011-090014M), 4 mM L-glutamine (GIBCO—Cat. No. 25030) and 1× PenStrep (Roche Cat. No. 1 074 440) at 37° C. and 5% $CO_2$ in a humidified atmosphere. When 100 ng/ml huCSF-1 was added for 6 days to the medium, a clear differentiation into adherent, M2 macrophages with elongated morphology could be observed. When 100 ng/ml huGM-CSF was added to the medium for 6 days, a clear differentiation into adherent, M1 macrophages with round morphology could be observed. This differentiation was associated with the expression of certain markers such as CD 163 for M2 macrophages and CD80 or high MHC class II for M1 macrophages as assessed by flow cytometry. Cells were washed with PBS and, if adherent, detached using a 5 mM EDTA solution in PBS (20 min at 37° C.). Cells were then well resuspended, washed with staining buffer (5% FCS in PBS) and centrifuged at 300×g for 5 min. Pellets were resuspended in 1 ml staining buffer and cells counted in a Neubauer chamber. Approximately 1×10e5 cells were transferred in each FACS tube, centrifuged at 300×g for 5 min and resuspended in staining buffer. Fcγ receptors were blocked by incubation with 1 µg human IgG/2.5×10e4 cells (JR Cat. No. 009-000-003) in staining buffer for 20 min on ice. Cells were then mixed with 1.5 µl antibody/2.5×10e4 cells for CD80 and CD163 detection whereas 5 µl antibody/2.5×10e4 cells for MHC class II detection was used: PE labeled mouse anti human CD163 (BD Bioscience Cat. No. 556018), PE labeled mouse anti human CD80 (BD Bioscience Cat. No. 557227) and Alexa 647 labeled mouse anti human MHC class II (Dako—Cat. No. M0775). The Alexa 647 label was conjugated to the antibody by using the Zenon Alexa 647 mouse IgG labeling kit (Invitrogen Cat. No. Z25008) After a 1-hour incubation on ice cells were washed twice with staining buffer, resuspended and measured at a FACS Canto II.

Figure 5A:
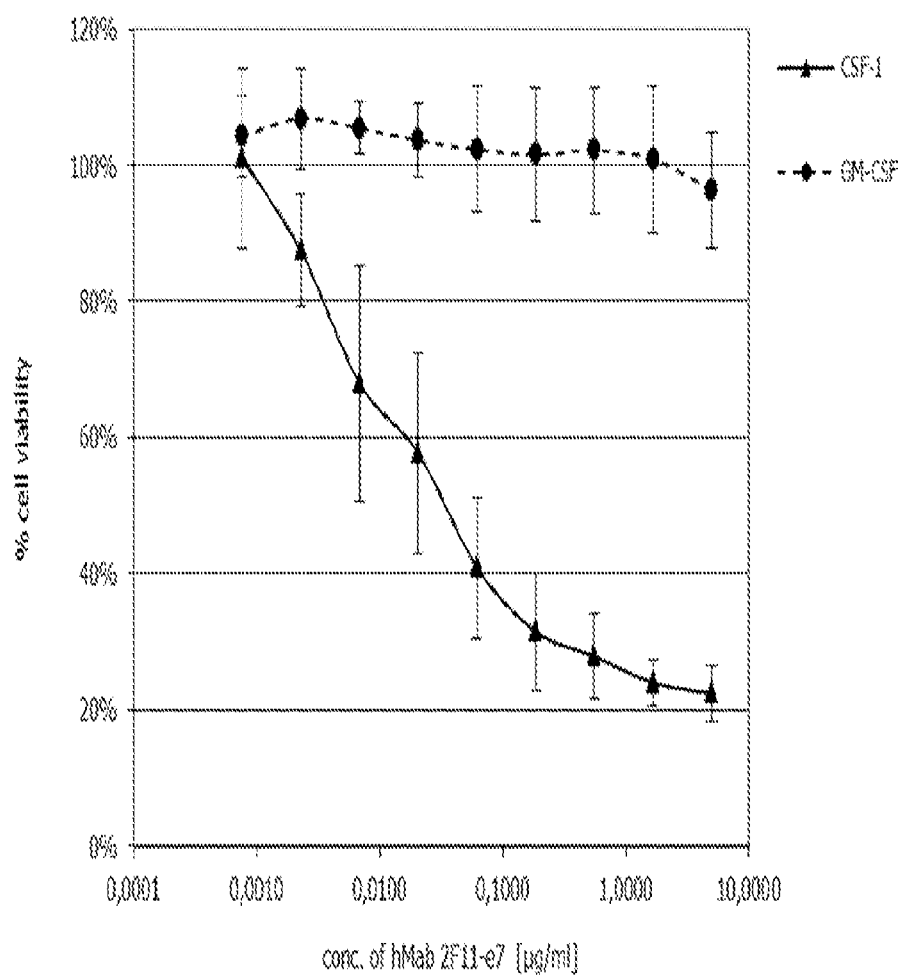
FIGS. 5A-5B illustrate data demonstrating human monocyte differentiation into macrophages.
Figure 5B:
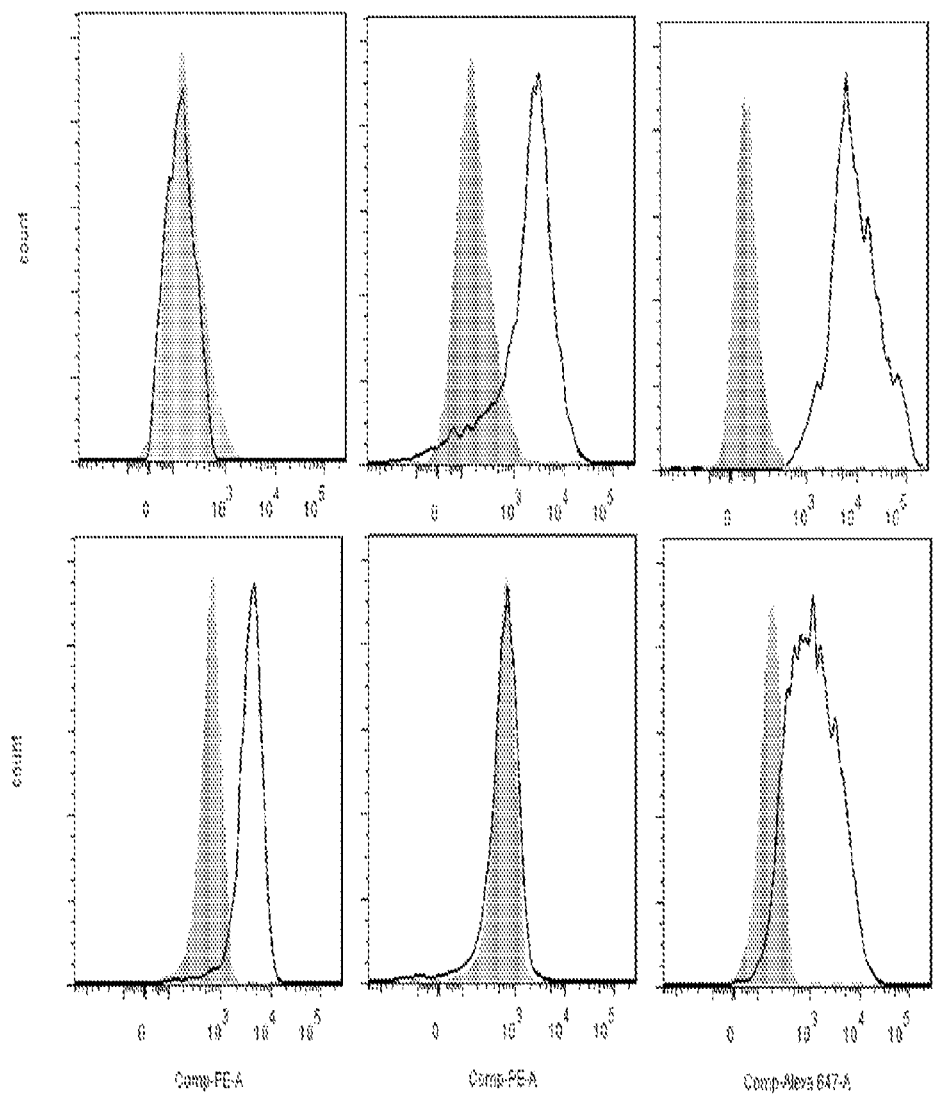

Exclusively M2 macrophage differentiation which is characterized by the expression of CD163, absence of CD80 and low MHC class II expression could be inhibited by addition of humanized anti-CSF-1R antibody hMab 2F11-e7. Furthermore, the M2 but not M1 macrophage survival is affected and could be analyzed by CellTiterGlo® (CTG) analysis. Concentration dependent inhibition of the survival of macrophages by antibody treatment for 7 days is depicted in FIG. 5a. Expression of M1 and M2 macrophage markers assessed by flow cytometry is shown in FIG. 5b.

Example 10

Determination of the Binding Affinity of Anti-CSF-1R Antibodies to Human CSF-1R Instrument: BIACORE® A100
Chip: CM5 (Biacore BR-1006-68)
Coupling: amine coupling
Buffer: PBS (Biacore BR-1006-72), pH 7.4, 35° C.

For affinity measurements 36 µg/ml anti mouse Fcγ antibodies (from goat, Jackson Immuno Research JIR115-005-071) have been coupled to the chip surface for capturing the antibodies against CSF-1R. Human CSF-1R Extracellular Domain (CSF-1R-ECD) (comprising the extracellular subdomains D1-D5) (SEQ ID NO: 64) (R&D-Systems 329-MR or subcloned pCMV-presS-HisAvitag-hCSF-1R-ECD) was added in various concentrations in solution. Association was measured by an CSF-1R-injection of 1.5 minutes at 35° C.; dissociation was measured by washing the chip surface with buffer for 10 minutes at 35° C. For calculation of kinetic parameters the Langmuir 1:1 model was used.

TABLE 9

Affinity data measured by SPR

| CSF-1R Mab | KD (nM) | ka (1/Ms) | kd (1/s) | $t^{1/2}$ (min) |
|---|---|---|---|---|
| Mab 2F11 | 0.29 | 1.77E+05 | 5.18E−05 | 223 |
| Mab 2E10 | 0.2 | 1.52E+05 | 2.97E−05 | 389 |
| Mab 2H7 | 0.21 | 1.47E+05 | 3.12E−05 | 370 |
| Mab 1G10 | 0.36 | 1.75E+05 | 6.28E−05 | 184 |

In a separate biacore binding assay using the CSF-1R ECD (data not shown) some competition of the antibodies Mab 2F11 and Mab 2E10 with the antibody Ab SC-2-4A5 was shown. However Mab 2F11/Mab 2E10 do not bind to the human CSF-1R fragment delD4, whereas Ab SC-2-4A5 binds to this delD4 fragment (see Example 4 and FIG. 3a). Thus the binding region of Mab 2F11/Mab 2E10 is clearly distinct from the binding region of Ab SC-2-4A5, but probably located in a vicinity area. In such competition assay both antibodies Mab 2F11 and Mab 2E10 did not compete with Mab3291 from R&D-Systems (data not shown).

Example 11

Determination of the Binding of Anti-CSF-1R Antibodies to Human CSF-1R Fragment D1-D3

Instrument: Biacore T100 (GE Healthcare)
Software:
T100 Control, Version 1.1.11
B3000 Evaluation, Version 4.01
Scrubber, Version 2.0a
Assay format Chip: CM5-Chip
Antibodies against CSF-1R were captured via amine coupled capture molecules. Using the single cycle kinetics five increasing concentrations of human CSF-1R fragment D1-D3 (SEQ ID NO: 66) were injected. Human CSF-1R fragment D1-D3 was subcloned into pCMV-presS-HisAvitag expression vector.

Anti CSF-1R SC 2-4A5 (Santa Cruz Biotechnology, US; Sherr, C. J. et al., Blood 73 (1989) 1786-1793) which inhibits the ligand-receptor interaction, and Mab 3291 (R&D-Systems) were used as reference controls.

Capture molecules: Anti mouse Fcγ antibodies (from goat, Jackson Immuno Research JIR115-005-071) for antibodies according to the invention and the R&D-Systems control Mab 3291 and Anti rat Fcγ antibodies (from goat, Jackson Immuno Research JIR112-005-071) for the reference control anti CSF-1R SC 2-4A5.

Amine Coupling of Capture Molecules
Standard amine coupling according to the manufacturer's instructions: running buffer: HBS—N buffer, activation by mixture of EDC/NHS, aim for ligand density of 2000 RU; the capture-Abs were diluted in coupling buffer NaAc, pH 4.5, c=10 mg/mL; finally remaining activated carboxyl groups were blocked by injection of 1 M Ethanolamin.

Kinetic Characterization of Human CSF-1R Fragments D1-D3 Binding to MAbs <CSF-1R> at 37° C.
Running buffer: PBS (Biacore BR-1006-72)

Capturing of Mabs <CSF-1R> on flow cells 2 to 4: Flow 20 μL/min, contact time 90 seconds, c(Abs<CSF-1R>)=50 nM, diluted with running buffer+1 mg/mL BSA;
Analyte Sample:

Single Cycle Kinetics was measured at a flow rate of 30 μL/min by five consecutive injections of the analyte with concentrations, c=7.8, 31.25, 125, 500 and 2000 nM, without regeneration. Each injection was 30 seconds long and followed by a dissociation phase of 120 Seconds for the first four injections, and finally 1200 seconds for the highest concentration (=last injection).

Final regeneration was performed after each cycle using 10 mM Glycin pH 1.5 (Biacore BR-1003-54), contact time 60 seconds, flow rate 30 μL/min.

Kinetic parameters were calculated by using the usual double referencing (control reference: binding of analyte to capture molecule; Flow Cell: subdomain CSF-1R concentration "0" as Blank) and calculation with model 'titration kinetics 1:1 binding with draft'.

TABLE 10

Affinity data for binding of human CSF-1R fragment D1-D3 measured by SPR

| CSF-1R Mab | Sub domain | KD (nM) | ka (1/Ms) | kd (1/s) | t½ (min) |
|---|---|---|---|---|---|
| Mab 2F11 | D1-D3 | no binding | | | |
| Mab 2E10 | D1-D3 | no binding | | | |
| Mab 2H7 | D1-D3 | not determined | | | |
| Mab 1G10 | D1-D3 | no binding | | | |
| SC-2-4A5 | D1-D3 | no binding | | | |
| R&D-Systems 3291 | D1-D3 | 5.4 | 2.2E+5 | 1.2E−3 | 9.6 |

The antibodies Mab 2F11, Mab 2E10 and Mab 1G10 showed no binding to human CSF-1R fragment D1-D3.

Also reference control-Ab SC-2-4A5 did not bind to human CSF-1R fragment D1-D3.

The reference control Mab R&D-Systems 3291 showed binding to the human CSF-1R fragment D1-D3.

Example 12

CSF-1 Level Increase During CSF-1R Inhibition in Cynomolgus Monkey

Serum CSF-1 levels provide a pharmacodynamic marker of CSF-1R neutralizing activity of anti-human CSF-1R dimerization inhibitor hMab 2F11-e7. One male and one female cynomolgus monkey per dosage group (1 and 10 mg/kg) were intravenously administered anti-CSF1R antibody hMab 2F11-e7. Blood samples for analysis of CSF-1 levels were collected 1 week before treatment (pre-dose), 2, 24, 48, 72, 96, 168 hours post-dose and weekly for two additional weeks. CSF-1 levels were determined using a commercially available ELISA kit (Quantikine® human M-CSF) according to the manufacturer's instructions (R&D Systems, UK). Monkey CSF-1 level were determined by comparison with CSF-1 standard curve samples provided in the kit.

Administration of hMab 2F11-e7 induced a dramatic increase in CSF-1 by ~1000-fold, which depending on the dose administered lasted for 48 hr (1 mg/kg) or 15 days (10 mg/kg). Hence, a dimerization inhibitor for CSF-1R offers the advantage to not directly compete with the dramatically upregulated ligand for binding to the receptor in contrast to a ligand displacing antibody. (Results are shown in FIG. 4)

Example 13

Inhibition of Tumor Growth Under Treatment with Anti-CSF-1R Monoclonal Antibody in Combination with Chemotherapy or Cancer Immunotherapy in Subcutaneous Syngeneic MC38 Colon Carcinoma Models Cells of the murine colorectal adenocarcinoma cell line MC-38 (obtained from Beckman Research Institute of the City of Hope, Calif., USA) were cultured in Dulbecco's Modified Eagle Medium (DMEM, PAN Biotech) supplemented with 10% FCS and 2 mM L-glutamine at 37° C. in a water saturated atmosphere at 5% CO2. At the day of inoculation, MC38 tumor cells were harvested with PBS from culture flasks and transferred into culture medium, centrifuged, washed once and re-suspended in PBS. For injection of cells, the final titer was adjusted to 1×107 cells/ml. Subsequently 100 μl of this suspension (1×106 cells) were inoculated subcutaneously into 7-9 weeks old female C57BL/6N mice (obtained from Charles River, Sulzfeld, Germany). Treatment with control antibody (MOPC-21; Bio X Cell, West Lebanon), anti-murine CSF-1R mAb <mouse CSF1R> antibody at a weekly dose of 30 mg/kg i.p. alone or in combination the TLR9 agonist CpG ODN 1826 (ODN 1826, class B CpG ODN, VacciGrade, InvivoGen, 100 μg peritumoral, 1×). Tumor volume was measured twice a week and animal weights were monitored in parallel.

In a separate study with comparable set-up, primary tumors from indicated treatment groups were excised, weighed and subjected to FACS analysis. Primary tumor material was collected between study day 20-25 as indicated. To obtain single cell suspensions amenable for flow cytometry analysis the tumors were minced by using the McIlwain tissue chopper. Subsequently, the tumor pieces were resuspended in RPMI media supplemented with collagenase I, dispase II and DNAse I, incubated at 37° C. and cell suspension were passed through a mash. CD45 positive cells were enriched by magnetic cell separation according to the manufacturer's instructions (Miltenyi). Briefly cells were labeled with anti-mouse CD45 conjugated with APC (BD, Cat. No 559864) and separated with anti APC microbeads. To analyse CD8+ T cells these CD45 positive cells were stained with 0.2 μg/ml DAPI (Roche, Cat. No 10236276001 and PE conjugated CD8 antibody (eBioscience Cat. No. 12-0081-83) or PE conjugated CD4 antibody (eBioscience, Cat. No. 2-0041-83). Acquisition of data was performed with FACS Canto II and subsequently analysed with FlowJo software. Only viable cells (gated on DAPI-negative cells) were analysed to exclude cell debris and dead cells.

Monotherapy with <mouse CSF1R> antibody inhibited primary tumor growth when compared to control antibody treatment (TGI: 67%, TCR: 0.38 CI: 0.15-0.64). Also TLR9 agonist (CpG ODN 1826) monotherapy had an effect on MC38 primary tumor growth (TGI: 74%, TCR: 0.28 CI: 0.10-0.50). Addition of <mouse CSF1R> antibody to TLR9 agonist therapy led to a clearly superior anti-tumor efficacy compared to TLR9 agonist treatment alone (TGI: 95%, TCR: 0.08 CI: −0.11-0.28). (see table 11).

TABLE 11

Anti tumor Efficacy of <mouse CSF1R> antibody alone and in combination with TLR9 agonist CpG in the MC38 mouse CRC in vivo model

| Group | TGI (day 24) | TCR (day 24) | Median time to progression TV > 700 mm3 |
|---|---|---|---|
| Control (Mouse IgG1) | — | — | 21 |
| <mouse CSF1R> antibody | 67% | 0.38 | 24 |
| TLR9 agonist (CpG) | 73% | 0.28 | 24 |
| <mouse CSF1R> antibody/TLR9 agonist (CpG) | 95% | 0.08 | 46 |

Evaluation on Tumor Progression

Additionally to the assessment of median tumor volume after 2 weeks of treatment the progression of individual tumors in the study was followed until progression ≥700 mm3 (FIG. 1 (CpG is TLR9 agonist CpG ODN 1826) and Table 11)

Median time to progression ≥700 mm3 was 21 days for IgG control treatment group. Slight improvement of median progression time was achieved by treatment with <CSF1R> antibody monotherapy (24 days).

Monotherapy with TLR9 agonist resulted in a median time to progression of 24 days. Addition of TLR9 agonist (CpG) to anti-CSF-1R antibody therapy resulted in a statistically significant more than additive improvement of median time to progression (46 days) compared to anti-CSF-1R antibody monotherapy or TLR9 agonist monotherapy.

What is claimed is:

1. A method of treating cancer, the method comprising administering to a patient in need thereof an effective amount of
   i) an antibody which binds to human CSF-1R, and
   ii) a TLR9 agonist.

2. The method of claim 1, wherein the cancer expresses or overexpresses CSF-1R.

3. The method of claim 1, wherein the cancer is breast cancer, colorectal cancer, melanoma, head and neck cancer, lung cancer or prostate cancer.

4. A method of treating cancer, the method comprising administering to a patient in need thereof an effective amount of
   i) an antibody which specifically binds to the dimerization domains D4 to D5 (SEQ ID NO: 85) of the extracellular domain of human CSF-1R, and
   ii) a TLR9 agonist, wherein
      a) cell proliferation in CSF-1R ligand-dependent and/or CSF-1 ligand-independent CSF-1R expressing tumor cells is inhibited;
      b) cell proliferation of tumors with CSF-1R ligand-dependent and/or CSF-1R ligand-independent CSF-1R expressing macrophage infiltrate is inhibited;
      c) cell survival in CSF-1R ligand-dependent and/or CSF-1R ligand-independent CSF-1R expressing monocytes and macrophages is inhibited; or
      d) cell differentiation in CSF-1R ligand-dependent and/or CSF-1R ligand-independent CSF-1R expressing monocytes into macrophages is inhibited.

5. A method of treating a patient having a CSF-1R-expressing tumor or having a tumor with CSF-1R-expressing macrophage infiltrate, wherein the tumor expresses increased levels of CSF-1R ligand, the method comprising administering an effective amount of:
   i) an antibody which specifically binds to human CSF-1R, and
   ii) a TLR9 agonist.

6. The method of claim 1, 4, or 5 wherein the TLR9 agonist induces IFN-alpha, IL-6, and/or IL-12 in plasmacytoid dendritic cells (pDCs).

7. The method of claim 1, 4, or 5, wherein the TLR9 agonist is an oligodeoxynucleotide containing cytosine-phosphate-guanosine (CpG) motifs (CpG ODNs).

8. The method of claim 1, 4, or 5, wherein the antibody specifically binds to the domains D4 to D5 (SEQ ID No: 85) of the extracellular domain of human CSF-1R.

9. The method of claim 1, 4, or 5, wherein the antibody does not bind to human CSF-1R fragment delD4 (SEQ ID NO: 65).

10. The method of claim 1, 4, or 5, wherein the antibody comprises
   a) a heavy chain variable domain comprising SEQ ID NO:7 and a light chain variable domain comprising SEQ ID NO:8,
   b) a heavy chain variable domain comprising SEQ ID NO:15 and a light chain variable domain comprising SEQ ID NO:16;
   c) a heavy chain variable domain comprising SEQ ID NO:75 and a light chain variable domain comprising SEQ ID NO:76;
   d) a heavy chain variable domain comprising SEQ ID NO:83 and a light chain variable domain comprising SEQ ID NO:84;
   e) a heavy chain variable domain comprising SEQ ID NO:23 and a light chain variable domain comprising SEQ ID NO:24, or
   f) a heavy chain variable domain comprising SEQ ID NO:31 and a light chain variable domain comprising SEQ ID NO:32, or
   g) a heavy chain variable domain comprising SEQ ID NO:39 and a light chain variable domain comprising SEQ ID NO:40, or
   h) a heavy chain variable domain comprising SEQ ID NO:47 and a light chain variable domain comprising SEQ ID NO:48, or
   i) a heavy chain variable domain comprising SEQ ID NO:55 and a light chain variable domain comprising SEQ ID NO:56.

11. The method of claim 1, 4, or 5, wherein the antibody comprises
   a) a heavy chain variable domain comprising a CDR3 region of SEQ ID NO: 1, a CDR2 region of SEQ ID NO: 2, and a CDR1 region of SEQ ID NO:3, and a light chain variable domain comprising a CDR3 region of SEQ ID NO: 4, a CDR2 region of SEQ ID NO:5, and a CDR1 region of SEQ ID NO:6, or
   b) a heavy chain variable domain comprising a CDR3 region of SEQ ID NO: 9, a CDR2 region of SEQ ID NO: 10, and a CDR1 region of SEQ ID NO: 11, and a light chain variable domain comprising a CDR3 region of SEQ ID NO:12, a CDR2 region of SEQ ID NO: 13, and a CDR1 region of SEQ ID NO: 14, or
   c) a heavy chain variable domain comprising a CDR3 region of SEQ ID NO: 17, a CDR2 region of SEQ ID NO: 18, and a CDR1 region of SEQ ID NO:19, and a light chain variable domain comprising a CDR3 region of SEQ ID NO: 20, a CDR2 region of SEQ ID NO:21, and a CDR1 region of SEQ ID NO:22, or
   d) a heavy chain variable domain comprising a CDR3 region of SEQ ID NO: 25, a CDR2 region of SEQ ID NO: 26, and a CDR1 region of SEQ ID NO: 27, and a light chain variable domain comprising a CDR3 region of SEQ ID NO:28, a CDR2 region of SEQ ID NO: 29, and a CDR1 region of SEQ ID NO: 30, or
   e) a heavy chain variable domain comprising a CDR3 region of SEQ ID NO: 33, a CDR2 region of SEQ ID NO: 34, and a CDR1 region of SEQ ID NO: 35, and a light chain variable domain comprising a CDR3 region of SEQ ID NO:36, a CDR2 region of SEQ ID NO: 37, and a CDR1 region of SEQ ID NO: 38, or
   f) a heavy chain variable domain comprising a CDR3 region of SEQ ID NO:41, a CDR2 region of SEQ ID NO: 42, and a CDR1 region of SEQ ID NO:43, and a light chain variable domain comprising a CDR3 region of SEQ ID NO: 44, a CDR2 region of SEQ ID NO:45, and a CDR1 region of SEQ ID NO:46, or
   g) a heavy chain variable domain comprising a CDR3 region of SEQ ID NO: 49, a CDR2 region of SEQ ID NO: 50, and a CDR1 region of SEQ ID NO: 51, and a light chain variable domain comprising a CDR3 region of SEQ ID NO:52, a CDR2 region of SEQ ID NO: 53, and a CDR1 region of SEQ ID NO: 54; or
   h) a heavy chain variable domain comprising a CDR3 region of SEQ ID NO:69, a CDR2 region of SEQ ID NO: 70, and a CDR1 region of SEQ ID NO:71, and a light chain variable domain comprising a CDR3 region of SEQ ID NO: 72, a CDR2 region of SEQ ID NO:73, and a CDR1 region of SEQ ID NO:74, or
   i) a heavy chain variable domain comprising a CDR3 region of SEQ ID NO: 77, a CDR2 region of SEQ ID NO: 78, and a CDR1 region of SEQ ID NO: 79, and a light chain variable domain comprising a CDR3 region of SEQ ID NO:80, a CDR2 region of SEQ ID NO: 81, and a CDR1 region of SEQ ID NO: 82.

12. The method of claim 1, 4, or 5, wherein said antibody is human IgG1 subclass or human IgG4 subclass.

13. A method of treating a patient having a CSF-1R-expressing tumor or having a tumor with CSF-1R-expressing macrophage infiltrate, wherein the tumor is characterized by an increase of CSF-1R ligand, the method comprising administering an effective amount of
   i) an antibody which binds to human CSF-1R, and
   ii) a TLR9 agonist.

* * * * *